United States Patent
Bebbington et al.

(10) Patent No.: US 11,203,638 B2
(45) Date of Patent: Dec. 21, 2021

(54) METHODS AND COMPOSITIONS FOR TREATING PERENNIAL ALLERGIC CONJUNCTIVITIS AND KERATOCONJUNCTIVITIS

(71) Applicant: Allakos Inc., Redwood City, CA (US)

(72) Inventors: Christopher Robert Bebbington, San Mateo, CA (US); Bradford Andrew Youngblood, Burlingame, CA (US); Nenad Tomasevic, Foster City, CA (US)

(73) Assignee: ALLAKOS INC., Redwood City, CA (US)

( * ) Notice: Subject to any disclaimer, the term of this patent is extended or adjusted under 35 U.S.C. 154(b) by 0 days.

(21) Appl. No.: 16/610,480

(22) PCT Filed: May 4, 2018

(86) PCT No.: PCT/US2018/031226
§ 371 (c)(1),
(2) Date: Nov. 1, 2019

(87) PCT Pub. No.: WO2018/204868
PCT Pub. Date: Nov. 8, 2018

(65) Prior Publication Data
US 2020/0148766 A1    May 14, 2020

Related U.S. Application Data

(60) Provisional application No. 62/502,479, filed on May 5, 2017.

(51) Int. Cl.
| *C07K 16/28* | (2006.01) |
| *A61P 27/14* | (2006.01) |
| *A61K 9/00* | (2006.01) |
| *A61K 39/395* | (2006.01) |
| *A61K 39/00* | (2006.01) |

(52) U.S. Cl.
CPC ........ *C07K 16/2803* (2013.01); *A61K 9/0019* (2013.01); *A61K 39/3955* (2013.01); *A61P 27/14* (2018.01); A61K 2039/505 (2013.01); C07K 2317/24 (2013.01); C07K 2317/33 (2013.01); C07K 2317/732 (2013.01); C07K 2317/76 (2013.01)

(58) Field of Classification Search
None
See application file for complete search history.

(56) References Cited

U.S. PATENT DOCUMENTS

| RE30,985 E | 6/1982 | Cartaya |
| 4,419,446 A | 12/1983 | Howley et al. |
| 4,560,655 A | 12/1985 | Baker |
| 4,601,978 A | 7/1986 | Kara |
| 4,657,866 A | 4/1987 | Kumar |
| 4,676,980 A | 6/1987 | Segal et al. |
| 4,767,704 A | 8/1988 | Cleveland |
| 4,816,567 A | 3/1989 | Cabilly |
| 4,927,762 A | 5/1990 | Darfler |
| 4,965,199 A | 10/1990 | Capon et al. |
| 5,122,464 A | 6/1992 | Wilson |
| 5,122,469 A | 6/1992 | Mather |
| 5,264,365 A | 11/1993 | Georgiou |
| 5,500,362 A | 3/1996 | Robinson |
| 5,508,192 A | 4/1996 | Georgiou |
| 5,571,894 A | 11/1996 | Wels |
| 5,587,458 A | 12/1996 | King |
| 5,624,821 A | 4/1997 | Winter |
| 5,639,635 A | 6/1997 | Joly |
| 5,641,870 A | 6/1997 | Rinderknecht |
| 5,648,237 A | 7/1997 | Carter |
| 5,648,260 A | 7/1997 | Winter |
| 5,677,425 A | 10/1997 | Bodmer |
| 5,739,277 A | 4/1998 | Presta |
| 5,821,337 A | 10/1998 | Carter |
| 5,834,597 A | 11/1998 | Tso |
| 5,840,523 A | 11/1998 | Simmons et al. |
| 5,869,046 A | 2/1999 | Presta et al. |
| 5,885,573 A | 3/1999 | Bluestone |

(Continued)

FOREIGN PATENT DOCUMENTS

| EP | 2465873 A1 | 6/2012 |
| JP | 2003525615 A | 9/2003 |

(Continued)

OTHER PUBLICATIONS

"Seasonal Allergic Conjunctivitis (Hayfever)" [online][2017 archived version accessed from web.archive.org/web/20170414081345/https://www.umkelloggeye.org/conditions-treatments/seasonal-allergic-conjunctivitis-hayfever] (Year: 2017).*

Bilkhu et al. "A review of non-pharmacological and pharmacological management of seasonal and perennial allergic conjunctivitis" Contact Lens & Anterior Eye 35 (2012) 9-16. (Year: 2012).*

Morrow and Abbott. "Conjunctivitis". Am Fam Physician. Feb. 15, 1998;57(4):735-746. (Year: 1998).*

(Continued)

*Primary Examiner* — Elly-Gerald Stoica
(74) *Attorney, Agent, or Firm* — Morrison & Foerster LLP

(57) ABSTRACT

The present disclosure provides methods for the treatment of an allergic ocular disease (e.g., allergic conjunctivitis, keratoconjunctivitis, or giant papillary conjunctivitis). In particular, the present disclosure provides methods for the treatment of an allergic ocular disease through administration of antibodies that bind to human Siglec-8 or compositions comprising said antibodies. The present disclosure also provides articles of manufacture or kits comprising antibodies that bind to human Siglec-8 for the treatment of an allergic ocular disease.

23 Claims, No Drawings
Specification includes a Sequence Listing.

(56) References Cited

U.S. PATENT DOCUMENTS

| | | |
|---|---|---|
| 5,891,693 A | 4/1999 | Bebbington |
| 6,027,888 A | 2/2000 | Georgiou |
| 6,083,715 A | 7/2000 | Georgiou |
| 6,121,022 A | 9/2000 | Presta |
| 6,165,745 A | 12/2000 | Ward |
| 6,194,551 B1 | 2/2001 | Idusogie |
| 6,227,375 B1 | 5/2001 | Powollik |
| 6,248,516 B1 | 6/2001 | Winter et al. |
| 6,277,375 B1 | 8/2001 | Ward |
| 6,602,684 B1 | 8/2003 | Umana et al. |
| 6,737,056 B1 | 5/2004 | Presta |
| 6,821,505 B2 | 11/2004 | Ward |
| 6,982,321 B2 | 1/2006 | Winter |
| 7,087,409 B2 | 8/2006 | Barbas, III |
| 7,317,091 B2 | 1/2008 | Lazar |
| 7,335,742 B2 | 2/2008 | Presta |
| 7,557,191 B2 | 7/2009 | Abrahamson |
| 7,745,421 B2 | 6/2010 | Bochner |
| 7,871,612 B2 | 1/2011 | Abrahamson |
| 7,981,843 B2 | 7/2011 | Flynn |
| 8,178,512 B2 | 5/2012 | Bochner |
| 8,197,811 B2 | 6/2012 | Abrahamson |
| 8,207,305 B2 | 6/2012 | Abrahamson |
| 8,357,671 B2 | 1/2013 | Paulson |
| 8,574,907 B2 | 11/2013 | Alley |
| 9,546,215 B2 * | 1/2017 | Bebbington ............ A61P 37/00 |
| 10,183,996 B2 | 1/2019 | Bebbington |
| 10,604,577 B2 | 3/2020 | Bebbington |
| 10,774,145 B2 | 9/2020 | Bebbington |
| 2002/0106738 A1 | 8/2002 | Foussias |
| 2002/0164328 A1 | 11/2002 | Shinkawa |
| 2003/0092091 A1 | 5/2003 | Abrahamson |
| 2003/0115614 A1 | 6/2003 | Kanda |
| 2003/0157108 A1 | 8/2003 | Presta |
| 2003/0190311 A1 | 10/2003 | Dall |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2005/0014934 A1 | 1/2005 | Hinton |
| 2005/0123546 A1 | 6/2005 | Umana |
| 2006/0134098 A1 | 6/2006 | Bebbington |
| 2007/0134259 A1 | 6/2007 | Bundle |
| 2007/0264258 A1 | 11/2007 | Abrahamson |
| 2008/0050310 A1 | 2/2008 | Ebens, Jr. |
| 2008/0139485 A1 | 6/2008 | Bochner |
| 2008/0213212 A1 | 9/2008 | Abrahamson |
| 2009/0238837 A1 | 9/2009 | Paulson |
| 2010/0056760 A1 | 3/2010 | Abrahamson |
| 2011/0046078 A1 | 2/2011 | Bochner |
| 2011/0059107 A1 | 3/2011 | Allison |
| 2011/0217319 A1 | 9/2011 | Abrahamson |
| 2011/0293631 A1 | 12/2011 | Thumbikat |
| 2012/0214975 A1 | 8/2012 | Sandig |
| 2015/0203578 A1 | 7/2015 | Bebbington |
| 2017/0073413 A1 | 3/2017 | Bebbington |
| 2017/0114138 A1 | 4/2017 | Bebbington |
| 2017/0209556 A1 | 7/2017 | Bebbington |
| 2018/0179279 A1 | 6/2018 | Bebbington |
| 2019/0338027 A1 | 11/2019 | Youngblood |
| 2020/0054723 A1 | 2/2020 | Bebbington |
| 2020/0181270 A1 | 6/2020 | Bebbington |
| 2020/0270344 A1 | 8/2020 | Bebbington |
| 2021/0107977 A1 | 4/2021 | Bebbington et al. |

FOREIGN PATENT DOCUMENTS

| | | | | |
|---|---|---|---|---|
| JP | 2005532253 A | | 10/2005 | |
| JP | 2009534052 A | | 9/2009 | |
| KR | 10-2015-0044687 | * | 4/2015 | ........... A61K 39/395 |
| KR | 20150044680 A | | 4/2015 | |
| KR | 20150044687 A | | 4/2015 | |
| WO | 198700195 A1 | | 1/1987 | |
| WO | 199003430 A1 | | 4/1990 | |
| WO | 199306213 A1 | | 4/1993 | |
| WO | 199308829 A1 | | 5/1993 | |
| WO | 199316185 A2 | | 8/1993 | |
| WO | 199411026 A2 | | 5/1994 | |
| WO | 1994029351 A2 | | 12/1994 | |
| WO | 1994029351 A3 | | 12/1994 | |
| WO | 199730087 A1 | | 8/1997 | |
| WO | 199858964 A1 | | 12/1998 | |
| WO | 199922764 A1 | | 5/1999 | |
| WO | 199951642 A1 | | 10/1999 | |
| WO | 200061739 A1 | | 10/2000 | |
| WO | 200042072 A3 | | 11/2000 | |
| WO | 200129246 A1 | | 4/2001 | |
| WO | 2001066126 A1 | | 9/2001 | |
| WO | 2003035835 A2 | | 5/2003 | |
| WO | 2003035835 A3 | | 10/2003 | |
| WO | 2003084570 A1 | | 10/2003 | |
| WO | 2003085119 A1 | | 10/2003 | |
| WO | 2003011878 A3 | | 11/2003 | |
| WO | 2004056312 A2 | | 7/2004 | |
| WO | 2005035586 A1 | | 4/2005 | |
| WO | 2005035778 A1 | | 4/2005 | |
| WO | 2004056312 A3 | | 5/2005 | |
| WO | 2005053742 A1 | | 6/2005 | |
| WO | 2005116088 A2 | | 12/2005 | |
| WO | 2007056525 A2 | | 5/2007 | |
| WO | 2008077546 A1 | | 7/2008 | |
| WO | 2008145142 A1 | | 12/2008 | |
| WO | 2010063785 A2 | | 6/2010 | |
| WO | 2011147982 A2 | | 12/2011 | |
| WO | 2012120500 A3 | | 11/2012 | |
| WO | 2013120066 A1 | | 8/2013 | |
| WO | 2013126834 A1 | | 8/2013 | |
| WO | 2015061441 A1 | | 4/2015 | |
| WO | 2015089117 A1 | | 6/2015 | |
| WO | WO-2015089117 A1 | * | 6/2015 | ............. A61P 37/00 |
| WO | 2015131155 A1 | | 9/2015 | |
| WO | 2016205567 A1 | | 12/2016 | |
| WO | 2017070527 A1 | | 4/2017 | |
| WO | 2018129400 A1 | | 7/2018 | |
| WO | 2018204871 A1 | | 11/2018 | |
| WO | 2019213468 A1 | | 11/2019 | |
| WO | 2020168271 A1 | | 8/2020 | |

OTHER PUBLICATIONS

McGill et al. "Allergic eye disease mechanisms" Br J Ophthalmol 1998;82:1203-1214 (Year: 1998).*

Di Gioacchino et al. "Increase in CD45RO+ Cells and Activated Eosinophils in Chronic Allergic Coniunctivitis". Immunobiology (1999/2000) 201, 541-551. (Year: 2000).*

Wynne et al. "Comparison of Subcutaneous and Intravenous Administration of Trastuzumab : A Phase I/Ib Trial in Healthy Male Volunteers and Patients With HER2. . . " The Journal of Clinical Pharmacology 53(2) 192-201 (2012). (Year: 2012).*

Satoh et al. "Non-fucosylated therapeutic antibodies as next-generation therapeutic antibodies". Expert Opin. Biol. Ther. (2006) 6(11). (Year: 2006).*

Nelson et al. "Demystified . . . Monoclonal antibodies". J Clin Pathol: Mol Pathol 2000;53:111-117 (Year: 2000).*

Bielory, L. "Update on ocular allergy treatment". Expert Opin. Pharmacother. (2002) 3(4) (Year: 2002).*

Bielory, L. "Ocular Allergy". Mount Sinai Journal of Medicine 78:740-758, 2011. (Year: 2011).*

Kiwamoto et al. "Siglec-8 as a drugable target to treat eosinophil and mast cell-associated conditions". Pharmacology & Therapeutics 135 (2012) 327-336 (Year: 2012).*

Tateno et al. "Mouse Siglec-F and human Siglec-8 are functionally convergent paralogs that are selectively expressed on eosinophils and recognize 6'-sulfo-sialyl Lewis X as a preferred glycan ligand" Glycobiology vol. 15 No. 11 pp. 1125-1135, 2005 (Year: 2005).*

Leonardi, A. "The Central Role of Conjunctival Mast Cells in the Pathogenesis of Ocular Allergy". Current Allergy and Asthma Reports 2002, 2:325-331. (Year: 2002).*

Alegre, M. et al. (Jun. 1994). "A Non-Activating "Humanized" Anti-CD3 Monoclonal Antibody Retains Immunosuppressive Properties In Vivo," Transplantation, 57(11):1537-1543.

(56) References Cited

OTHER PUBLICATIONS

Almagro, J. et al. (Jan. 2008). "Humanization of Antibodies," Frontiers in Bioscience 13:1619-1633.

Altrichter, S. et al. (Jun. 4, 2019) "Efficacy and Safety Data of AK002, an Anti-Siglec-8 Monoclonal Antibody, in Patients With Multiple Forms of Uncontrolled Chronic Urticaria (CU): Results From an Open-Label Phase 2a Study," Allergy: European Journal of Allergy and Clinical Immunology 74(S106): pp. 120. Abstract No. LBOA1701.

Andersson, C.K. et al. (2011). "Activated MCTC Mast Cells Infiltrate Diseased Lung Areas in Cystic Fibrosis and Idiopathic Pulmonary Fibrosis," Respiratory Research 12:139-151, 13 pages.

Angal, S. et al. (Jan. 1993). "A Single Amino Acid Substitution Abolishes the Heterogeneity of Chimeric Mouse/human (lgg4) Antibody," Molecular Immunology, 30(1):105-108.

Arie, J-P. et al. (Jan. 1, 2001). "Chaperone Function of FkpA, A Heat Shock Prolyl Isomerase, in the Periplasm of *Escherichia Coli*," Molecular Micorbioiogy 39(1):199-210.

Armour, K.L. et al. (1999). "Recombinant Human IgG Molecules Lacking FcGamma Receptor I Binding and Monocyte Triggering Activities," European Journal of Immunology 29:2613-2624.

Bachmann, B.J. (1987). "Section G. Strains and Useful Strain Constructions. Derivations and Genotypes of Some Mutant Derivatives of *Escherichia coli* K-12," Cellular and Molecular Biology, vol. 2, Neidhardt, F. C. et al., Washington, D.C., American Society for Microbiology, pp. 1190-1219.

Barnes, D. et al. (Mar. 1, 1980). "Methods for Growth of Cultured Cells in Serum-Free Medium," Anal. Biochem. 102(2):255-270.

Bass, S. et al. (1990). "Hormone Phage: An Enrichment Method for Variant Proteins With Altered Binding Properties," Proteins 8:309-314.

Beckett, E.L. et al. (Mar. 2013). "A Short-Term Model of COPD Identifies A Role for mast cell Tryptase," J. Allergy Clin. Immunol. 131(1):752-762.

Berges-Gimeno, M. P. et al. (Nov. 2002). "The Natural History and Clinical Characteristics of Asprin-Exacerbaated Respiratory Disease," Annals of Allergy, Asthma & Immunology 89:474-478.

Boerner, P. et al. (Jul. 1, 1991). "Production of a Antigen-Specific Human Monoclonal Antibodies from In Vitro-Primed Human Splenocytes," J. Immunol. 147(1):86-95.

Bothmann, H. et al., (Jun. 2, 2000). "The Periplasmic *Escherichia coli* Peptidyiprolyl cis,trans-Isomerase FkpA," The Journal of Biological Chemistry 275(22):17100-17105.

Brennan, M. et al. (Jul. 5, 1985). "Preparation of Bispecific Antibodies by Chemical Recombination of Monoclonal Immunoglobulin G1 Fragments," Science 229:81-83.

Brodeur, B.R. et al. (1987). "Mouse-Human Myeloma Partners for the Production Monoclonal Antibody Production of Heterohybridomas," Chapter 4 in Techniques and Applications, Marcel Dekker, Inc., New York, pp. 51-63.

Brunner, K.T. et al. (1968). "Quantitative Assay of the Lytic Action of Immune Lymphoid Cells on 51Cr-Labelled Allogeneic Target Cells in Vitro; Inhibition by Isoantibody and by Drugs," Immunology 14:181-196.

Bryson, J.M. et al. (2003). "Local and Systemic Eosinophilia in Patients Undergoing Endoscopic Sinus Surgery for Chronic Rhinosinusitis with and Without Polyposis," Clin. Otolaryngol. 28:55-58.

Bruggermann, M. et al. (1993). "Designer Mice: The Production Of Human Antibody Repertoires In Transgenic Animals," Year Immunology 7:33-40.

Carter, P. et al. (Feb. 1992). "High Level *Escherichia coli* Expression and Production of a Bivalent Humanized Antibody Fragment," BioTechnology 10:163-167.

Carter, P. et al. (May 1992). "Humanization of An Anti-p185HER2 Antibody For Human Cancer Therapy," Proc. Natl. Acad. Sci. USA 89:4285-4289.

Casassus, P. et al. (2002). "Treatment of Adult Systemic Mastocytosis With Interferon-α: Results of a Multicentre Phase II Trial on 20 Patients," British Journal of Haematology 119:1090-1097.

Casset, F. et al. (2003) "A Peptide Mimetic Of An Anti-CD4 Monoclonal Antibody By Rational Design," BBRC 307:198-205.

Chen, J. et al. (Jul. 9, 1999). "Chaperone Activity of DsbC*," The Journal of Biological Chemistry 274 (28):19601-19605.

Chen, Y. et al. (1999). "Selection and Analysis of an Optimized Anti-VEGF Antibody: Crystal Structure of an Affinity-Matured Fab In Complex With Antigen," J. Mol. Biol 293:865-881.

Cheng, M. et al. (2013). "NK cell-based Immunotherapy for Malignant Diseases," Cellular & Molecular Immunology 10:230-252.

Chothia, C. et al. (Aug. 20, 1987). "Canonical Structures for the Hypervariable Regions of Immunoglobulins," J. Mol. Biol. 196(4):901-917.

Chung, C. H. (2008) "Managing Premedications and the Risk for Reactions to Infusional Monoclonal Antibody Therapy," The Oncologist 13(6):725-732.

Clinicaltrials.gov. (Apr. 5, 2018). "A Study to Assess the Efficacy and Safety of AK002 in Subjects With Antihistamine-Resistant Chronic Urticaria, NCT03436797," downloaded from https://clinicaltrials.gov/ct2/history/NCT03436797?V_6=View#StudyPageTop, on Jun. 5, 2019, 8 pages.

Clinicaltrials.gov. (Feb. 28, 2020). "A Study of AK002 in Patients With Eosinophilic Gastritis and/or Eosinophilic Gastroenteritis IENIGMA)," NCT03496571 downloaded https://clinicaltrials.gov/ct2/history/NCT03496571?A=21&B=21&C=merged#StudyPageTop, 13 pages.

Clynes, R. et al. (Jan. 1998), "Fc Receptors are Required in Passive and Active Immunity to Melanoma," Proc. Natl. Acad. Sci. USA 95:652-656.

Cunningham, B.C. et al. (Jun. 2, 1989). "High-Resolution Epitope Mapping of hGH-Receptor Interactions by Alanine-Scanning Mutagenesis," Science 244:1081-1085.

Duncan, A.R. et al. (Apr. 21, 1988). "The Binding Site for C1q on IgG," Nature 322:738-740.

Duncan, A.R. et al. (Apr. 7, 1988). "Localization of the Binding Site for The Human High-affinity Fc Receptor On IgG," Nature 332:563-564.

Eswar, N. et al. (Oct. 2006), "Comparative Protein Structure Modeling Using Modeller," Current Protocols in Bioinformatics, Unit-5.6:1-47.

European Examination Report dated Apr. 1, 2019, for European Patent Application No. 15755175.5, filed on Aug. 25, 2016, 6 pages.

European Examination Report dated Apr. 17, 2020, for European Patent Application No. 16812473.3, filed on Jan. 10, 2018, 3 pages.

European Examination Report dated Jul. 15, 2020, for European Patent Application No. 16858333.4, filed on Apr. 27, 2019, 5 pages.

European Extended Search Report dated May 15, 2019 for European Patent No. 16858333.4, filed on Apr. 17, 2019, 7 pages.

European Extended Search Report dated Nov. 15, 2018, for European Patent No. 16812473.3, filed on Jan. 10, 2018, 10 pages.

European Partial Search Report dated Aug. 30, 2017, for European Patent Application No. 15755175.5, filed on Aug. 25, 2016, 8 pages.

European Search Report dated Dec. 8, 2017, for European Patent Application No. 15755175.5, filed on Aug. 25, 2016, 15 pages.

Extended European Search Report dated Jan. 17, 2020, for European Patent Application No. 19186014.7, filed on Jul. 12, 2019, 12 pages.

Extended European Search Report dated Jun. 29, 2017, for European Patent Application No. 14869424.3, filed on Jun. 24, 2016, 11 pages.

Fairclough, L. et al. (2008). "Killer Cells in Chronic Obstructive Pulmonary Disease," Clinical Science 114:533-541.

Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1, 4-N-Acetylglucosaminyltransferase III and Golgi α-Mannosidase," Biotechnology and Bioengineering 93(5):851-861.

Florian, S. et al. (2006, e-pub. Jan. 6, 2006). "Systemic Mastocytosis (SM) Associated With Chronic Eosinophilic Leukemia (SM-CEL): Detection of PIP1L1/PDSGFRα, Classification by WHO Criteria, and Response to Therapy With Imatinib," Leukemia Research 30:1201-1205.

(56) References Cited

OTHER PUBLICATIONS

Floyd, H. et al. (Jan. 14, 2000). "Siglec-8: A novel Eosinophil-Specific Member of the Immunoglobulin Superfamily," Journal of Biological Chemistry 275(2):861-866.

Fokkens, W.J. et al. (Mar. 2012). "European Position Paper on Rhinosinusitis and Nasal Polyps 2012", EPOS 50 (Supplemental 23):1-299.

Fulkerson, P.C. et al. (Feb. 2013). "Targeting Eosinophils in Allergy, Inflammation and Beyond," Nat. Rev. Drug Discov. 12(2):1-23 Article NRD3838.

Gevaert, P. et al. (Jan. 2013). "Omalizumab is Effective in Allergic and Nonallergic Patients with Nasal Polyps and Asthma," The Journal of Allergy and Clinical of Immunology 131(1):110-116.

Ghetie, V. et al. (1997). "Increasing the Serum Persistence of an Igg Fragment by Random Mutagenesis," Nat Biotech 15:637-640.

Goodman, J.W. et al. (1994). "Immunoglobulin Proteins," Chapter 6 in Basic And Clinical Immunology, Eighth Edition, Appleton & Lange: Norwalk, Conneticut, pp. 66-79.

Gotlib, J. et al. (Mar. 28, 2013). "International Working Group—Myeloproliferative Neoplasms Research and Treatment (IWG-MRT) & European Competence Network on Mastocytosis (ECNM) Consensus Response Criteria in Advanced Systemic Mastocytosis," Blood 121(13):2393-2401.

Graham. F.L. et al. (1977). "Characteristics of a Human Cell Line Transformed by DNA from Human Adenovirus Type 5," J. Gen Virol. 36:59-74.

Guhl, S. et al. (2011). "Long-Term Cultured Human Skin Mast Cells Are Suitable for Pharmacological Studies of Anti-Allergic Drugs Due to High Responsiveness to FceRI Cross-Linking," Bioscience, Biotechnology, and Biochemistry 75(2):382-384.

Gunten, S.V. et al. (Apr. 2007). "Intravenous Immunoglobulin Preparations Contain Anti-Siglec-8 Autoantibodies," Journal of Allergy and Clinical Immunology 119(4):1005-1011.

Guss, B. et al. (Jul. 1986). "Structure of the IgG-Binding Regions of Streptococcal Protein G," EMBO J. 5(7):1567-1575.

Guyer, R.L. et al. (Aug. 1976). "Immunoglobulin Binding By Mouse Intestinal Epithelial Cell Receptors," J. Immunol. 117(2):587-593.

Ham, R.J. et al. (1979). "Media and Growth Requirements," Meth. Enz. 58:44-93.

Hamers-Casterman, C. et al. (Jun. 3, 1993). "Naturally Occurring Antibodies Devoid Of Light Chains," Nature 363(64281):446-448.

Hara, H. et al. (1996) "Overproduction Of Penicillin-Binding Protein 7 Suppresses Thermosensitive Grovvth Defect At Low Osmolarity Due To An Spr Mutation Of *Escherichia Coli*," Microhial Drug Resistance 2(1):63-72.

Harris, W.J. (1995). "Production of Humanized Monoclonal and Antibodies for in vivo Imaging and Therapy," Biochem. Soc. Transactions 23:1035-1038.

Hermine, O. et al. (May 2008). "Case-Control Cohort study of Patients' Perceptions of Disability in Mastocytosis," Plos ONE 3(5):1-14.

Hoermann, G. et al. (2014). "CD52 is a Molecular Target in Advanced Systemic Mastocytosis," FASEB J. 28(8):3540-3551.

Holm, P. et al. (Feb. 2007). "Functional Mapping and Single Chain Construction Of The Anti-Cytokeratin 8 Monoclonal Antibody TS1," Mol. Immunol. 44(6):1075-1084.

Hori, Y.S. et al. (Jun. 2016). "Eosinopenia as A predictive Factor of the Short-Term Risk of Mortality and Infection After Acute Cerebral Infarction," J. Stroke Cerebrovasc. Dis. 25(6):1307-1312.

Hu, Y. et al. (Mar. 2012). "Diagnostic Significance of Blood Eosinophil Count in Eosinophilic Chronic Rhinosinusitis With Nasal Polys in Chinese Adults," Laryngoscope 122:498-503.

Hudson, P.J. et al. (Jan. 2003). "Engineered Antibodies," Nature Medicine 9(1):129-134.

Hudson, S.A. et al. (2009). "Eosinophil-Selective Binding and Proapoptotic Effect in Vitro pf a Synthetic Siglec-8 Ligand, Polymeric 6'-Sulfated Sialyl Lewis X," The Journal of Pharmacology and Experimental Therapeutics 330(2):608-612.

Hudson, S.A. et al. (Dec. 2011). "Developmental, Malignancy-Related, and Cross-Species Analysis of Eosinophil, Mast Cell, and Basophil Siglec-8 Expression," Journal of Clinical Immunology 31(6):1045-1053.

Hurle, M.R. et al. (1994). "Protein Engineering Techniques for Antibody Humanization," Curr. Op. Biotech. 5(4):428-433.

Hutchins, J.T. et al. (Dec. 1995). "Improved Biodistribution, Tumor Targeting, and reduced Immunogenicity in Mice with a Gamma 4 Variant of Campath-IH," Proceedings of the National Academy of Sciences 92:1980-11984.

Idusogie, E.E. et al. (2000). "Mapping of the C1q Binding Site on Rituxan, a Chimeric Antibody With a Human IgG1 Fc," J. Immunol. 164:4178-4184.

Idusogie, E.E. et al. (2001). "Engineered Antibodies With Increased Activity to Recruit Complement," J.Immunol. 166:2571-2575.

International Preliminary Report on Patentability received for PCT Application No. PCT/US2016/037935, dated Dec. 28, 2017, 11 pages.

International Preliminary Report on Patentability received for PCT Application No. PCT/US2016/058199, dated Apr. 24, 2018, 6 pages.

International Preliminary Report on Patentability received for PCT Application No. PCT/US2018/012694, dated Jul. 9, 2019, 6 pages.

International Preliminary Report on Patentability received for PCT Application No. PCT/US2018/031226, dated Nov. 14, 2019, 11 pages.

International Preliminary Report on Patentability received for PCT Application No. PCT/US2018/031231, dated Nov. 14, 2019, 10 pages.

International Preliminary Report on Patentability received for PCT Patent Application No. PCT/US2014/069409, dated Jun. 23, 2016, 12 pages.

International Preliminary Report on Patentability received for PCT Patent Application No. PCT/US2015/018188, dated Sep. 15, 2016, 8 Pages.

International Search Report and Written Opinion received for PCT Application No. PCT/US2014/069409, dated Mar. 6, 2015, 19 pages.

International Search Report and Written Opinion received for PCT Application No. PCT/US2015/018188, dated Apr. 28, 2015, 13 pages.

International Search Report and Written Opinion received for PCT Application No. PCT/US2016/037935, dated Aug. 10, 2016, 15 pages.

International Search Report and Written Opinion received for PCT Application No. PCT/US2016/058199, dated Jan. 9, 2017, 11 pages.

International Search Report and Written Opinion received for PCT Application No. PCT/US2018/012694, dated Mar. 20, 2018, 12 pages.

International Search Report and Written Opinion received for PCT Application No. PCT/US2018/031226, dated Aug. 6, 2018, 16 pages.

International Search Report and Written Opinion received for PCT Application No. PCT/US2018/031231, dated Aug. 1, 2018, 19 pages.

International Search Report and Written Opinion received for PCT Application No. PCT/US2019/030523, dated Jul. 2, 2019, 10 pages.

International Search Report and Written Opinion received for PCT Application No. PCT/US2020/018405, dated Apr. 7, 2020, 14 pages.

International Search Report and Written Opinion received for PCT Application No. PCT/US2020/044583, dated Sep. 18, 2020, filed on Jul. 31, 2020, 13 pages.

Ishitoya, J. (Sep. 29, 2007). "Eosinophilic Sinusitis/Eosinophilic Otitis Media—Chronic Eosinophilic Inflammation of the Upper Respiratory Tract Which has Been Recently Focused," Japan Medical Journal 4353:.53-57, with English Translation, 17 pages total.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain

(56) References Cited

OTHER PUBLICATIONS

Joining Region Blocks B-Cell Development and Antibody Production," Proc. Natl. Acad. Sci. USA 90(6):2551-2555.
Jefferis, R. et al. (Dec. 2, 1996). "Modulation of Fc(gamma)r and Human Complement Activation By Igg3-core Oligosaccharide Interactions," Immunology Letters 54(2-3):101-104.
Jefferis, R. et al. (Jan. 2, 1995). "Recognition Sites on Human Igg For Fcγ Receptors: The Role of Glycosylation" Immunology Letters 44(2-3):111-117.
Jefferis, R. et al. (Jul./Aug. 2009). "Human Immunoglobulin Allotypes," MABS 1(4):1-7.
Jefferis, R. et al. (Jun. 3, 2002). "Interaction Sites on Human IgG-Fc for FcγR: Current Models," Immunology Letters 82(1-2):57-65.
Jenkins, C. et al. (2004). "Systematic Review of Prevalence of Asprin Induced Astham and its Implications for Clinical Practice," BMJ 328(7437):1-7.
Johnson, G. et ai. (2004)."The Kabat Database and a Bioinformatics Example," Antibody Engineering Methods in Molecular BiologyTM 248:11-25.
Joly, J.C. et al. (Mar. 1998). "Overexpression of *Escherichia coli* Oxidoreductases Increases Recombinant Insulin-like Growth Factor-I Accumulation," Proc. Natl. Acad. Sci. USA 95:2773-2777.
Jones, P. et al. (May 29, 1986). "Replacing The Complementarity-Determining Regions in A Human Antibody With Those From A Mouse," Nature 321:522-525.
Kikly, K.K. et al. (Jun. 2000). "Identification Of Saf-2, A Novel Siglec Expressed On Eosinophils, Mast. Cells, And Basophils," The Journal of Allergy and Clinical Immunology 105(6):1093-1100.
Kiladjian, J.J. et al. (2006). "Cytolytic Function and Survival of Natural Killer Cells are Severely Altered in Myelodysplastic Syndromes," Leukemia 20:463-470.
Kim, J-K. et al. (1994). "Localization of the Site of the Murine IgGI Molecule That is Involved in Binding to the Murine Intestinal Fc Receptor," Eur. J. Immunol. 24:2429-2434.
Kim, J.H. et ai. (Oct. 2013). "Natural Killer Cells from Patients with Chronic Rhinosinusitis have Impaired Effector Functions," Plos One 8(10):1-9.
Kiwamoto, T. et al. (Sep. 2012). "Siglec-8 as a Drugable Target to Treat Eosinophil and Mast Cell Associated Conditions," Pharmacology & Therapeutics 135(3):327-336, 22 pages.
Kowalski, M.L., "Aspirin Exacerbated Respiratory Disease (N-ERD)," World Allergy Organization, as posted on http://www.worldallergy.org/professional/allergic_diseases_center/aspirin/ last visited on Feb. 20, 2018, 7 pages.
Kozbor, D. (Dec. 1984). "A Human Hybrid Myeloma for Production of Human Monoclonal Antibodies," J. Immunol. 133(6):3001-3005.
Lange, B. et ai. (Feb. 2011). "The Sino-Nasal Outcome Test 22 Validated for Danish Patients," Dan. Med. Bull 58(2):1-6.
Lazar, G.A. et al. (Mar. 14, 2006)."Engineered Antibody Fc Variants with Enhanced Effector Function," PNAS 103(11):4005-4010.
Lefranc, M-P. (2003). "IMGT, The International ImMunoGeneTics Database®," Nucleic Acids Research 31(1):307-310.
Lichtenfels, R. et al. (Jun. 24, 1994). "CARE-LASS (calcein-release-assay), An Improved Fluorescence-based Test System to Measure Cytotoxic T Lymphocyte Activity," Journal of Immunological Methods 172(2):227-239.
Lindmark, R. et al. (1983). "Binding of Immunoglobulins to Protein A and Immunoglobulin Levels in Mammalian Sera," J. Immunol. Meth. 62:1-13.
Lund, J. et al. (Dec. 1, 1996). "Multiple Interactions of IgG With Its Core Oligosaccharide Can Modulate Recognition By Complement and Human Fcγ Receptor I and Influence The Synthesis Of its Oligosaccharide Chains," J. Jmmunol. 157(11):4963-4969.
Lund, J. et al. (Jan. 1992). "Multiple Binding Sites on the Ch2 Domain of IgG for Mouse Fcγr11," Molecular Immunology 29(1):53-59.
Lund, J. et al. (Jan. 1995). "Oligosaccharide-Protein Interactions in IgG can Modulate Recognition by FcGamma Receptors," FASEB 9:115-119.

Lund, J. et al. (Oct. 15, 1991). "Human FcγRi And FcγRii Interact With Distinct but Overlapping Sites On Human IgG1," The Journal of Immunology 147(8):2657-2662.
Maccallum, R.M. et al. (1996). "Antibody-Antigen Interactions: Contact Analysis and Binding Site Topography," Journal of Molecular Biology 262:732-745.
Marcondes, A.M. et al. (Feb. 26, 2008). "Dysregulation of IL-32 in Myelodysplastic Syndrome and Chronic Myelomonocytic Leukemia Modulates Apoptosis and Impairs NK Function," PNAS 105(8):2865-2870.
Mather, J.P. et al. (1980). "Establishment and Characterization Of Two Distinct Mouse Testicular Epithelial Cell Lines," Biology of Reproduction 23:243-252.
Mather, J.P. et al. (1982). "Culture of Testicular Cells in Hormone-Supplemented Serum-Free Medium," Annals N.Y. Acad. Sci. 383:44-68.
Milstein, C. et al. (Oct. 6, 1983). "Hybrid Hybridomas and Their Use In Immunohistochemistry," Nature 305:537-540.
Morimoto, K. et al. (1992). "Single-Step Purification of F(AB')2 Fragments of Mouse Monoclonal Antibodies (Immunoglobulins G1) By Hydrophobic Interaction High Performance Liquid Chromatography Using TSKgel Phenyl-5PW," J. Biochem. Biophys. Method 24:107-117.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Mroz, R.M. et al. (2013). "Siglec-8 in Induced Sputum of COPD Patients," Advances in Experimental Medicine and Biology 788:19-23.
Munson, P.J. et al. (1980). "Ligand: A Versatile Computerize Approach for Characterization of Ligand-Binding Systems," Anal. Biochem. 107:220-239.
Muroi, A. et al. (Oct. 2011). "The Composite Effect of Transgenic Plant Volatiles for Acquired Immunity to Herbivory Caused by Inter-Plant Communications," Plus One 6(10):1-8.
Murray, J.A. et al. (Oct. 2019). "Symptomatic Patients Suspected of Eosinophilic Gastritis and/or Enteritis Have Elevated Mucosal Mast Cell Counts Without Eosinophilia: A New Diagnostic Entity?," American Journal of Gastroenterology 114:S693-S694, Abstract No. 1244.
Non-Final Office Action dated Dec. 26, 2017, for U.S. Appl. No. 15/121,756, filed Aug. 25, 2016, 22 pages.
Nutku, E. et al. (Jun. 15, 2003). "Ligation of Siglec-8: A Selective Mechanism for Induction of Human Eosinophil Apoptosis," Blood 101(12):5014-5020.
Nutku, E. et al. (Oct. 28, 2005). "Mechanism of Siglec-8-induced Human Eosinophil Apoptosis: Role of Caspases and Mitochondrial Injury," Biochemical and Biophysical Research Communications 336(3):918-924.
O'Donnell, R. et al. (May 2006). "Inflammatory cells in the airways in COPD," Thorax. 61(5):448-454.
Okazaki, A. et al. (Mar. 5, 2004). "Fucose Depletion From Human IgG1 Oligosaccharide Enhances Binding Enthalpy And Association Rate Between IgG1 and FcγRIIIa," J. Mol. Biol. 336(5):1239-1249.
O'Brien-Ladner, A.R. et al. (1993). "Bleomycin Injury of the Lung in a Mast-Cell-Deficient Model," Agents Actions 39:20-24.
O'Reilly, M.K. et al. (May 2009). "Siglecs as Targets for Therapy in Immune Cell Mediated Diseases," Trends Parmacol. Sci. 30(5):240-248.
Pahl, J. et al. (2015), "Tricking the Balance: NK Cells in Anti-Cancer Immunity," Immunobiology, pp. 1-10.
Patel, A.K. et al. (1995). "An improved assay for antibody dependent cellular cytotoxicity based on time resolved fluorometry," J Immunol Method 184(1):29-38.
Patnaik, M.M. et al. (May 2007). "Systemic Mastocytosis: A Concise Clinical and Laboratory Review," Arch. Pathol. Lab. Med. 131:784-791.
Paul, W. (1993) "Fundamental Immunology," Third edition, Raven Press: New York, NY:292-295.
Pillai, S. et al. (2012). "Siglecs and Immune Regulation," Annual Review of Immunology 30:357-392.

(56) References Cited

OTHER PUBLICATIONS

Pluckthun, A. (1994). "Antibodies From *Escherichia coli*," Chapter 11 in The Pharmacology of Monoclonal Antibodies, Rosenburg and Moore eds., Springer-Verlag, New York, N.Y., pp. 269-315.
Presta, L.G. (1992). "Antibody Engineering," Current Opinion in Structural Biology 2:593-596.
Presta, L.G. et al. (2002). "Engineering Therapeutic Antibodies for Improved Function," Biochemical Society Transactions 30(4):487-490.
Presta, L.G. et al. (Sep. 1, 1993). "Humanization of an Antibody Directed Against IgE," J. Immunol. 151(5):2623-2632.
Prieto, A. et al. (2001). "Defective Natural Killer and Phagocytic Activities in Chronic Obstructive Pulmonary Disease are Restored by Glycophosphopeptical (Inmunoferón)," American Journal of Respiratory and Critical Care Medicine 163:1578-1583.
Proba, K. et al. (1995). "Functional Antibody Single-chain Fragments From The Cytoplasm of *Escherichia coli:* Influence of Thioredoxin Reductase (trxb)," Gene 159(2):203-207.
Rahimi-Rad, M. et al. (2015). "Eosinopenia as a Marker of Outcome in Acute Exacerbations of Chronic Obstructive Pulmonary Disease," J. Clin. Med. 10(1):10-13.
Ramm, K. et al. (2000). "The Periplasmic *Escherichia coli* Peptidylprolyl cis,Trans-isomerase FkpA," The Journal of Biological Chemistry 275(22):17106-17113.
Rasmussen, H. et al. (Feb. 2018). "A Randomized, Double-Blind, Placebo-Controlled, Ascending Dose Phase 1 Study of AK002, A Novel Siglec-8 Selective Monoclonal Antibody, in Healthy Subjects," J. Allergy Clin. Immunol. 141(2):AB403, Abstract No. L15, 1 page.
Ravetch, J.V. et al. (1991). "Fc-Receptors," Annu. Rev. Immunol. 9:457-492.
Reddy, M.P. et al. (2000). "Elimination of Fc Receptor-Dependent Effector Functions of a Modified IgG4 Monoclonal Antibody to Human CD4," The Journal of Immunology 164:1925-1933.
Reyes, G.R. et al. (Jun. 17, 1982). "Expression of Human γ-interferon cDNA Under the Control of a Thymidine Kinase Promoter from Herpes Simplex Virus," Nature 297:598-601.
Riechmann, L. et al. (Mar. 24, 1988). "Reshaping Human Antibodies for Therapy," Nature 332:323-327.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rubinstein, E. et al. (Oct. 2011). "Siglec-F Inhibition Reduces Esophageal Eosinophilia and Angiogenesis in a Mouse Model of Eosinophilic Esophagitis," J. Pediatr. Gastroenterol. Nutr. 53(4):409-416.
Ruhno, J. et al. (1990). "The Increased Number of Epithelial Mast Cells in Nasal Polyps and Adjacent Turbinates is not Allergy-Dependent," Allergy 45:370-374.
Ruger, B. et al. (1994). "Human Mast Cells Produce Type VIII Collagen in vivo," Int. J. Exp. Path. 75:397-404.
Saha, S. et al. (2006). "Eosinophilic Airway Inflammation in COPD," Int. J. Chron. Obstruct. Pulmon Dis. 1(1):39-47.
Scatchard, G. (1949). "The attractions of proteins for small molecules and ions," Annals of the New York Academy of Sciences, Department of Chemistry, Massachusetts Institute of Technology, MA, 51(4)660-672.
Scordamaglia, F. et al. (Feb. 2008). "Perturbations of Natural Killer Cell Regulatory Functions in Respiratory Allergic Diseases," Journal of Allergy and Clinical Immunology 121(2):479-485.
Seibold, J.R. et al. (Nov. 1990). "Dermal Mast Ceil Degranulation in Systemic Sclerosis," Arthritis and Rheumatism 33(11):1702-1709.
Settipane, G.A. (Sep.-Oct. 1996). "Epidemiology of Nasal Polyps," Allergy and Asthma Proceedings 17(5):231-236.
Sheriff, S. et al. (Sep. 1996). "Redefining the Minimal Antigen-Binding Fragment," Nature Struct. Biol. 3(9):733-736.
Shi, J. et al. (2009). "Characterizing T-Cell Phenotypes in Nasal Polyposis in Chinese Patients," Journal of Investigational Allergology and Clinical Immunology 19(4):276-282.

Shields, R.L. et al. (Mar. 2, 2001). "High Resolution Mapping of the Binding Site on Human IgG1 for FcγRI, FcγII, FcγIII, and FcRn and Design of IgG1 Variants With Improved Binding to the FcγR," J. Biol.Chem. 276(9):6591-6604.
Siebenlist, U. et al. (Jun. 1980). "*E. Coli* RNA Polymerase Interacts Homologously With Two Different Promoters," Cell 20(2):269-281.
Siena, S. et al. (Apr. 2, 2010, e-pub. Feb. 8, 2010) "Reduced Incidence of Infusion-Related Reactions in Metastatic Colorectal Cancer During Treatment With Cetuximab Plus Irinotecan With Combined Corticosteroid and Antihistamine Premedication," Cancer 116(7):1827-1837.
Simmons, L.C. et al. (May 1, 2002). "Expression of Full-Length Immunoglobulins in *Escherichia Coli*: Rapid and Efficient Production of Aglycosylaled Antibodies," J. Immunol. Meth. 263(1-2): 133-147.
Sims, M.J. et al. (Aug. 15, 1993). "A Humanized CD18 Antibody Can Block Function Without Cell Destruction," J. Immunol. 151(4):2296-2308.
Song, D.J. et al. (2009). "Anti-Siglec-F Antibody Reduces Allergen-Induced Eosinophilic Inflammation and Airway Remodeling," The Journal of Immunology, 183(8):5333-5341.
Song, D.J. et al. (Apr. 2009). "Anti-Siglec-F antibody inhibits oral egg allergen induced intestinal eosinophilic inflammation in a mouse model," Clin. Immunol. 131(1):157-169.
Spiess, C. et al. (Sep. 2013). "Development of a Human IgG4 Bispecific Antibody for Dual Targeting of Interleukin-4 (IL-4) and Interleukin-13 (IL-13) Cytokines," The Journal of Biological Chemistry 288(37):26583-26593.
Spronsen, E.V et al. (2008). "Evidence-Based Recommendations Regarding the Differential Diagnosis and Assessment of Nasal Congestion: Using the New GRADE System," Allery 63:820-833.
Steinke, J.W. et al. (2012). "Interleukin-4 in the Generation of the AERD Phenotype: Implications for Molecular Mechanisms Driving Therapeutic Benefit of Aspirin Desensitization," Journal of Allergy 2012(182090):1-9.
Steinke, J.W. et al. (Oct. 2013). "Prominent Role of IFN-γ in Patients with Aspirin-Exacerbated Respiratory Disease," Journal of Allergy and Clinical Immunology 132(4):856-865.
Stevenson, D.D. et al. (2003). "Pathogenesis of Aspirin-Exacerbated Respiratory Disease," Clinical Reviews in Allergy and Immunology 24:169-187.
Stevenson, D.D. et al. (Oct. 2006). "Clinical and Pathologic Perspective on Aspirin Sensitivity and Asthma," The Journal of Allergy and Clinical Immunology 118(4):773-786.
Suresh, M.R. et al. (1986). "Bispecific Monoclonal Antibodies From Hybrid Hybridomas," Methods in Enzymology 121:210-228, 19 pages.
Szczeklik, A. (2010). "Aspirin-Induced Asthma: A Tribute to John Vane as a Source of Inspiration," Pharmacological Reports 62:526-529.
Szczeklik, A. et al. (2009). "Hypersensitivity to Aspirin and Nonsteroidal Anti-Inflammatory Drugs," Middleton's Allergy, 7th Edition, pp. 1227-1243.
Takeno, S. et al. (2012). "What is the Difference Between Paranasal Sinus Bronchial Syndrome and Asthma?," Pathology and Treatment of Chronic Sinusitis Associated With Asthma 143:45-53, with English Translation 33 pages total.
Tanaka, S. et al. (Jun. 15, 2012). "Development of Mature and Functional Human Myeloid subsets in HSC Engrafted NOD/SCID/IL2rγKO Mice," The Journal of Immunology 188(12):6145-6155.
Tashiro, F. et al. (1983). "Zearalenone Reductase from Rat Liver," Journal of Biochemistry 93(6):1557-1566.
Territo, M. (2016). "Eosinophilic Disorders," located at http://www.merckmanuals.com/home/blood-disorders/white-blood-cell-disorders/eosinophilic-disorders last visited on Aug. 23, 2016, 4 pages.
Traunecker, A. et al. (1991). "Bispecific Single Chain Molecules (Janusins) Target Cytotoxic Lymphocytes on HIV Infected Cells," EMBO J. 10(12):3655-3659.
Urlaub, G. et al. (Jul. 1980). "Isolation of Chinese hamster cell mutants deficient in dihydrofolate reductase activity," Proc. Natl. Acad. Sci. USA 77(7):4216-4220.
Usmani, S. Z. et al. (2016) "Open-Label, Multicenter. Dose Escalation Phase 1b Study to Assess the Subcutaneous Delivery of

(56) References Cited

OTHER PUBLICATIONS

Daratumumab in Patients (pts) With Relapsed or Refractory Multiple Myeloma (PAVO)," Blood 128(22) Abstract No. 1149, 7 pages.

Vajdos, F. et al. (2002) "Comprehensive Functional Maps of the Antigen Binding Site of an Anti-ErbB2 Antibody Obtained with Shotgun Scanning Mutagenesis," J. Mol. Biol. 320:415-428.

Valent, P. (2006). "Diagnostic Evaluation and Classification of Mastocytosis," Immunol Allergy Clin North Am 26:515-534.

Valent, P. et al. (2007). "Standards and Standardization in Mastocytosis: Consensus Statements on Diagnostics, Treatment Recommendations and Response Criteria," European Journal of Clinical Investigation 37:435-453.

Valent, P. et al. (2014). "Proposed Diagnostic Algorithm for Patients With Suspected Mastocytosis: A Proposal of the European Competence Network on Mastocytosis," European Journal of Allergy and Clinical Immunology 69:1267-1274.

Van Veen, I.H. et al. (Sep. 2009). "Consistency of Sputum Eosinophilia in Difficult-to-Treat Asthma: A 5-year Follow-Up Study," The Journal of Allergy and Clinical Immunology 124(3):615-617.

Vaswani, S.K. et al. (Aug. 1998). "Humanized Antibodies as Potential Therapeutic Drugs," Ann. Allergy, Asthma & Immunol. 81:105-116.

Verhoeyen, M. et al. (Mar. 25, 1988). "Reshaping Human Antibodies: Grafting An Antilysozyme Activity," Science 239(4857):1534-1536.

Verstovsek, S. "Advanced Systemic Mastocytosis: The Impact of KITMutations in Diagnosis, Treatment and Progression," European Journal of Haematology 90:89-98.

Villar, J. et al. (Apr. 2015). "Tryptase is Involved in the Development of Early Ventilator-Induced Pulmonary Fibrosis in Sepsis-Induced Lung Injury," Critical Care 19(138)1-9.

Wechsler, M.E. et al. (Sep. 2012). "Novel Targeted Therapies for Eosinophilic Disorders," Journal of Allergy and Clinical Immunology 130(3)563-571.

Xu, D. et al. (Feb. 25, 2000). "In Vitro Characterization of Five Humanized OKT3 Effector Function Variant Antibodies," Cellular Immunology 200(1):16-26.

Xu, J.L. et al. (Jul. 2000). "Diversity in the CDR3 Region of VH Is Sufficient for Most Antibody Specificities," Immunity 13:37-45.

Yamane-Ohnuki, N. et al. (2004, e-pub. Aug. 6, 2004). "Establishment of FUT8 Knockout Chinese hamster Ovary Cells: An Ideal Host Cell Line for Producing Completely Defucosylated Antibodies With Enhances Antibody-Dependent Cellular Cytotoxicity," Biotech. Bioeng. 87:614-622.

Yaniv, J.M. (May 6, 1982). "Enhancing Elements for Activation of Eukaryotic Promoters," Nature 297:17-18.

Yansura, D.G. et al. (1992). "Nucleotide Sequence Selection for Increased Expression of Heterologous Genes in *Escherichia coli*," Methods: A Companion to Methods in Enzymol 4:151-158.

Yokoi, H. et al. (Feb. 2008). "Inhibition of Fceri-Dependent Mediator Release and Calcium Flux from Human Mast Cells by Sialic Acid-Binding Immunoglobulin-Like Lectin 8 Engagement," Journal of Allergy and Clinical Immunology 121(2):499-505.

Youngblood B, et al. (May 2018). "AK002, A First-In-Class Humanized, Non-Fucosylated IgG1 Siglec-8 Antibody, Selectively Depletes Blood and Tissue Eosinophils," Gastroenterology 154(6)(Supp. Supplement 1):S-1358. Abstract No. 352.

Youngblood B, et ai. (May 2018). "Anti-Siglec-8 Antibody Reduces Eosinophil and Mast Cell Infiltration in a Mouse Model of Eosinophilic Gastritis: A Novel Therapeutic Approach for Eosinophilic Gastrointestinal Diseases," Gastroenterology 154(6)(Supp. Supplement 1):S-1358. Abstract No. 353.

Youngblood, B.A. et al. (2019). "Siglec-8 Antibody Reduces Eosinophils and Mast Cells in a Transgenic Mouse Model of Eosinophilic Gastroenteritis," JCI Insight 4(19):e126219, pp. 1-15.

Zapata, G. et al. (1995). "Engineering Linear F(ab')2 Fragments For Efficient Production In *Escherichia coli* And Enhanced Antiproliferative Activity," Protein Engineering 8(10):1057-1062.

Zimmerman, N. et al. (Sep. 2008). "Siglec-F antibody administration to mice selectively reduces blood and tissue eosinophils," Allergy 63(9):1156-1163.

Extended European Search Report and European Search Opinion dated Jan. 22, 2021, for European Patent Application No. 18794216.4, filed on Nov. 15, 2019, 8 pages.

\* cited by examiner

METHODS AND COMPOSITIONS FOR TREATING PERENNIAL ALLERGIC CONJUNCTIVITIS AND KERATOCONJUNCTIVITIS

CROSS-REFERENCE TO RELATED APPLICATIONS

This application is a national stage application under 35 U.S.C. § 371 of International Application No. PCT/US2018/031226, filed May 4, 2018, which claims priority to U.S. Provisional Application Ser. No. 62/502,479, filed May 5, 2017, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701712000700SEQLIST.TXT, date recorded: Oct. 29, 2019, size: 115 KB).

FIELD OF THE INVENTION

The present disclosure relates to methods for treating an allergic ocular disease (e.g., allergic conjunctivitis, keratoconjunctivitis, or giant papillary conjunctivitis) by administration of antibodies that bind to human Siglec-8 and compositions comprising said antibodies.

BACKGROUND

Allergic ocular diseases represent some of the most common ocular diseases. The number of people afflicted with allergic ocular diseases has risen in the last decades and is now thought to affect at least 15-20% of the population (La Rosa, M. et al. (2013) *Ital. J. Pediair.* 39:18). Symptoms range in severity from irritation, redness, and swelling of the conjunctiva to cataracts and vision loss.

Allergic ocular diseases encompass a number of specific clinical entities with different mechanisms of action. IgE- and non-IgE-mediated mechanisms are thought to be involved, as are multiple cytokines, chemokines, and signaling pathways (La Rosa. M. et al. (2013) *Ital. J. Pediair.* 39:18). Mast cell hyperplasia and the presence of eosinophils have been observed in some forms of allergic ocular disease, such as atopic keratoconjunctivitis (Morgan, S. J. et al. (1991) *Eye* 5:729-735), which can lead to the development of cataracts and vision loss.

There remains a need for novel therapeutic approaches that target the inflammation underlying allergic ocular diseases.

All references cited herein, including patent applications, patent publications, and scientific literature, are herein incorporated by reference in their entirety, as if each individual reference were specifically and individually indicated to be incorporated by reference.

BRIEF SUMMARY

To meet this and other needs, the present disclosure relates, inter alia, to methods of treating or preventing an allergic ocular disease (e.g., allergic conjunctivitis, keratoconjunctivitis, or giant papillary conjunctivitis) by administration of antibodies that bind to human Siglec-8 and/or compositions comprising said antibodies.

Accordingly, certain aspects of the present disclosure relate to methods for treating or preventing an allergic ocular disease in an individual comprising administering to the individual an effective amount of an antibody that binds to human Siglec-8.

Other aspects of the present disclosure relate to methods for treating or preventing an allergic ocular disease in an individual comprising administering to the individual an effective amount of a composition comprising an antibody that binds to human Siglec-8.

In some embodiments, the individual has allergic conjunctivitis. In some embodiments, the individual has seasonal allergic conjunctivitis. In some embodiments, the individual has perennial allergic conjunctivitis. In some embodiments, the individual has atopic keratoconjunctivitis. In some embodiments, the individual has vernal keratoconjunctivitis. In some embodiments, the individual has giant papillary conjunctivitis. In some embodiments, the individual uses contact lenses. In some embodiments, the individual has increased inflammation in at least a portion of the conjunctiva, as compared to an individual without an allergic ocular disease. In some embodiments, the individual has an increased number of mast cells, neutrophils, eosinophils, and/or lymphocytes in at least a portion of the conjunctiva, as compared to an individual without an allergic ocular disease. In some embodiments, a conjunctival scraping obtained from the individual comprises eosinophils. In some embodiments, a serum or tear sample obtained from the individual has increased IgE, as compared to an individual without an allergic ocular disease. In some embodiments, an epicutaneous or intracutaneous allergy test administered to the individual using an allergen results in an allergic response. In some embodiments, one or more symptom(s) in the individual are reduced as compared to a baseline level before administration of the composition or antibody. In some embodiments, one or more of conjunctival itching, conjunctival redness, conjunctival swelling, ocular discharge, ulceration, tearing, lid hypertrophy, crusting, symblepharon, periocular eczema, madarosis, photophobia, keratitis, giant papillae, and cataracts in the individual are reduced as compared to a baseline level before administration of the composition or antibody. In some embodiments, the composition or antibody is administered by intravenous infusion. In some embodiments, the composition or antibody is administered by subcutaneous injection.

In some embodiments of the methods described herein (e.g., supra), the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence of SEQ ID NO:6; and/or a light chain variable region comprising the amino acid sequence selected from SEQ ID NOs: 16 or 21. In some embodiments, the antibody comprises a heavy chain Fc region comprising a human IgG Fc region. In some embodiments, the human IgG Fc region comprises a human IgG1. In some embodiments, the human IgG Fc region comprises a human IgG4. In some embodiments, the antibody comprises a heavy chain comprising the amino acid sequence of SEQ ID NO:75; and/or a light chain comprising the amino acid sequence selected from SEQ ID NOs: 76 or 77. In some embodiments, the antibody comprises a heavy chain variable region and a light chain variable region, wherein the heavy chain variable region comprises (i) HVR-H comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In some embodiments, the antibody comprises a heavy chain variable region comprising the amino acid sequence selected from SEQ ID NOs: 11-14; and/or a light chain variable region comprising the amino acid sequence selected from SEQ ID NOs:23-24. In some embodiments, the antibody comprises a heavy chain variable region comprising the amino acid sequence selected from SEQ ID NOs:2-14; and/or a light chain variable region comprising the amino acid sequence selected from SEQ ID NOs: 16-24. In some embodiments, the antibody comprises a heavy chain variable region comprising the amino acid sequence selected from SEQ ID NOs:2-10; and/or a light chain variable region comprising the amino acid sequence selected from SEQ ID NOs: 16-22. In some embodiments, the antibody comprises: (a) heavy chain variable region comprising: (1) an HC-FR1 comprising the amino acid sequence selected from SEQ ID NOs:26-29; (2) an HVR-H1 comprising the amino acid sequence of SEQ ID NO:61; (3) an HC-FR2 comprising the amino acid sequence selected from SEQ ID NOs:31-36; (4) an HVR-H2 comprising the amino acid sequence of SEQ ID NO:62; (5) an HC-FR3 comprising the amino acid sequence selected from SEQ ID NOs:38-43; (6) an HVR-H3 comprising the amino acid sequence of SEQ ID NO:63; and (7) an HC-FR4 comprising the amino acid sequence selected from SEQ ID NOs:45-46, and/or (b) a light chain variable region comprising: (1) an LC-FR1 comprising the amino acid sequence selected from SEQ ID NOs:48-49; (2) an HVR-L1 comprising the amino acid sequence of SEQ ID NO:64; (3) an LC-FR2 comprising the amino acid sequence selected from SEQ ID NOs:51-53; (4) an HVR-L2 comprising the amino acid sequence of SEQ ID NO:65; (5) an LC-FR3 comprising the amino acid sequence selected from SEQ ID NOs:55-58; (6) an HVR-L3 comprising the amino acid sequence of SEQ ID NO:66; and (7) an LC-FR4 comprising the amino acid sequence of SEQ ID NO:60. In some embodiments, the antibody comprises: (a) heavy chain variable region comprising: (1) an HC-FR1 comprising the amino acid sequence of SEQ ID NO:26; (2) an HVR-H1 comprising the amino acid sequence of SEQ ID NO:61; (3) an HC-FR2 comprising the amino acid sequence of SEQ ID NO:34; (4) an HVR-H2 comprising the amino acid sequence of SEQ ID NO:62; (5) an HC-FR3 comprising the amino acid sequence of SEQ ID NO:38; (6) an HVR-H3 comprising the amino acid sequence of SEQ ID NO:63; and (7) an HC-FR4 comprising the amino acid sequence of SEQ ID NOs:45; and/or (b) a light chain variable region comprising: (1) an LC-FR1 comprising the amino acid sequence of SEQ ID NO:48, (2) an HVR-L1 comprising the amino acid sequence of SEQ ID NO:64; (3) an LC-FR2 comprising the amino acid sequence of SEQ ID NO:51; (4) an HVR-L2 comprising the amino acid sequence of SEQ ID NO:65; (5) an LC-FR3 comprising the amino acid sequence of SEQ ID NO:55; (6) an HVR-L3 comprising the amino acid sequence of SEQ ID NO:66; and (7) an LC-FR4 comprising the amino acid sequence of SEQ ID NO:60. In some embodiments, the antibody comprises: (a) heavy chain variable region comprising: (1) an HC-FR1 comprising the amino acid sequence of SEQ ID NO:26 (2) an HVR-H1 comprising the amino acid sequence of SEQ ID NO:61; (3) an HC-FR2 comprising the amino acid sequence of SEQ ID NO:34; (4) an HVR-H2 comprising the amino acid sequence of SEQ ID NO:62; (5) an HC-FR3 comprising the amino acid sequence of SEQ ID NO:38; (6) an HVR-H3 comprising the amino acid sequence of SEQ ID NO:63; and (7) an HC-FR4 comprising the amino acid sequence of SEQ ID NOs:45; and/or (b) a light chain variable region comprising: (1) an LC-FR1 comprising the amino acid sequence of SEQ ID NO:48; (2) an HVR-L1 comprising the amino acid sequence of SEQ ID NO:64; (3) an LC-FR2 comprising the amino acid sequence of SEQ ID NO:51; (4) an HVR-L2 comprising the amino acid sequence of SEQ ID NO:65, (5) an LC-FR3 comprising the amino acid sequence of SEQ ID NO:58; (6) an HVR-L3 comprising the amino acid sequence of SEQ ID NO:66; and (7) an LC-FR4 comprising the amino acid sequence of SEQ ID NO:60. In some embodiments, the antibody comprises: a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO: 100, and (iii) HVR-L3 comprising the amino acid sequence of SEQ ID NO: 103; a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO: 101, and (iii) HVR-L3 comprising the amino acid sequence of SEQ ID NO: 104; or a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO: 102, and (iii) HVR-L3 comprising the amino acid sequence of SEQ ID NO: 105. In some embodiments, the antibody comprises: a heavy chain variable region comprising the amino acid sequence of SEQ ID NO: 106; and/or a light chain variable region comprising the amino acid sequence of SEQ ID NO: 109; a heavy chain variable region comprising the amino acid sequence of SEQ ID NO: 107: and/or a light chain variable region comprising the amino acid sequence of SEQ ID NO:110; or a heavy chain variable region comprising the amino acid sequence of SEQ ID NO: 108; and/or a light chain variable region comprising the amino acid sequence of SEQ ID NO: 111. In some embodiments, the antibody is a monoclonal antibody. In some embodiments, the antibody is an IgG1 antibody. In some embodiments, the antibody has been engineered to improve antibody-dependent cell-mediated cytotoxicity (ADCC) activity. In some embodiments, the antibody comprises at least one amino acid substitution in the Fc region that improves ADCC activity. In some embodiments, at least one or two of the heavy chains of the antibody is non-fucosylated. In some embodiments, the antibody is a human antibody, a humanized antibody or a chimeric antibody. In some embodiments, the antibody comprises an antibody fragment selected from the group consisting of Fab, Fab'-SH, Fv, scFv, and (Fab')$_2$ fragments.

In some embodiments of the methods described herein (e.g., supra), the antibody comprises a Fc region and N-glycoside-linked carbohydrate chains linked to the Fc region, wherein less than 50% of the N-glycoside-linked carbohydrate chains of the antibody in the composition contain a fucose residue. In some embodiments, substantially none of the N-glycoside-linked carbohydrate chains of the antibody in the composition contain a fucose residue. In some embodiments, the antibody binds to a human Siglec-8 and a non-human primate Siglec-8. In some embodiments, the non-human primate is a baboon. In some embodiments, the antibody binds to an epitope in Domain 1 of human Siglec-8, wherein Domain 1 comprises the amino acid sequence of SEQ ID NO:112. In some embodiments, the antibody binds to an epitope in Domain 3 of human Siglec-8, wherein Domain 3 comprises the amino acid sequence of SEQ ID NO:114. In some embodiments, the antibody binds to the same epitope as antibody 4F11. In some embodiments, the antibody binds to an epitope in Domain 2 or Domain 3 of human Siglec-8. In some embodiments, Domain 2 comprises the amino acid sequence of SEQ ID NO: 113. In some embodiments, the antibody binds to the same epitope as antibody 1C3. In some embodiments, Domain 3 comprises the amino acid sequence of SEQ ID NO: 114. In some embodiments, the antibody binds to the same epitope as antibody 1H10. In some embodiments, the antibody binds to an epitope in Domain 1 of human Siglec-8 and competes with antibody 4F11 for binding to Siglec-8. In some embodiments, the antibody does not compete with antibody 2E2 for binding to Siglec-8. In some embodiments, the antibody is not antibody 2E2. In some embodiments, Domain 1 comprises the amino acid sequence of SEQ ID NO: 112. In some embodiments, the antibody comprises a heavy chain Fc region comprising a human IgG Fc region. In some embodiments, the human IgG Fc region comprises a human IgG1 Fc region. In some embodiments, the human IgG1 Fc region is non-fucosylated. In some embodiments, the human IgG Fc region comprises a human IgG4 Fc region. In some embodiments, the human IgG4 Fc region comprises the amino acid substitution S228P, wherein the amino acid residues are numbered according to the EU index as in Kabat. In some embodiments, the antibody depletes blood eosinophils and/or inhibits mast cell activation.

In some embodiments of the methods described herein (e.g., supra), the composition or antibody is administered in combination with one or more additional therapeutic agent(s) for treating or preventing an allergic ocular disease. In some embodiments, the one or more additional therapeutic agent(s) are selected from the group consisting of a corticosteroid, antihistamine, ketotifen, azelastine, epinastine, bepostatine, cyclosporine, and a non-steroidal anti-inflammatory agent (NSAID).

In some embodiments of the methods described herein (e.g., supra), the individual is a human. In some embodiments, the antibody is in a pharmaceutical composition comprising the antibody and a pharmaceutically acceptable carrier.

Other aspects of the present disclosure relate to an article of manufacture comprising a medicament comprising a composition comprising an antibody that binds to human Siglec-8 and a package insert comprising instructions for administration of the medicament in an individual in need thereof according to any of the above embodiments.

It is to be understood that one, some, or all of the properties of the various embodiments described herein may be combined to form other embodiments of the present disclosure. These and other aspects of the present disclosure will become apparent to one of skill in the art. These and other embodiments of the present disclosure are further described by the detailed description that follows.

DETAILED DESCRIPTION

I. Definitions

It is to be understood that the present disclosure is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising," "consisting," and "consisting essentially of" aspects and embodiments.

The term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules), as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for p and F isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I.

Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in the present disclosure. Common allotypic variants in human populations are those designated by the letters a, f, n, z.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al, *Protein Eng.* 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the present disclosure comprise a portion of an intact antibody, generally including the antigen binding or variable region of the intact antibody or the Fv region of an antibody which retains or has modified FcR binding capability. Examples of antibody fragments include linear antibody, single-chain antibody molecules and multispecific antibodies formed from antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al. *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used as a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. In some embodiments, the number of these amino acid substitutions in the FR are no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332: 323-329 (1988); and Presta, *Curr. Op. Struct. Biol.* 2:593-596 (1992). See also, for example, Vaswani and Hamilton, *Ann. Allergy Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409. In some embodiments, humanized antibodies are directed against a single antigenic site. In some embodiments, humanized antibodies are directed against multiple antigenic sites. An alternative humanization method is described in U.S. Pat. No. 7,981,843 and U.S. Patent Application Publication No. 2006/0134098.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000). Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest.* 5$^{th}$ Ed. Public Health Service, National Institute of Health, Bethesda, Md. (1991)). Chothia HVRs refer instead to the location of the structural loops (Chothia and Lesk *J. Mol. Biol.* 196:901-917 (1987)). The "contact" HVRs are based on an analysis of the available complex crystal structures. The residues from each of these HVRs are noted below.

| Loop | Kabat | Chothia | Contact |
|---|---|---|---|
| L1 | L24-L34 | L26-L34 | L30-L36 |
| L2 | L50-L56 | L50-L56 | L46-L55 |
| L3 | L89-L97 | L91-L96 | L89-L96 |
| H1 | H31-H35B | H26-H32 | H30-H35B (Kabat Numbering) |
| H1 | H31-H35 | H26-H32 | H30-H35 (Chothia Numbering) |
| H2 | H50-H65 | H53-H56 | H47-H58 |
| H3 | H95-H102 | H95-H102 | H93-H101 |

Unless otherwise indicated, the variable-domain residues (HVR residues and framework region residues) are numbered according to Kabat et al., supra.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An antibody that "binds to", "specifically binds to" or is "specific for" a particular a polypeptide or an epitope on a particular polypeptide is one that binds to that particular polypeptide or epitope on a particular polypeptide without substantially binding to any other polypeptide or polypeptide epitope. In some embodiments, binding of an anti-Siglec-8 antibody described herein (e.g., an antibody that binds to human Siglec-8) to an unrelated non-Siglec-8 polypeptide is less than about 10% of the antibody binding to Siglec-8 as measured by methods known in the art (e.g., enzyme-linked immunosorbent assay (ELISA)). In some embodiments, an antibody that binds to a Siglec-8 (e.g., an antibody that binds to human Siglec-8) has a dissociation constant (Kd) of ≤1 µM, ≤100 nM, ≤10 nM, ≤2 nM, ≤1 nM, ≤0.7 nM, ≤0.6 nM, ≤0.5 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

The term "anti-Siglec-8 antibody" or "an antibody that binds to human Siglec-8" refers to an antibody that binds to a polypeptide or an epitope of human Siglec-8 without substantially binding to any other polypeptide or epitope of an unrelated non-Siglec-8 polypeptide.

The term "Siglec-8" as used herein refers to a human Siglec-8 protein. The term also includes naturally occurring variants of Siglec-8, including splice variants or allelic variants. The amino acid sequence of an exemplary human Siglec-8 is shown in SEQ ID NO:72. The amino acid sequence of another exemplary human Siglec-8 is shown in SEQ ID NO:73. In some embodiments, a human Siglec-8 protein comprises the human Siglec-8 extracellular domain fused to an immunoglobulin Fc region. The amino acid sequence of an exemplary human Siglec-8 extracellular domain fused to an immunoglobulin Fc region is shown in SEQ ID NO:74. The amino acid sequence underlined in SEQ ID NO:74 indicates the Fc region of the Siglec-8 Fc fusion protein amino acid sequence.

Human Siglec-8 Amino Acid Sequence
(SEQ ID NO: 72)
GYLLQVQELVTVQEGLCVHVPCSFSYPQDGWTDSDPVHGYWFRAAGDR

PYQDAPVATNNPDREVQAETQGRFQLLGDIWSNDCSLSIRDARKRDKG

SYFFRLERGSMKWSYKSQLNYKTKQLSVFVTALTHRPDILILGTLESG

HSRNLTCSVPWACKQGTPPMISWIGASVSSPGPTTARSSVLTLTPKPQ

DHGTSLTCQVTLPGTGVTTTSTVRLDVSYPPWNLTMTVFQGDATASTA

LGNGSSLSVLEGQSLRLVCAVNSNPPARLSWTRGSLTLCPSRSSNPGL

LELPRVHVRDEGEFTCRAQNAQGSQHISLSLSLQNEGTGTSRPVSQVT

LAAVGGAGATALAFLSFCIIFIIVRSCRKKSARPAAGVGDTGMEDAKA

IRGSASQGPLTESWKDGNPLKKPPPAVAPSSGEEGELHYATLSFHKVK

PQDPQGQEATDSEYSEIKIHKRETAETQACLRNHNPSSKEVRG

Human Siglec-8 Amino Acid Sequence
(SEQ ID NO: 73)
GYLLQVQELVTVQEGLCVHVPCSFSYPQDGWTDSDPVHGYWFRAGDRP

YQDAPVATNNPDREVQAETQGRFQLLGDIWSNDCSLSIRDARKRDKGS

YFFRLERGSMKWSYKSQLNYKTKQLSVFVTALTHRPDILILGTLESGH

PRNLTCSVPWACKQGTPPMISWIGASVSSPGPTTARSSVLTLTPKPQD

HGTSLTCQVTLPGTGVTTTSTVRLDVSYPPWNLTMTVFQGDATASTAL

GNGSSLSVLEGQSLRLVCAVNSNPPARLSWTRGSLTLCPSRSSNPGLL

ELPRVHVRDEGEFTCRAQNAQGSQHISLSLSLQNEGTGTSRPVSQVTL

AAVGGAGATALAFLSFCIIFIIVRSCRKKSARPAAGVGDTGMEDAKAI

RGSASQGPLTESWKDGNPLKKPPPAVAPSSGEEGELHYATLSFHKVKP

QDPQGQEATDSEYSEIKIHKRETAETQACLRNHNPSSKEVRG

Siglec-8 Fc Fusion Protein Amino Acid Sequence
(SEQ ID NO: 74)
GYLLQVQELVTVQEGLCVHVPCSFSYPQDGWTDSDPVHGYWFRAGDRP

YQDAPVATNNPDREVQAETQGRFQLLGDIWSNDCSLSIRDARKRDKGS

YFFRLERGSMKWSYKSQLNYKTKQLSVFVTALTHRPDILILGTLESGH

-continued

```
SRNLTCSVPWACKQGTPPMISWIGASVSSPGPTTARSSVLTLTPKPQD

HGTSLTCQVTLPGTGVTTTSTVRLDVSYPPWNLTMTVFQGDATASTAL

GNGSSLSVLEGQSLRLVCAVNSNPPARLSWTRGSLTLCPSRSSNPGLL

ELPRVHVRDEGEFTCRAQNAQGSQHISLSLSLQNEGTGTSRPVSQVTL

AAVGGIEGRSDKTHTCPPCPAPELLGGPSVFLFPPKPKDTLMISRTPE

VTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPS

REEMTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

Antibodies that "induce apoptosis" or are "apoptotic" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies). For example, the apoptotic activity of the anti-Siglec-8 antibodies (e.g., an antibody that binds to human Siglec-8) of the present disclosure can be shown by staining cells with annexin V.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII. Fc expression on hematopoietic cells is summarized in Table 3 on page 464 of Ravetch and Kinet, *Annu. Rev. Immunol.* 9: 457-92 (1991). In some embodiments, an anti-Siglec-8 antibody (e.g., an antibody that binds to human Siglec-8) described herein enhances ADCC. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., *PNAS USA* 95:652-656 (1998). Other Fc variants that alter ADCC activity and other antibody properties include those disclosed by Ghetie et al., Nat Biotech. 15:637-40, 1997; Duncan et al, Nature 332:563-564, 1988; Lund et al., J. Immunol 147:2657-2662, 1991; Lund et al, Mol Immunol 29:53-59, 1992; Alegre et al, Transplantation 57:1537-1543, 1994; Hutchins et al., Proc Natl Acad Sci USA 92:11980-11984, 1995; Jefferis et al, Immunol Lett. 44:111-117, 1995; Lund et al., FASEB J 9:115-119, 1995; Jefferis et al, Immunol Lett 54:101-104, 1996; Lund et al, J Immunol 157:4963-4969, 1996; Armour et al., Eur J Immunol 29:2613-2624, 1999; Idusogie et al, J Immunol 164:4178-4184, 200; Reddy et al, J Immunol 164:1925-1933, 2000; Xu et al., Cell Immunol 200:16-26, 2000; Idusogie et al, J Immunol 166:2571-2575, 2001; Shields et al., J Biol Chem 276:6591-6604, 2001; Jefferis et al, Immunol Lett 82:57-65, 2002; Presta et al., Biochem Soc Trans 30:487-490, 2002; Lazar et al., Proc. Natl. Acad. Sci. USA 103:4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present disclosure include human IgG1, IgG2, IgG3 and IgG4. A single amino acid substitution (S228P according to Kabat numbering; designated IgG4Pro) may be introduced to abolish the heterogeneity observed in recombinant IgG4 antibody. See Angal, S. et al. (1993) Mol Immunol 30, 105-108.

"Non-fucosylated" or "fucose-deficient" antibody refers to a glycosylation antibody variant comprising an Fc region wherein a carbohydrate structure attached to the Fc region has reduced fucose or lacks fucose. In some embodiments, an antibody with reduced fucose or lacking fucose has improved ADCC function. Non-fucosylated or fucose-deficient antibodies have reduced fucose relative to the amount of fucose on the same antibody produced in a cell line. In some embodiments, a non-fucosylated or fucose-deficient antibody composition contemplated herein is a composition wherein less than about 50% of the N-linked glycans attached to the Fc region of the antibodies in the composition comprise fucose.

The terms "fucosylation" or "fucosylated" refers to the presence of fucose residues within the oligosaccharides attached to the peptide backbone of an antibody. Specifically, a fucosylated antibody comprises α (1,6)-linked fucose at the innermost N-acetylglucosamine (GlcNAc) residue in one or both of the N-linked oligosaccharides attached to the antibody Fc region, e.g. at position Asn 297 of the human IgG1 Fc domain (EU numbering of Fc region residues). Asn297 may also be located about ±3 amino acids upstream or downstream of position 297, i.e. between positions 294 and 300, due to minor sequence variations in immunoglobulins.

The "degree of fucosylation" is the percentage of fucosylated oligosaccharides relative to all oligosaccharides identified by methods known in the art e.g., in an N-glycosidase F treated antibody composition assessed by matrix-assisted laser desorption-ionization time-of-flight mass spectrometry (MALDI-TOF MS). In a composition of a "fully fucoslated antibody" essentially all oligosaccharides comprise fucose residues, i.e. are fucosylated. In some embodiments, a composition of a fully fucosylated antibody has a degree of fucosylation of at least about 90%. Accordingly, an individual antibody in such a composition typically comprises fucose residues in each of the two N-linked oligosaccharides in the Fc region. Conversely, in a composition of a "fully non-fucosylated" antibody essentially none of the oligosaccharides are fucosylated, and an individual antibody in such a composition does not contain fucose residues in either of the two N-linked oligosaccharides in the Fc region. In some embodiments, a composition of a fully non-fucosylated antibody has a degree of fucosylation of less than about 10%. In a composition of a "partially fucosylated antibody" only part of the oligosaccharides comprise fucose. An individual antibody in such a composition can comprise fucose residues in none, one or both of the N-linked oligosaccharides in the Fc region, provided that the composition does not comprise essentially all individual antibodies that lack fucose residues in the N-linked oligosaccharides in the Fc region, nor essentially all individual antibodies that contain fucose residues in both of the N-linked oligosaccharides in the Fc region. In one embodiment, a composition of a partially fucosylated antibody has a degree of fucosylation of about 10% to about 80% (e.g., about 50% to about 80%, about 60% to about 80%, or about 70% to about 80%).

"Binding affinity" as used herein refers to the strength of the non-covalent interactions between a single binding site of a molecule (e.g., an antibody) and its binding partner (e.g., an antigen). In some embodiments, the binding affinity of an antibody for a Siglec-8 (which may be a dimer, such as the Siglec-8-Fc fusion protein described herein) can generally be represented by a dissociation constant (Kd). Affinity can be measured by common methods known in the art, including those described herein.

"Binding avidity" as used herein refers to the binding strength of multiple binding sites of a molecule (e.g., an antibody) and its binding partner (e.g., an antigen).

An "isolated" nucleic acid molecule encoding the antibodies herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "pharmaceutical formulation" refers to a preparation that is in such form as to permit the biological activity of the active ingredient to be effective, and that contains no additional components that are unacceptably toxic to an individual to which the formulation would be administered. Such formulations are sterile.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "treatment" or "treating" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease (e.g., an allergic ocular disease) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

As used herein, "in conjunction with" or "in combination with" refers to administration of one treatment modality in addition to another treatment modality. As such, "in conjunction with" or "in combination with" refers to administration of one treatment modality before, during or after administration of the other treatment modality to the individual.

As used herein, the term "prevention" or "preventing" includes providing prophylaxis with respect to occurrence or recurrence of a disease in an individual. An individual may be predisposed to a disease, susceptible to a disease, or at risk of developing a disease, but has not yet been diagnosed with the disease. In some embodiments, anti-Siglec-8 antibodies (e.g., an antibody that binds to human Siglec-8) described herein are used to delay development of a disease (e.g., an allergic ocular disease).

As used herein, an individual "at risk" of developing a disease (e.g., an allergic ocular disease) may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of the disease (e.g., an allergic ocular disease), as known in the art. An individual having one or more of these risk factors has a higher probability of developing the disease than an individual without one or more of these risk factors.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum concentration required to effect a measurable improvement of a particular disease. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in individuals prior to or at the earlier stage of disease, the prophylactically effective amount can be less than the therapeutically effective amount.

"Chronic" administration refers to administration of the medicament(s) in a continuous as opposed to acute mode, so as to maintain the initial therapeutic effect (activity) for an extended period of time. "Intermittent" administration is treatment that is not consecutively done without interruption, but rather is cyclic in nature.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is a human.

II. Methods

Provided herein are methods for treating and/or preventing an allergic ocular disease (e.g., allergic conjunctivitis, keratoconjunctivitis, or giant papillary conjunctivitis) in an individual comprising administering to the individual an effective amount of an antibody described herein that binds to human Siglec-8 (e.g., an anti-Siglec-8 antibody) or compositions comprising said antibodies. In some embodiments, the antibody is in a pharmaceutical composition comprising the antibody and a pharmaceutically acceptable carrier. In some embodiments, the individual is a human.

A. Allergic Ocular Diseases

Certain aspects of the present disclosure relate to individuals with an allergic ocular disease (e.g., allergic conjunctivitis, keratoconjunctivitis, or giant papillary conjunctivitis). In some embodiments, the individual has allergic conjunctivitis. In some embodiments, the individual has atopic keratoconjunctivitis. In some embodiments, the individual has vernal keratoconjunctivitis. In some embodiments, the individual has giant papillary conjunctivitis.

In some embodiments, the individual has been diagnosed with allergic conjunctivitis. In some embodiments, the individual is at risk of developing allergic conjunctivitis. Allergic conjunctivitis refers to a number of allergic ocular diseases characterized by a type I hypersensitivity (i.e., IgE-mediated) allergic reaction in the conjunctiva. Both seasonal and perennial forms are known, including seasonal allergic conjunctivitis, perennial allergic conjunctivitis (e.g., atopic conjunctivitis or atopic keratoconjunctivitis), and vernal keratoconjunctivitis.

In some embodiments, the individual has been diagnosed with atopic or vernal keratoconjunctivitis or is at risk of developing atopic or vernal keratoconjunctivitis. Both forms of keratoconjunctivitis are characterized by allergic inflammation of the ocular surface, including itching, redness, swelling, and discharge. Individuals with vernal keratoconjunctivitis typically also present with giant papillae on the upper tarsal conjunctiva, whereas giant papillae may or may not be present in atopic keratoconjunctivitis (La Rosa, M. et al. (2013) *Ital. J. Pediatr.* 39:18). While vernal keratoconjunctivitis is only seen in warm weather, atopic keratoconjunctivitis can be observed with little or no seasonal variation.

In some embodiments, the individual has been diagnosed with giant papillary conjunctivitis or is at risk of developing giant papillary conjunctivitis. Giant papillary conjunctivitis is characterized by papillary hypertrophy (e.g., of the superior tarsal conjunctiva). Often, irritation and IgE production are caused by contact lens usage, e.g., from protein buildup and/or mechanical irritation.

Symptoms of allergic ocular diseases can include, without limitation, conjunctival itching, conjunctival redness, conjunctival swelling, ocular discharge, ulceration (e.g., corneal ulceration), tearing, lid hypertrophy, crusting, symblepharon, periocular eczema, madarosis, photophobia, keratitis, giant papillae, eye pain, foreign body sensation, and cataracts.

The terms "reference" or "reference value" used interchangeably herein can refer to a measurement or characterization of a value or symptom in an individual without an allergic ocular disease (or in a group of such individuals). A "reference value" can be an absolute value; a relative value; a value that has an upper and/or lower limit; a range of values; an average value; a median value; a mean value; or a value as compared to a baseline value. Similarly, a "baseline value" can be an absolute value; a relative value; a value that has an upper and/or lower limit; a range of values; an average value; a median value; a mean value; or a value as compared to a reference value. A reference value can be obtained from one individual, from two different individuals or from a group of individuals (e.g., a group of two, three, four, five or more individuals). In some embodiments, a reference value refers to a standard or benchmark value in the field. In some embodiments, a reference value refers to a value calculated de novo from one or more individuals (e.g., without an allergic ocular disease).

In some embodiments, a conjunctival scraping obtained from the individual comprises eosinophils. Examining a conjunctival scraping for the presence of eosinophils can be used to diagnose an allergic ocular disease (e.g., vernal keratoconjunctivitis, as described in Bonini, S. et al. (2004) *Eye* 18:345-351); however, eosinophilic infiltration may exist in deeper conjunctival tissues that are not accessible to superficial scraping (see Abelson, M. B. et al. (1983) *Arch. Ophthalmol.* 101:555-556).

In some embodiments, a serum sample obtained from the individual has increased IgE, as compared to an individual without an allergic ocular disease. In some embodiments, a tear sample obtained from the individual has increased IgE, as compared to an individual without an allergic ocular disease. Techniques for measuring IgE levels in a tear sample are known in the art; see, e.g., the Allerwatch® immunochromatography test for total tear IgE (Hitachi Chemical Co.). Techniques for measuring IgE levels in a serum sample are also known in the art (e.g., sandwich radioimmunoassay), and normal ranges for mean IgE concentration in a serum sample obtained from patients of various ages have been described (see Homburger H A: Allergic diseases. In Clinical Diagnosis and Management by Laboratory Methods. 21st edition. New York, WB Saunders Company, 2007, pp 961-971).

In some embodiments, an epicutaneous or intracutaneous allergy test administered to the individual using an allergen results in an allergic response. Methods for epicutaneous (e.g., skin prick, scratch, puncture, or patch test) and intracutaneous (e.g., intradermal) allergy testing are known in the art. Typically, a small amount of one or more allergens are introduced into a small area of the skin (e.g., through epicutaneous or intracutaneous routes, such as a needle prick or injection), then monitored by physician for an allergic response (e.g., redness, swelling, itching, wheal formation, etc.). In some embodiments, an allergic response is indicative of an IgE-mediated reaction. For allergic ocular diseases, epicutaneous or intracutaneous allergy testing can be performed for hypersensitivity to airborne allergens, including without limitation dust mites, pet dander, and pollen.

B. Response to Treatment

In some embodiments, administering to an individual as described herein (e.g., an individual having an allergic ocular disease) an effective amount of an antibody described herein that binds to human Siglec-8 (e.g., an anti-Siglec-8 antibody) reduces one or more (e.g., one or more, two or more, three or more, four or more, etc.) symptoms in the individual, as compared to a baseline level before administration of the antibody.

The terms "baseline" or "baseline value" used interchangeably herein can refer to a measurement or characterization of a symptom before the administration of the therapy (e.g., an anti-Siglec-8 antibody) or at the beginning of administration of the therapy. The baseline value can be compared to a reference value in order to determine the reduction or improvement of a symptom of an allergic ocular disease contemplated herein. A reference value and/or baseline value can be obtained from one individual, from two different individuals or from a group of individuals (e.g., a group of two, three, four, five or more individuals).

Response to treatment in individuals with an allergic ocular disease can be assessed by methods known in the art. For example, response to treatment in an individual with an allergic ocular disease (e.g., allergic conjunctivitis, keratoconjunctivitis, or giant papillary conjunctivitis) can be the reduction or improvement of any symptom thereof described herein. Symptoms of allergic ocular disease can include, but are not limited to, conjunctival itching, conjunctival redness, conjunctival swelling, ocular discharge, ulceration, tearing, lid hypertrophy, crusting, symblepharon, periocular eczema, madarosis, photophobia, keratitis, giant papillae, and cataracts. Response to treatment may result in complete remission (CR), partial remission (PR), or a clinical improvement (CI) of an allergic ocular disease (e.g., allergic conjunctivitis, keratoconjunctivitis, or giant papillary conjunctivitis) in an individual.

Techniques for measuring response to treatment for an allergic ocular disease (e.g., allergic conjunctivitis, keratoconjunctivitis, or giant papillary conjunctivitis) are known in the art. For example, techniques for measuring response to treatment can include without limitation a lessening in one or more clinical symptoms (e.g., as described supra), conjunctival scraping (e.g., for detection of eosinophils), and IgE testing in serum and/or tear samples. In some embodiments, an Allergic Conjunctivitis Symptom (ACS) Questionnaire is used to evaluate symptoms associated with an allergic ocular disease (e.g., allergic conjunctivitis, keratoconjunctivitis, or giant papillary conjunctivitis).

C. Administration

For the prevention or treatment of disease, the appropriate dosage of an active agent, will depend on the type of disease to be treated, as defined above, the severity and course of the disease, whether the agent is administered for preventive or therapeutic purposes, previous therapy, the individual's clinical history and response to the agent, and the discretion of the attending physician. The agent is suitably administered to the individual at one time or over a series of treatments. In some embodiments, an interval between administrations of an anti-Siglec-8 antibody (e.g., an antibody that binds to human Siglec-8) described herein is about one month or longer. In some embodiments, the interval between administrations is about two months, about three months, about four months, about five months, about six months or longer. As used herein, an interval between administrations refers to the time period between one administration of the antibody and the next administration of the antibody. As used herein, an interval of about one month includes four weeks. Accordingly, in some embodiments, the interval between administrations is about four weeks, about five weeks, about six weeks, about seven weeks, about eight weeks, about nine weeks, about ten weeks, about eleven weeks, about twelve weeks, about sixteen weeks, about twenty weeks, about twenty four weeks, or longer. In some embodiments, the treatment includes multiple administrations of the antibody, wherein the interval between administrations may vary. For example, the interval between the first administration and the second administration is about one month, and the intervals between the subsequent administrations are about three months. In some embodiments, the interval between the first administration and the second administration is about one month, the interval between the second administration and the third administration is about two months, and the intervals between the subsequent administrations are about three months. In some embodiments, an anti-Siglec-8 antibody described herein (e.g., an antibody that binds to human Siglec-8) is administered at a flat dose. In some embodiments, an anti-Siglec-8 antibody described herein (e.g., an antibody that binds to human Siglec-8) is administered to an individual at a dosage from about 0.1 mg to about 1800 mg per dose. In some embodiments, the anti-Siglec-8 antibody (e.g., an antibody that binds to human Siglec-8) is administered to an individual at a dosage of about any of 0.1 mg, 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, and 1800 mg per dose. In some embodiments, an anti-Siglec-8 antibody described herein (e.g., an antibody that binds to human Siglec-8) is administered to an individual at a dosage from about 150 mg to about 450 mg per dose. In some embodiments, the anti-Siglec-8 antibody (e.g., an antibody that binds to human Siglec-8) is administered to an individual at a dosage of about any of 150 mg, 200 mg, 250 mg, 300 mg, 350 mg, 400 mg, and 450 mg per dose. In some embodiments, an anti-Siglec-8 antibody described herein (e.g., an antibody that binds to human Siglec-8) is administered to an individual at a dosage from about 0.1 mg/kg to about 20 mg/kg per dose. In some embodiments, an anti-Siglec-8 antibody described herein (e.g., an antibody that binds to human Siglec-8) is administered to an individual at a dosage from about 0.01 mg/kg to about 10 mg/kg per dose. In some embodiments, an anti-Siglec-8 antibody described herein (e.g., an antibody that binds to human Siglec-8) is administered to an individual at a dosage from about 0.1 mg/kg to about 10 mg/kg or about 1.0 mg/kg to about 10 mg/kg. In some embodiments, an anti-Siglec-8 antibody described herein is administered to an individual at a dosage of about any of 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, or 10.0 mg/kg. Any of the dosing frequency described above may be used. Any dosing frequency described above may be used in the methods or uses of the compositions described herein. Efficacy of treatment with an antibody described herein (e.g., an antibody that binds to human Siglec-8) can be assessed using any of the methodologies or assays described herein at intervals ranging between every week and every three months. In some embodiments, efficacy of treatment (e.g., reduction or improvement of one or more symptoms) is assessed about every one month, about every two months, about every three months, about every four months, about every five months, about every six months or longer after administration of an antibody that binds to human Siglec-8. In some embodiments, efficacy of treatment (e.g., reduction or improvement of one or more symptoms) is assessed about every one week, about every two weeks, about every three weeks, about every four weeks, about every five weeks, about every six weeks, about every seven weeks, about every eight weeks, about every nine weeks, about every ten weeks, about every eleven weeks, about every twelve weeks, about every sixteen weeks, about every twenty weeks, about every twenty four weeks, or longer.

In certain embodiments, an anti-Siglec-8 antibody described herein (e.g., an antibody that binds to human Siglec-8) is administered to an individual monthly at a dosage of up to 3.0 mg/kg by intravenous infusion. In certain embodiments, an anti-Siglec-8 antibody described herein (e.g., an antibody that binds to human Siglec-8) is administered to an individual monthly at a dosage of up to 3.0 mg/kg by subcutaneous injection. In certain embodiments, an anti-Siglec-8 antibody described herein (e.g., an antibody that binds to human Siglec-8) is administered to an individual every four weeks at a dosage of up to 3.0 mg/kg by intravenous infusion. In certain embodiments, an anti-Siglec-8 antibody described herein (e.g., an antibody that binds to human Siglec-8) is administered to an individual every four weeks at a dosage of up to 3.0 mg/kg by subcutaneous injection.

Antibodies described herein that bind to human Siglec-8 can be used either alone or in combination with other agents in the methods described herein. For instance, an antibody that binds to a human Siglec-8 may be co-administered with one or more (e.g., one or more, two or more, three or more, four or more, etc.) additional therapeutic agents for treating and/or preventing an allergic ocular disease (e.g., allergic conjunctivitis, keratoconjunctivitis, or giant papillary conjunctivitis). Therapeutic agents contemplated herein include, but are not limited to, a corticosteroid (e.g., budesonide, dexamethasone, hydrocortisone, methylprednisolone, prednisolone, or predisone), antihistamine (e.g., levocabastine hydrochloride or olopatadine), ketotifen, azelastine, epinastine, bepostatine, cyclosporine, and a non-steroidal anti-inflammatory agent (NSAID).

Such combination therapies noted above encompass combined administration (where two or more therapeutic agents are included in the same or separate formulations), and separate administration, in which case, administration of the antibody of the present disclosure can occur prior to, simultaneously, and/or following, administration of the one or more additional therapeutic agents. In some embodiments, administration of an anti-Siglec-8 antibody described herein and administration of one or more additional therapeutic agents occur within about one month, about two months, about three months, about four months, about five months or about six months of each other. In some embodiments, administration of an anti-Siglec-8 antibody described herein and administration of one or more additional therapeutic agents occur within about one week, about two weeks or about three weeks of each other. In some embodiments, administration of an anti-Siglec-8 antibody described herein and administration of one or more additional therapeutic agents occur within about one day, about two days, about three days, about four days, about five days, or about six days of each other.

Anti-Siglec8 antibodies and/or one or more additional therapeutic agents may be administered via any suitable route of administration known in the art, including, without limitation, by oral administration, sublingual administration, buccal administration, topical administration, rectal administration, via inhalation, transdermal administration, subcutaneous injection, intradermal injection, intravenous (IV) injection, intra-arterial injection, intramuscular injection, intracardiac injection, intraosseous injection, intraperitoneal injection, transmucosal administration, vaginal administration, intravitreal administration, intra-articular administration, peri-articular administration, local administration, epicutaneous administration, or any combinations thereof.

D. Antibodies

Certain aspects of the present disclosure provide isolated antibodies that bind to a human Siglec-8 (e.g., an agonist antibody that binds to human Siglec-8). In some embodiments, an anti-Siglec-8 antibody described herein has one or more of the following characteristics; (1) binds a human Siglec-8; (2) binds to an extracellular domain of a human Siglec-8; (3) binds a human Siglec-8 with a higher affinity than mouse antibody 2E2 and/or mouse antibody 2C4; (4) binds a human Siglec-8 with a higher avidity than mouse antibody 2E2 and/or mouse antibody 2C4; (5) has a $T_m$ of about 70° C.-72° C. or higher in a thermal shift assay; (6) has a reduced degree of fucosylation or is non-fucosylated; (7) binds a human Siglec-8 expressed on eosinophils and induces apoptosis of eosinophils; (8) binds a human Siglec-8 expressed on mast cells and depletes or reduces the number of mast cells; (9) binds a human Siglec-8 expressed on mast cells and inhibits FcεRI-dependent activities of mast cells (e.g., histamine release, $PGD_2$ release, $Ca^{2+}$ flux, and/or β-hexosaminidase release, etc.); (10) has been engineered to improve ADCC activity; (11) binds a human Siglec-8 expressed on mast cells and kills mast cells by ADCC activity (in vitro, and/or in vivo); (12) binds to Siglec-8 of a human and a non-human primate; (13) binds to Domain 1, Domain 2, and/or Domain 3 of human Siglec-8, or binds a Siglec-8 polypeptide comprising Domain 1, Domain 2, and/or Domain 3 of human Siglec-8 (e.g., fusion proteins described herein); and (14) depletes activated eosinophils with an $EC_{50}$ less than the $EC_{50}$ of mouse antibody 2E2 or 2C4. Any of the antibodies described in U.S. Pat. No. 9,546,215 and/or WO2015089117 may find use in the methods, compositions, and kits provided herein.

In one aspect, the present disclosure provides antibodies that bind to a human Siglec-8. In some embodiments, the human Siglec-8 comprises an amino acid sequence of SEQ ID NO:72. In some embodiments, the human Siglec-8 comprises an amino acid sequence of SEQ ID NO:73. In some embodiments, an antibody described herein binds to a human Siglec-8 expressed on mast cells and depletes or reduces the number of mast cells. In some embodiments, an antibody described herein binds to a human Siglec-8 expressed on mast cells and inhibits mast cell-mediated activity.

In one aspect, the invention provides antibodies that bind to a human Siglec-8. In some embodiments, the human Siglec-8 comprises an amino acid sequence of SEQ ID NO:72. In some embodiments, the human Siglec-8 comprises an amino acid sequence of SEQ ID NO:73. In some embodiments, the antibody described herein binds to an epitope in Domain 1 of human Siglec-8, wherein Domain 1 comprises the amino acid sequence of SEQ ID NO: 112. In some embodiments, the antibody described herein binds to an epitope in Domain 2 of human Siglec-8, wherein Domain 2 comprises the amino acid sequence of SEQ ID NO: 113. In some embodiments, the antibody described herein binds to an epitope in Domain 3 of human Siglec-8, wherein Domain 3 comprises the amino acid sequence of SEQ ID NO: 114. In some embodiments, the antibody described herein binds to a fusion protein comprising the amino acid of SEQ ID NO: 116 but not to a fusion protein comprising the amino acid of SEQ ID NO: 115. In some embodiments, the antibody described herein binds to a fusion protein comprising the amino acid of SEQ ID NO: 117 but not to a fusion protein comprising the amino acid of SEQ ID NO: 115. In some embodiments, the antibody described herein binds to a fusion protein comprising the amino acid of SEQ ID NO:117 but not to a fusion protein comprising the amino acid of SEQ ID NO:116. In some embodiments, the antibody described herein binds to a linear epitope in the extracellular domain of human Siglec-8. In some embodiments, the antibody described herein binds to a conformational epitope in the extracellular domain of human Siglec-8. In some embodiments, an antibody described herein binds to a human Siglec-8 expressed on eosinophils and induces apoptosis of eosinophils. In some embodiments, an antibody described herein binds to a human Siglec-8 expressed on mast cells and depletes mast cells. In some embodiments, an antibody described herein binds to a human Siglec-8 expressed on mast cells and inhibits mast cell-mediated activity. In some embodiments, an antibody described herein binds to a human Siglec-8 expressed on mast cells and kills mast cells by ADCC activity. In some embodiments, an antibody described herein depletes mast cells and inhibits mast cell activation. In some embodiments, an antibody herein depletes activated eosinophils and inhibits mast cell activation. In some embodiments, an antibody herein (e.g., a non-fucosylated anti-Siglec-8 antibody) depletes blood eosinophils and inhibits mast cell activation.

Provided herein is an isolated anti-Siglec-8 antibody that binds to human Siglec-8 and non-human primate Siglec-8. Identification of antibodies with primate cross-reactivity would be useful for preclinical testing of anti-Siglec-8 antibodies in non-human primates. In one aspect, the invention provides antibodies that bind to a non-human primate Siglec-8. In one aspect, the invention provides antibodies that bind to a human Siglec-8 and a non-human primate Siglec-8. In some embodiments, the non-human primate Siglec-8 comprises an amino acid sequence of SEQ ID NO: 118 or a portion thereof. In some embodiments, the non-human primate Siglec-8 comprises an amino acid sequence of SEQ ID NO: 119 or a portion thereof. In some embodiments, the non-human primate is a baboon (e.g., *Papio anubis*). In some embodiments, the antibody that binds to a human Siglec-8 and a non-human primate Siglec-8, binds to an epitope in Domain 1 of human Siglec-8. In a further embodiment, Domain 1 of human Siglec-8 comprises the amino acid sequence of SEQ ID NO: 112. In some embodiments, the antibody that binds to a human Siglec-8 and a non-human primate Siglec-8, binds to an epitope in Domain 3 of human Siglec-8. In a further embodiment, Domain 3 of human Siglec-8 comprises the amino acid sequence of SEQ ID NO: 114. In some embodiments, the antibody that binds to a human Siglec-8 and a non-human primate Siglec-8 is a humanized antibody, a chimeric antibody, or a human antibody. In some embodiments, the antibody that binds to a human Siglec-8 and a non-human primate Siglec-8 is a murine antibody. In some embodiments, the antibody that binds to a human Siglec-8 and a non-human primate Siglec-8 is a human IgG1 antibody.

In one aspect, an anti-Siglec-8 antibody described herein is a monoclonal antibody. In one aspect, an anti-Siglec-8 antibody described herein is an antibody fragment (including antigen-binding fragment), e.g., a Fab, Fab'-SH, Fv, scFv, or (Fab')₂ fragment. In one aspect, an anti-Siglec-8 antibody described herein comprises an antibody fragment (including antigen-binding fragment), e.g., a Fab, Fab'-SH, Fv, scFv, or (Fab')₂ fragment. In one aspect, an anti-Siglec-8 antibody described herein is a chimeric, humanized, or human antibody. In one aspect, any of the anti-Siglec-8 antibodies described herein are purified.

In one aspect, anti-Siglec-8 antibodies that compete with murine 2E2 antibody and murine 2C4 antibody binding to Siglec-8 are provided. Anti-Siglec-8 antibodies that bind to the same epitope as murine 2E2 antibody and murine 2C4 antibody are also provided. Murine antibodies to Siglec-8, 2E2 and 2C4 antibody are described in U.S. Pat. Nos. 8,207,305; 8,197,811, 7,871,612, and 7,557,191.

In one aspect, anti-Siglec-8 antibodies that compete with any anti-Siglec-8 antibody described herein (e.g., HEKA, HEKF, 1C3, 1H10, 4F11, 2C4, 2E2) for binding to Siglec-8 are provided. Anti-Siglec-8 antibodies that bind to the same epitope as any anti-Siglec-8 antibody described herein (e.g., HEKA, HEKF, 1C3, 1H10, 4F11, 2C4, 2E2) are also provided.

In one aspect of the present disclosure, polynucleotides encoding anti-Siglec-8 antibodies are provided. In certain embodiments, vectors comprising polynucleotides encoding anti-Siglec-8 antibodies are provided. In certain embodiments, host cells comprising such vectors are provided. In another aspect of the present disclosure, compositions comprising anti-Siglec-8 antibodies or polynucleotides encoding anti-Siglec-8 antibodies are provided. In certain embodiments, a composition of the present disclosure is a pharmaceutical formulation for the treatment of an allergic ocular disease (e.g., allergic conjunctivitis, keratoconjunctivitis, or giant papillary conjunctivitis). In certain embodiments, a composition of the present disclosure is a pharmaceutical formulation for the prevention of an allergic ocular disease (e.g., allergic conjunctivitis, keratoconjunctivitis, or giant papillary conjunctivitis).

In one aspect, provided herein is an anti-Siglec-8 antibody comprising 1, 2, 3, 4, 5, or 6 of the HVR sequences of the murine antibody 2C4. In one aspect, provided herein is an anti-Siglec-8 antibody comprising 1, 2, 3, 4, 5, or 6 of the HVR sequences of the murine antibody 2E2. In some embodiments, the HVR is a Kabat CDR or a Chothia CDR.

In one aspect, provided herein is an anti-Siglec-8 antibody comprising 1, 2, 3, 4, 5, or 6 of the HVR sequences of the murine antibody 1C3. In one aspect, provided herein is an anti-Siglec-8 antibody comprising 1, 2, 3, 4, 5, or 6 of the HVR sequences of the murine antibody 4F11. In one aspect, provided herein is an anti-Siglec-8 antibody comprising 1, 2, 3, 4, 5, or 6 of the HVR sequences of the murine antibody 1H10. In some embodiments, the HVR is a Kabat CDR or a Chothia CDR.

In some embodiments, the antibody described herein binds to an epitope in Domain 1 of human Siglec-8, wherein Domain 1 comprises the amino acid sequence of SEQ ID NO: 112. In some embodiments, the antibody described herein binds to an epitope in Domain 2 of human Siglec-8, wherein Domain 2 comprises the amino acid sequence of SEQ ID NO: 113. In some embodiments, the antibody described herein binds to an epitope in Domain 3 of human Siglec-8, wherein Domain 3 comprises the amino acid sequence of SEQ ID NO:114.

In some embodiments, the antibody described herein binds to a fusion protein comprising the amino acid of SEQ ID NO: 116 but not to a fusion protein comprising the amino acid of SEQ ID NO:115. In some embodiments, the antibody described herein binds to a fusion protein comprising the amino acid of SEQ ID NO: 117 but not to a fusion protein comprising the amino acid of SEQ ID NO: 115. In some embodiments, the antibody described herein binds to a fusion protein comprising the amino acid of SEQ ID NO: 117 but not to a fusion protein comprising the amino acid of SEQ ID NO:116.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO: 103. In some embodiments, the antibody described herein binds to an epitope in Domain 2 of human Siglec-8, wherein Domain 2 comprises the amino acid sequence of SEQ ID NO: 113.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO: 101, and (iii) HVR-L3 comprising the amino acid sequence of SEQ ID NO: 104. In some embodiments, the antibody described herein binds to an epitope in Domain 3 of human Siglec-8, wherein Domain 3 comprises the amino acid sequence of SEQ ID NO: 114. In some embodiments, the antibody described herein binds to human Siglec-8 and non-human primate Siglec-8.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO: 102, and (iii) HVR-L3 comprising the amino acid sequence of SEQ ID NO: 105. In some embodiments, the antibody described herein binds to an epitope in Domain 1 of human Siglec-8, wherein Domain 1 comprises the amino acid sequence of SEQ ID NO: 112. In some embodiments, the antibody described herein binds to human Siglec-8 and non-human primate Siglec-8.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO: 100, and (iii) HVR-L3 comprising the amino acid sequence of SEQ ID NO: 103.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO: 104.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96;

and/or a light chain variable region comprising (i) HVR-L1 comprising the amino acid sequence of SEQ ID NO:99, (ii) HVR-L2 comprising the amino acid sequence of SEQ ID NO: 102, and (iii) HVR-L3 comprising the amino acid sequence of SEQ ID NO: 105.

An anti-Siglec-8 antibody described herein may comprise any suitable framework variable domain sequence, provided that the antibody retains the ability to bind human Siglec-8. As used herein, heavy chain framework regions are designated "HC-FR1-FR4," and light chain framework regions are designated "LC-FR1-FR4." In some embodiments, the anti-Siglec-8 antibody comprises a heavy chain variable domain framework sequence of SEQ ID NO:26, 34, 38, and 45 (HC-FR1, HC-FR2, HC-FR3, and HC-FR4, respectively). In some embodiments, the anti-Siglec-8 antibody comprises a light chain variable domain framework sequence of SEQ ID NO:48, 51, 55, and 60 (LC-FR1, LC-FR2, LC-FR3, and LC-FR4, respectively). In some embodiments, the anti-Siglec-8 antibody comprises a light chain variable domain framework sequence of SEQ ID NO:48, 51, 58, and 60 (LC-FR1, LC-FR2, LC-FR3, and LC-FR4, respectively).

In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence of SEQ ID NO:63. In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence selected from SEQ ID NOs:67-70. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs: 51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:66. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs:51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:71. In one embodiment of these antibodies, the heavy chain variable domain comprises an amino acid sequence selected from SEQ ID NOs:2-10 and the light chain variable domain comprises and amino acid sequence selected from SEQ ID NOs: 16-22. In one embodiment of these antibodies, the heavy chain variable domain comprises an amino acid sequence selected from SEQ ID NOs:2-10 and the light chain variable domain comprises and amino acid sequence selected from SEQ ID NOs:23 or 24. In one embodiment of these antibodies, the heavy chain variable domain comprises an amino acid sequence selected from SEQ ID NOs: 11-14 and the light chain variable domain comprises and amino acid sequence selected from SEQ ID NOs: 16-22. In one embodiment of these antibodies, the heavy chain variable domain comprises an amino acid sequence selected from SEQ ID NOs: 11-14 and the light chain variable domain comprises and amino acid sequence selected from SEQ ID NOs:23 or 24. In one embodiment of these antibodies, the heavy chain variable domain comprises an amino acid sequence of SEQ ID NO:6 and the light chain variable domain comprises and amino acid sequence of SEQ ID NO:16. In one embodiment of these antibodies, the heavy chain variable domain comprises an amino acid sequence of SEQ ID NO:6 and the light chain variable domain comprises and amino acid sequence of SEQ ID NO:21.

In some embodiments, the heavy chain HVR sequences comprise the following:

```
a)HVR-H1
(IYGAH(SEQ ID NO: 61));

b)HVR-H2
(VIWAGGSTNYNSALMS(SEQ ID NO: 62));
and c)HVR-H3
(DGSSPYYYSMEY(SEQ ID NO: 63);

(DGSSPYYYGMEY(SEQ ID NO: 67);

(DGSSPYYYSMDY(SEQ ID NO: 68);

(DGSSPYYYSMEV(SEQ ID NO: 69);
or

DGSSPYYYGMDV(SEQ ID NO: 70)).
```

In some embodiments, the heavy chain HVR sequences comprise the following:

```
a)HVR-H1
(SYAMS(SEQ ID NO: 88);

DYYMY(SEQ ID NO: 89);
or

SSWMN(SEQ ID NO: 90));

b)HVR-H2
(IISSGGSYTYYSDSVKG(SEQ ID NO: 91);

RIAPEDGDTEYAPKFQG(SEQ ID NO: 92);
or

QIYPGDDYTNYNGKFKG(SEQ ID NO: 93));
and c)HVR-H3
(HETAQAAWFAY(SEQ ID NO: 94);

EGNYYGSSILDY(SEQ ID NO: 95);
or

LGPYGPFAD(SEQ ID NO: 96)).
```

In some embodiments, the heavy chain FR sequences comprise the following:

a) HC-FR1
(EVQLVESGGGLVQPGGSLRLSCAASGFSLT(SEQ ID NO: 26);

EVQLVESGGGLVQPGGSLRLSCAVSGFSLT(SEQ ID NO: 27);

QVQLQESGPGLVKPSETLSLTCTVSGGSIS(SEQ ID NO: 28);
or

QVQLQESGPGLVKPSETLSLTCTVSGFSLT(SEQ ID NO: 29));

b) HC-FR2
(WVRQAPGKGLEWVS(SEQ ID NO: 31);

WVRQAPGKGLEWLG(SEQ ID NO: 32);

WVRQAPGKGLEWLS(SEQ ID NO: 33);

WVRQAPGKGLEWVG(SEQ ID NO: 34);

WIRQPPGKGLEWIG(SEQ ID NO: 35);
or

WVRQPPGKGLEWLG(SEQ ID NO: 36));

c) HC-FR3
(RFTISKDNSKNTVYLQMNSLRAEDTAVYYCAR(SEQ ID NO: 38);

RLSISKDNSKNTVYLQMNSLRAEDTAVYYCAR(SEQ ID NO: 39);

RLTISKDNSKNTVYLQMNSLRAEDTAVYYCAR(SEQ ID NO: 40);

RFSISKDNSKNTVYLQMNSLRAEDTAVYYCAR(SEQ ID NO: 41);

RVTISVDTSKNQFSLKLSSVTAADTAVYYCAR(SEQ ID NO: 42);
or

RLSISKDNSKNQVSLKLSSVTAADTAVYYCAR(SEQ ID NO: 43));
and d) HC-FR4
(WGQGTTVTVSS(SEQ ID NO: 45);
or

WGQGTLVTVSS(SEQ ID NO: 46)).

In some embodiments, the light chain HVR sequences comprise the following:

a) HVR-L1
(SATSSVSYMH(SEQ ID NO: 64));

b) HVR-L2
(STSNLAS(SEQ ID NO: 65));
and c) HVR-L3
(QQRSSYPFT(SEQ ID NO: 66);
or

QQRSSYPYT(SEQ ID NO: 71)).

In some embodiments, the light chain HVR sequences comprise the following:

a) HVR-L1
(SASSSVSYMH(SEQ ID NO: 97);

RASQDITNYLN(SEQ ID NO: 98);
or

SASSSVSYMY(SEQ ID NO: 99));

b) HVR-L2
(DTSKLAY(SEQ ID NO: 100);

FTSRLHS(SEQ ID NO: 101);
or

DTSSLAS(SEQ ID NO: 102));
and c) HVR-L3
(QQWSSNPPT(SEQ ID NO: 103);

QQGNTLPWT(SEQ ID NO: 104);
or

QQWNSDPYT(SEQ ID NO: 105)).

In some embodiments, the antibody comprises:

a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO: 100, and (iii) HVR-L3 comprising the amino acid sequence of SEQ ID NO: 103;

a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO: 101, and (iii) HVR-L3 comprising the amino acid sequence of SEQ ID NO: 104; or a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO: 102, and (iii) HVR-L3 comprising the amino acid sequence of SEQ ID NO: 105.

In some embodiments, the light chain FR sequences comprise the following:

a) LC-FR1
(EIVLTQSPATLSLSPGERATLSC(SEQ ID NO: 48);
or

EIILTQSPATLSLSPGERATLSC(SEQ ID NO: 49));

b) LC-FR2
(WFQQKPGQAPRLLIY(SEQ ID NO: 51);

WFQQKPGQAPRLWIY(SEQ ID NO: 52);
or

WYQQKPGQAPRLLIY(SEQ ID NO: 53));

c) LC-FR3
(GIPARFSGSGSGTDFTLTISSLEPEDFAVYYC(SEQ ID NO: 55);

GVPARFSGSGSGTDYTLTISSLEPEDFAVYYC(SEQ ID NO: 56);

GVPARFSGSGSGTDFTLTISSLEPEDFAVYYC(SEQ ID NO: 57);
or

-continued

GIPARFSGSGSGTDYTLTISSLEPEDFAVYYC(SEQ ID NO: 58));
and d)LC-FR4
(FGPGTKLDIK(SEQ ID NO: 60)).

In some embodiments, provided herein is an anti-Siglec-8 antibody (e.g., a humanized anti-Siglec-8) antibody that binds to human Siglec-8, wherein the antibody comprises a heavy chain variable region and a light chain variable region, wherein the antibody comprises:
  (a) heavy chain variable domain comprising:
    (1) an HC-FR1 comprising the amino acid sequence selected from SEQ ID NOs:26-29;
    (2) an HVR-H1 comprising the amino acid sequence of SEQ ID NO:61;
    (3) an HC-FR2 comprising the amino acid sequence selected from SEQ ID NOs:31-36;
    (4) an HVR-H2 comprising the amino acid sequence of SEQ ID NO:62;
    (5) an HC-FR3 comprising the amino acid sequence selected from SEQ ID NOs:38-43;
    (6) an HVR-H3 comprising the amino acid sequence of SEQ ID NO:63; and
    (7) an HC-FR4 comprising the amino acid sequence selected from SEQ ID NOs:45-46, and/or
  (b) a light chain variable domain comprising:
    (1) an LC-FR1 comprising the amino acid sequence selected from SEQ ID NOs:48-49;
    (2) an HVR-L1 comprising the amino acid sequence of SEQ ID NO:64;
    (3) an LC-FR2 comprising the amino acid sequence selected from SEQ ID NOs:51-53;
    (4) an HVR-L2 comprising the amino acid sequence of SEQ ID NO:65;
    (5) an LC-FR3 comprising the amino acid sequence selected from SEQ ID NOs:55-58;
    (6) an HVR-L3 comprising the amino acid sequence of SEQ ID NO:66; and
    (7) an LC-FR4 comprising the amino acid sequence of SEQ ID NO:60.

In one aspect, provided herein is an anti-Siglec-8 antibody comprising a heavy chain variable domain selected from SEQ ID NOs:2-10 and/or comprising a light chain variable domain selected from SEQ ID NOs: 16-22. In one aspect, provided herein is an anti-Siglec-8 antibody comprising a heavy chain variable domain selected from SEQ ID NOs: 2-14 and/or comprising a light chain variable domain selected from SEQ ID NOs: 16-24. In one aspect, provided herein is an anti-Siglec-8 antibody comprising a heavy chain variable domain selected from SEQ ID NOs:2-10 and/or comprising a light chain variable domain selected from SEQ ID NO:23 or 24. In one aspect, provided herein is an anti-Siglec-8 antibody comprising a heavy chain variable domain selected from SEQ ID NOs: 11-14 and/or comprising a light chain variable domain selected from SEQ ID NOs: 16-22. In one aspect, provided herein is an anti-Siglec-8 antibody comprising a heavy chain variable domain selected from SEQ ID NOs: 11-14 and/or comprising a light chain variable domain selected from SEQ ID NO:23 or 24. In one aspect, provided herein is an anti-Siglec-8 antibody comprising a heavy chain variable domain of SEQ ID NO:6 and/or comprising a light chain variable domain selected from SEQ ID NO: 16 or 21.

In one aspect, provided herein is an anti-Siglec-8 antibody comprising a heavy chain variable domain selected from SEQ ID NOs: 106-108 and/or comprising a light chain variable domain selected from SEQ ID NOs: 109-111. In one aspect, provided herein is an anti-Siglec-8 antibody comprising a heavy chain variable domain of SEQ ID NO: 106 and/or comprising a light chain variable domain of SEQ ID NO: 109. In one aspect, provided herein is an anti-Siglec-8 antibody comprising a heavy chain variable domain of SEQ ID NO: 107 and/or comprising a light chain variable domain of SEQ ID NO: 110. In one aspect, provided herein is an anti-Siglec-8 antibody comprising a heavy chain variable domain of SEQ ID NO: 108 and/or comprising a light chain variable domain of SEQ ID NO: 111.

In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:2-14. In some embodiments, provided herein is an anti-Siglec-8 antibody comprising a heavy chain variable domain comprising an amino acid sequence having at least 90%, 910/% 92%, 93%, 94%, 95%, 96%, 97%, 98%, or 99% sequence identity to an amino acid sequence selected from SEQ ID NOs: 106-108. In some embodiments, an amino acid sequence having at least 90%, 91%, 92%, 93%, 94%, 95%, 960%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a heavy chain variable domain comprising an amino acid sequence of SEQ ID NO:6. In some embodiments, an anti-Siglec-8 antibody comprises a heavy chain variable domain comprising an amino acid sequence selected from SEQ ID NOs: 106-108.

In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs: 16-24. In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs: 109-111. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a light chain variable domain comprising an amino acid sequence of SEQ ID NO: 16 or 21. In some embodiments, an anti-Siglec-8 antibody comprises a heavy chain variable domain comprising an amino acid sequence selected from SEQ ID NOs:109-111.

In one aspect, the present disclosure provides an anti-Siglec-8 antibody comprising (a) one, two, or three VH HVRs selected from those shown in Table 1 and/or (b) one, two, or three VL HVRs selected from those shown in Table 1.

In one aspect, the present disclosure provides an anti-Siglec-8 antibody comprising (a) one, two, or three VH HVRs selected from those shown in Table 2 and/or (b) one, two, or three VL HVRs selected from those shown in Table 2.

In one aspect, the present disclosure provides an anti-Siglec-8 antibody comprising (a) one, two, three or four VH FRs selected from those shown in Table 3 and/or (b) one, two, three or four VL FRs selected from those shown in Table 3.

In some embodiments, provided herein is an anti-Siglec-8 antibody comprising a heavy chain variable domain and/or a light chain variable domain of an antibody shown in Table 4, for example, HAKA antibody, HAKB antibody, HAKC antibody, etc.

TABLE 1

Amino acid sequences of HVRs of antibodies

| Antibody Chain | HVR1 | HVR2 | HVR3 |
|---|---|---|---|
| 2E2 antibody | | | |
| Heavy chain | IYGAH SEQ ID NO: 61 | VIWAGGST NYNSALMS SEQ ID NO: 62 | DGSSPY YYSMEY SEQ ID NO: 63 |
| Light chain | SATSS VSYMH SEQ ID NO: 64 | STSN LAS SEQ ID NO: 65 | QQRSS YPFT SEQ ID NO: 66 |
| Humanized Heavy Chain Variants 2E2 RHA, 2E2 RHB, 2E2 RHC, 2E2 RHD, 2E2 RHE, 2E2 RHF, 2E2 RHG, 2E2 RHA2, and 2E2 RHB2 | | | |
| Heavy chain | IYGAH SEQ ID NO: 61 | VIWAGGST NYNSALMS SEQ ID NO: 62 | DGSSPY YYSMEY SEQ ID NO: 63 |
| Humanized Light Chain Variants 2E2 RKA, 2E2 RKB, 2E2 RKC, 2E2 RKD, 2E2 RKE, 2E2 RKF, and 2E2 RKG | | | |
| Light chain | SATSS VSYMH SEQ ID NO: 64 | STSN LAS SEQ ID NO: 65 | QQRSS YPFT SEQ ID NO: 66 |
| Humanized Heavy Chain Variants 2E2 RHE S-G, 2E2 RHE E-D, 2E2 RHE Y-V and 2E2 RHE triple | | | |
| 2E2 RHE S-G | IYGAH SEQ ID NO: 61 | VIWAGGST NYNSALMS SEQ ID NO: 62 | DGSSPY YYGMEY SEQ ID NO: 67 |
| 2E2 RHE E-D | IYGAH SEQ ID NO: 61 | VIWAGGST NYNSALMS SEQ ID NO: 62 | DGSSPY YYSMDY SEQ ID NO: 68 |
| 2E2 RHE Y-V | IYGAH SEQ ID | VIWAGGST NYNSALMS | DGSSPY YYSMEV |

TABLE 1-continued

Amino acid sequences of HVRs of antibodies

| Antibody Chain | HVR1 | HVR2 | HVR3 |
|---|---|---|---|
| | NO: 61 | SEQ ID NO: 62 | SEQ ID NO: 69 |
| 2E2 RHE triple | IYGAH SEQ ID NO: 61 | VIWAGGST NYNSALMS SEQ ID NO: 62 | DGSSPY YYGMDV SEQ ID NO: 70 |
| Humanized Light Chain Variants 2E2 RKA F-Y and 2E2 RKF F-Y | | | |
| 2E2 RKA F-Y | SATSS VSYMH SEQ ID NO: 64 | STSN LAS SEQ ID NO: 65 | QQRSS YPYT SEQ ID NO: 71 |
| 2E2 RKF F-Y | SATSS VSYMH SEQ ID NO: 64 | STSN LAS SEQ ID NO: 65 | QQRSS YPYT SEQ ID NO: 71 |

TABLE 2

Amino acid sequences of HVRs from murine 1C3, 1H10, and 4F11 antibodies

| Antibody | Chain | HVR1 | HVR2 | HVR3 |
|---|---|---|---|---|
| 1C3 | Heavy Chain | SYAMS SEQ ID NO: 88 | IISSGGSYT YYSDSVKG SEQ ID NO: 91 | HETAQA AWFAY SEQ ID NO: 94 |
| 1H10 | Heavy Chain | DYYMY SEQ ID NO: 89 | RIAPEDGDT EYAPKFQG SEQ ID NO: 92 | EGNYYG SSILDY SEQ ID NO: 95 |
| 4F11 | Heavy Chain | SSWMN SEQ ID NO: 90 | QIYPGDDYT NYNGKFKG SEQ ID NO: 93 | LGPYG PFAD SEQ ID NO: 96 |
| 1C3 | Light Chain | SASSS VSYMH SEQ ID NO: 97 | DTSK LAY SEQ ID NO: 100 | QQWSS NPPT SEQ ID NO: 103 |
| 1H10 | Light Chain | RASQDI TNYLN SEQ ID NO: 98 | FTSR LHS SEQ ID NO: 101 | QQGNT LPWT SEQ ID NO: 104 |
| 4F11 | Light Chain | SASSS VSYMY SEQ ID NO: 99 | DTSS LAS SEQ ID NO: 102 | QQWNS DPYT SEQ ID NO: 105 |

TABLE 3

Amino acid sequences of FRs of antibodies

| Heavy Chain | FR1 | FR2 | FR3 | FR4 |
|---|---|---|---|---|
| 2E2 | QVQLKESGPGLVA PSQSLSITCTVSGFS LT (SEQ ID NO: 25) | WVRQPPGKGLEW LG (SEQ ID NO: 30) | RLSISKDNSKSQVF LKINSLQTDDTAL YYCAR (SEQ ID NO: 37) | WGQGTSVTVSS (SEQ ID NO: 44) |

TABLE 3-continued

Amino acid sequences of FRs of antibodies

| | | | | |
|---|---|---|---|---|
| 2E2 RHA | EVQLVESGGGLVQ PGGSLRLSCAASGF SLT (SEQ ID NO: 26) | WVRQAPGKGLEW VS (SEQ ID NO: 31) | RFTISKDNSKNTVY LQMNSLRAEDTAV YYCAR (SEQ ID NO: 38) | WGQGTTVTVSS (SEQ ID NO: 45) |
| 2E2 RHB | EVQLVESGGGLVQ PGGSLRLSCAVSGF SLT (SEQ ID NO: 27) | WVRQAPGKGLEW LG (SEQ ID NO: 32) | RLSISKDNSKNTVY LQMNSLRAEDTAV YYCAR (SEQ ID NO: 39) | WGQGTTVTVSS (SEQ ID NO: 45) |
| 2E2 RHC | EVQLVESGGGLVQ PGGSLRLSCAVSGF SLT (SEQ ID NO: 27) | WVRQAPGKGLEW VS (SEQ ID NO: 31) | RFTISKDNSKNTVY LQMNSLRAEDTAV YYCAR (SEQ ID NO: 38) | WGQGTTVTVSS (SEQ ID NO: 45) |
| 2E2 RHD | EVQLVESGGGLVQ PGGSLRLSCAASGF SLT (SEQ ID NO: 26) | WVRQAPGKGLEW LS (SEQ ID NO: 33) | RFTISKDNSKNTVY LQMNSLRAEDTAV YYCAR (SEQ ID NO: 38) | WGQGTTVTVSS (SEQ ID NO: 45) |
| 2E2 RHE | EVQLVESGGGLVQ PGGSLRLSCAASGF SLT (SEQ ID NO: 26) | WVRQAPGKGLEW VG (SEQ ID NO: 34) | RFTISKDNSKNTVY LQMNSLRAEDTAV YYCAR (SEQ ID NO: 38) | WGQGTTVTVSS (SEQ ID NO: 45) |
| 2E2 RHF | EVQLVESGGGLVQ PGGSLRLSCAASGF SLT (SEQ ID NO: 26) | WVRQAPGKGLEW VS (SEQ ID NO: 31) | RLTISKDNSKNTV YLQMNSLRAEDTA VYYCAR (SEQ ID NO: 40) | WGQGTTVTVSS (SEQ ID NO: 45) |
| 2E2 RHG | EVQLVESGGGLVQ PGGSLRLSCAASGF SLT (SEQ ID NO: 26) | WVRQAPGKGLEW VS (SEQ ID NO: 31) | RFSISKDNSKNTVY LQMNSLRAEDTAV YYCAR (SEQ ID NO: 41) | WGQGTTVTVSS (SEQ ID NO: 45) |
| 2E2 RHA2 | QVQLQESGPGLVK PSETLSLTCTVSGG SIS (SEQ ID NO: 28) | WIRQPPGKGLEWI G (SEQ ID NO: 35) | RVTISVDTSKNQFS LKLSSVTAADTAV YYCAR (SEQ ID NO: 42) | WGQGTLVTVSS (SEQ ID NO: 46) |
| 2E2 RHB2 | QVQLQESGPGLVK PSETLSLTTVSGF SLT (SEQ ID NO: 29) | WVRQPPGKGLEW LG (SEQ ID NO: 36) | RLSISKDNSKNQVS LKLSSVTAADTAV YYCAR (SEQ ID NO: 43) | WGQGTLVTVSS (SEQ ID NO: 46) |
| 2E2 RHE S-G | EVQLVESGGGLVQ PGGSLRLSCAASGF SLT (SEQ ID NO: 26) | WVRQAPGKGLEW VG (SEQ ID NO: 34) | RFTISKDNSKNTVY LQMNSLRAEDTAV YYCAR (SEQ ID NO: 38) | WGQGTTVTVSS (SEQ ID NO: 45) |
| 2E2 RHE E-D | EVQLVESGGGLVQ PGGSLRLSCAASGF SLT (SEQ ID NO: 26) | WVRQAPGKGLEW VG (SEQ ID NO: 34) | RFTISKDNSKNTVY LQMNSLRAEDTAV YYCAR (SEQ ID NO: 38) | WGQGTTVTVSS (SEQ ID NO: 45) |
| 2E2 RHE Y-V | EVQLVESGGGLVQ PGGSLRLSCAASGF SLT (SEQ ID NO: 26) | WVRQAPGKGLEW VG (SEQ ID NO: 34) | RFTISKDNSKNTVY LQMNSLRAEDTAV YYCAR (SEQ ID NO: 38) | WGQGTTVTVSS (SEQ ID NO: 45) |
| 2E2 RHE triple | EVQLVESGGGLVQ PGGSLRLSCAASGF SLT (SEQ ID NO: 26) | WVRQAPGKGLEW VG (SEQ ID NO: 34) | RFTISKDNSKNTVY LQMNSLRAEDTAV YYCAR (SEQ ID NO: 38) | WGQGTTVTVSS (SEQ ID NO: 45) |
| Light Chain | FR1 | FR2 | FR3 | FR4 |
| 2E2 | QIILTQSPAIMSASP GEKVSITC (SEQ ID NO: 47) | WFQQKPGTSPKLW IY (SEQ ID NO: 50) | GVPVRFSGSGSGTS YSLTISRMEAEDA ATYYC (SEQ ID NO: 54) | FGSGTKLEIK (SEQ ID NO: 59) |
| RKA | EIVLTQSPATLSLSP GERATLSC (SEQ ID NO: 48) | WFQQKPGQAPRLL IY (SEQ ID NO: 51) | GIPARFSGSGSGTD FTLTISSLEPEDFAV YYC (SEQ ID NO: 55) | FGPGTKLDIK (SEQ ID NO: 60) |

TABLE 3-continued

Amino acid sequences of FRs of antibodies

| | | | | |
|---|---|---|---|---|
| RKB | EIILTQSPATLSLSPGERATLSC (SEQ ID NO: 49) | WFQQKPGQAPRLWIY (SEQ ID NO: 52) | GVPARFSGSGSGTDYTLTISSLEPEDFAVYYC (SEQ ID NO: 56) | FGPGTKLDIK (SEQ ID NO: 60) |
| RKC | EIILTQSPATLSLSPGERATLSC (SEQ ID NO: 49) | WFQQKPGQAPRLLIY (SEQ ID NO: 51) | GIPARFSGSGSGTDFTLTISSLEPEDFAVYYC (SEQ ID NO: 55) | FGPGTKLDIK (SEQ ID NO: 60) |
| RKD | EIVLTQSPATLSLSPGERATLSC (SEQ ID NO: 48) | WFQQKPGQAPRLWIY (SEQ ID NO: 52) | GIPARFSGSGSGTDFTLTISSLEPEDFAVYYC (SEQ ID NO: 55) | FGPGTKLDIK (SEQ ID NO: 60) |
| RKE | EIVLTQSPATLSLSPGERATLSC (SEQ ID NO: 48) | WFQQKPGQAPRLLIY (SEQ ID NO: 51) | GVPARFSGSGSGTDFTLTISSLEPEDFAVYYC (SEQ ID NO: 57) | FGPGTKLDIK (SEQ ID NO: 60) |
| RKF | EIVLTQSPATLSLSPGERATLSC (SEQ ID NO: 48) | WFQQKPGQAPRLLIY (SEQ ID NO: 51) | GIPARFSGSGSGTDYTLTISSLEPEDFAVYYC (SEQ ID NO: 58) | FGPGTKLDIK (SEQ ID NO: 60) |
| RKG | EIVLTQSPATLSLSPGERATLSC (SEQ ID NO: 48) | WYQQKPGQAPRLLIY (SEQ ID NO: 53) | GIPARFSGSGSGTDFTLTISSLEPEDFAVYYC (SEQ ID NO: 55) | FGPGTKLDIK (SEQ ID NO: 60) |
| RKA F-Y | EIVLTQSPATLSLSPGERATLSC (SEQ ID NO: 48) | WFQQKPGQAPRLLIY (SEQ ID NO: 51) | GIPARFSGSGSGTDFTLTISSLEPEDFAVYYC (SEQ ID NO: 55) | FGPGTKLDIK (SEQ ID NO: 60) |
| RKF F-Y | EIVLTQSPATLSLSPGERATLSC (SEQ ID NO: 48) | WFQQKPGQAPRLLIY (SEQ ID NO: 51) | GIPARFSGSGSGTDYTLTISSLEPEDFAVYYC (SEQ ID NO: 58) | FGPGTKLDIK (SEQ ID NO: 60) |

TABLE 4

Amino acid sequences of variable regions of antibodies

| Antibody Name | Variable Heavy Chain | Variable Light Chain |
|---|---|---|
| ch2C4 | ch2C4 VH | ch2C4 VK |
| ch2E2 | ch2E2 VH (SEQ ID NO: 1) | ch2E2 VK (SEQ ID NO: 15) |
| cVHKA | ch2E2 VH (SEQ ID NO: 1) | 2E2 RKA (SEQ ID NO: 16) |
| cVHKB | ch2E2 VH (SEQ ID NO: 1) | 2E2 RKB (SEQ ID NO: 17) |
| HAcVK | 2E2 RHA (SEQ ID NO: 2) | ch2E2 VK (SEQ ID NO: 15) |
| HBcVK | 2E2 RHB (SEQ ID NO: 3) | ch2E2 VK (SEQ ID NO: 15) |
| HAKA | 2E2 RHA (SEQ ID NO: 2) | 2E2 RKA (SEQ ID NO: 16) |
| HAKB | 2E2 RHA (SEQ ID NO: 2) | 2E2 RKB (SEQ ID NO: 17) |
| HAKC | 2E2 RHA (SEQ ID NO: 2) | 2E2 RKC (SEQ ID NO: 18) |
| HAKD | 2E2 RHA (SEQ ID NO: 2) | 2E2 RKD (SEQ ID NO: 19) |
| HAKE | 2E2 RHA (SEQ ID NO: 2) | 2E2 RKE (SEQ ID NO: 20) |
| HAKF | 2E2 RHA (SEQ ID NO: 2) | 2E2 RKF (SEQ ID NO: 21) |
| HAKG | 2E2 RHA (SEQ ID NO: 2) | 2E2 RKG (SEQ ID NO: 22) |
| HBKA | 2E2 RHB (SEQ ID NO: 3) | 2E2 RKA (SEQ ID NO: 16) |
| HBKB | 2E2 RHB (SEQ ID NO: 3) | 2E2 RKB (SEQ ID NO: 17) |
| HBKC | 2E2 RHB (SEQ ID NO: 3) | 2E2 RKC (SEQ ID NO: 18) |
| HBKD | 2E2 RHB (SEQ ID NO: 3) | 2E2 RKD (SEQ ID NO: 19) |
| HBKE | 2E2 RHB (SEQ ID NO: 3) | 2E2 RKE (SEQ ID NO: 20) |
| HBKF | 2E2 RHB (SEQ ID No: 3) | 2E2 RRF (SEQ ID NO: 21) |
| HBKG | 2E2 RHB (SEQ ID NO: 3) | 2E2 RKG (SEQ ID NO: 22) |
| HCKA | 2E2 RHC (SEQ ID NO: 4) | 2E2 RKA (SEQ ID NO: 16) |
| HCKB | 2E2 RHC (SEQ ID NO: 4) | 2E2 RKB (SEQ ID NO: 17) |
| HCKC | 2E2 RHC (SEQ ID NO: 4) | 2E2 RKC (SEQ ID NO: 18) |
| HCKD | 2E2 RHC (SEQ ID NO: 4) | 2E2 RKD (SEQ ID NO: 19) |
| HCKE | 2E2 RHC (SEQ ID NO: 4) | 2E2 RKE (SEQ ID NO: 20) |
| HCKF | 2E2 RHC (SEQ ID NO: 4) | 2E2 RKE (SEQ ID NO: 21) |
| HCKG | 2E2 RHC (SEQ ID NO: 4) | 2E2 RKG (SEQ ID NO: 22) |
| HDKA | 2E2 RHD (SEQ ID NO: 5) | 2E2 RKA (SEQ ID NO: 16) |
| HBKB | 2E2 RHD (SEQ ID NO: 5) | 2E2 RKB (SEQ ID NO: 17) |

TABLE 4-continued

Amino acid sequences of variable regions of antibodies

| Antibody Name | Variable Heavy Chain | Variable Light Chain |
|---|---|---|
| HDKC | 2E2 RHD (SEQ ID NO: 5) | 2E2 RKC (SEQ ID NO: 18) |
| HDKD | 2E2 RHD (SEQ ID NO: 5) | 2E2 RKD (SEQ ID NO: 19) |
| HDKE | 2E2 RHD (SEQ ID NO: 5) | 2E2 RKE (SEQ ID NO: 20) |
| HDKF | 2E2 RHD (SEQ ID NO: 5) | 2E2 RKF (SEQ ID NO: 21) |
| HDKG | 2E2 RHD (SEQ ID NO: 5) | 2E2 RKG (SEQ ID NO: 22) |
| HEKA | 2E2 RHE (SEQ ID NO: 6) | 2E2 RKA (SEQ ID NO: 16) |
| HEKB | 2E2 RHE (SEQ ID NO: 6) | 2E2 RKB (SEQ ID NO: 17) |
| HEKC | 2E2 RHE (SEQ ID NO. 6) | 2E2 RKC (SEQ ID NO: 18) |
| HERD | 2E2 RHE (SEQ ID NO: 6) | 2E2 RKD (SEQ ID NO: 19) |
| HERE | 2E2 RHE (SEQ ID NO: 6) | 2E2 RKE (SEQ ID NO: 20) |
| HEKF | 2E2 RHE (SEQ ID NO: 6) | 2E2 RKF (SEQ ID NO: 21) |
| HEKG | 2E2 RHE (SEQ ID NO: 6) | 2E2 RKG (SEQ ID NO: 22) |
| HFKA | 2E2 RHE (SEQ ID NO: 7) | 2E2 RKA (SEQ ID NO: 16) |
| HFKB | 2E2 RHF (SEQ ID NO: 7) | 2E2 RKB (SEQ ID NO: 17) |
| HFKC | 2E2 RHF (SEQ ID NO: 7) | 2E2 RKC (SEQ ID NO: 18) |
| HFKD | 2E2 RHF (SEQ ID NO: 7) | 2E2 RKD (SEQ ID NO: 19) |
| HFKE | 2E2 RHF (SEQ ID NO: 7) | 2E2 RKE (SEQ ID NO: 20) |
| HFKF | 2E2 RHF (SEQ ID NO: 7) | 2E2 RKF (SEQ ID NO: 21) |
| HFKG | 2E2 RHF (SEQ ID NO: 7) | 2E2 RKG (SEQ ID NO: 22) |
| HGKA | 2E2 RHG (SEQ ID NO: 8) | 2E2 RKA (SEQ ID NO: 16) |
| HGKB | 2E2 RHG (SEQ ID NO: 8) | 2E2 RKB (SEQ ID NO: 17) |
| HGKC | 2E2 RHG (SEQ ID NO: 8) | 2E2 RKC (SEQ ID NO: 18) |
| HGKD | 2E2 RHG (SEQ ID NO: 8) | 2E2 RKD (SEQ ID NO: 19) |
| HGKE | 2E2 RHG (SEQ ID NO: 8) | 2E2 RKE (SEQ ID NO: 20) |
| HGKF | 2E2 RHG (SEQ ID NO: 8) | 2E2 RKF (SEQ ID NO: 21) |
| HGHG | 2E2 RHG (SEQ ID NO: 8) | 2E2 RKG (SEQ ID NO: 22) |
| HA2KA | 2E2 RHA2 (SEQ ID NO: 9) | 2E2 RKA (SEQ ID NO: 16) |
| HA2KB | 2E2 RHA2 (SEQ ID NO: 9) | 2E2 RKB (SEQ ID NO: 17) |
| HB2KA | 2E2 RHB2 (SEQ ID NO: 10) | 2E2 RKA (SEQ ID NO: 16) |
| HB2KB | 2E2 RHB2 (SEQ ID NO: 10) | 2E2 RKB (SEQ ID NO: 17) |
| HA2KF | 2E2 RHA2 (SEQ ID NO: 9) | 2E2 RKF (SEQ ID NO: 21) |
| HB2KF | 2E2 RHB2 (SEQ ID NO: 10) | 2E2 RKF (SEQ ID NO: 21) |
| HA2KC | 2E2 RHA2 (SEQ ID NO: 9) | 2E2 RKC (SEQ ID NO: 18) |
| HA2KD | 2E2 RHA2 (SEQ ID NO: 9) | 2E2 RKD (SEQ ID NO: 19) |
| HA2KE | 2E2 RHA2 (SEQ ID NO: 9) | 2E2 RKE (SEQ ID NO: 20) |
| HA2KF | 2E2 RHA2 (SEQ ID NO: 9) | 2E2 RKF (SEQ ID NO: 21) |
| HA2KG | 2E2 RHA2 (SEQ ID NO: 9) | 2E2 RKG (SEQ ID NO: 22) |
| HB2KC | 2E2 RHB2 (SEQ ID NO: 10) | 2E2 RKC (SEQ ID NO: 18) |
| HB2KD | 2E2 RHB2 (SEQ ID NO: 10) | 2E2 RKD (SEQ ID NO: 19) |
| HB2KE | 2E2 RHB2 (SEQ ID NO: 10) | 2E2 RKE (SEQ ID NO: 20) |
| HA2KFmut | 2E2 RHA2 (SEQ ID NO: 9) | 2E2 RKF F-Y mut (SEQ ID NO: 24) |
| HB2KFmut | 2E2 RHB2 (SEQ ID NO: 10) | 2E2 RKF F-Y mut (SEQ ID NO: 24) |
| HEKAmut | 2E2 RHE (SEQ ID NO: 6) | 2E2 RKA F-Y mut (SEQ ID NO: 23) |
| HEKFmut | 2E2 RHE (SEQ ID NO: 6) | 2E2 RKF F-Y mut (SEQ ID NO: 24) |
| HAKFmut | 2E2 RHA (SEQ ID NO: 2) | 2E2 RKF F-Y mut (SEQ ID NO: 24) |
| HBKFmut | 2E2 RHB (SEQ ID NO: 3) | 2E2 RKF F-Y mut (SEQ ID NO: 24) |
| HCKFmut | 2E2 RHC (SEQ ID NO: 4) | 2E2 RKF F-Y mut (SEQ ID NO: 24) |
| HDKFmut | 2E2 RHD (SEQ ID NO: 5) | 2E2 RKF F-Y mut (SEQ ID NO: 24) |
| HFKFmut | 2E2 RHF (SEQ ID NO: 7) | 2E2 RKF F-Y mut (SEQ ID NO: 24) |
| HGKFmut | 2E2 RHG (SEQ ID NO: 8) | 2E2 RKF F-Y mut (SEQ ID NO: 24) |
| RHE Y-VKA | 2E2 RHE Y-V (SEQ ID NO: 13) | 2E2 RKA (SEQ ID NO: 16) |
| RHE Y-VKB | 2E2 RHE Y-V (SEQ ID NO: 13) | 2E2 RKB (SEQ ID NO: 17) |
| RHE Y-VKC | 2E2 RHE Y-V (SEQ ID NO: 13) | 2E2 RKC (SEQ ID NO: 18) |
| RHE Y-VKD | 2E2 RHE Y-V (SEQ ID NO: 13) | 2E2 RKD (SEQ ID NO: 19) |
| RHE Y-VKE | 2E2 RHE Y-V (SEQ ID NO: 13) | 2E2 RKE (SEQ ID NO: 20) |
| RHE Y-VKF | 2E2 RHE Y-V (SEQ ID NO: 13) | 2E2 RKF (SEQ ID NO: 21) |
| RHE Y-VKG | 2E2 RHE Y-V (SEQ ID NO: 13) | 2E2 RKG (SEQ ID NO: 22) |
| RHE E-DKA | 2E2 RHE E-D (SEQ ID NO: 12) | 2E2 RKA (SEQ ID NO: 16) |
| RHE E-DKB | 2E2 RHE E-D (SEQ ID NO: 12) | 2E2 RKB (SEQ ID NO: 17) |
| RHE E-DKC | 2E2 RHE E-D (SEQ ID NO: 12) | 2E2 RKC (SEQ ID NO: 18) |
| RHE E-DKD | 2E2 RHE E-D (SEQ ID NO: 12) | 2E2 RKD (SEQ ID NO: 19) |
| RHE E-DKE | 2E2 RHE E-D (SEQ ID NO: 12) | 2E2 RKE (SEQ ID NO: 20) |
| RHE E-DKF | 2E2 RHE E-D (SEQ ID NO: 12) | 2E2 RKF (SEQ ID NO: 21) |
| RHE E-DKG | 2E2 RHE E-D (SEQ ID NO: 12) | 2E2 RKG (SEQ ID NO: 22) |
| RHE E-DKFmut | 2E2 RHE E-D (SEQ ID NO: 12) | 2E2 RK F-Y mut (SEQ ID NO: 24) |
| RHE S-GKA | 2E2 RHE S-G (SEQ ID NO: 11) | 2E2 RKA (SEQ ID NO: 16) |
| RHE S-GKB | 2E2 RHE S-G (SEQ ID NO: 11) | 2E2 RKB (SEQ ID NO: 17) |
| RHE S-GKC | 2E2 RHE S-G (SEQ ID NO: 11) | 2E2 RKC (SEQ ID NO: 18) |
| RHE S-GKD | 2E2 RHE S-G (SEQ ID NO: 11) | 2E2 RKD (SEQ ID NO: 19) |
| RHE S-GKE | 2E2 RHE S-G (SEQ ID NO: 11) | 2E2 RKE (SEQ ID NO: 20) |
| RHE S-GKF | 2E2 RHE S-G (SEQ ID NO: 11) | 2E2 RKF (SEQ ID NO: 21) |
| RHE S-GKG | 2E2 RHE S-G (SEQ ID NO: 11) | 2E2 RKG (SEQ ID NO: 22) |
| RHE Triple-KA | 2E2 RHE triple (SEQ ID NO: 14) | 2E2 RKA (SEQ ID NO: 16) |
| RHE Triple-KB | 2E2 RHE triple (SEQ ID NO: 14) | 2E2 RKB (SEQ ID NO: 17) |

TABLE 4-continued

Amino acid sequences of variable regions of antibodies

| Antibody Name | Variable Heavy Chain | Variable Light Chain |
| --- | --- | --- |
| RHE Triple-KC | 2E2 RHE triple (SEQ ID NO: 14) | 2E2 RKC (SEQ ID NO: 18) |
| RHE Triple-KD | 2E2 RHE triple (SEQ ID NO: 14) | 2E2 RKD (SEQ ID NO: 19) |
| RHE Triple-KE | 2E2 RHE triple (SEQ ID NO: 14) | 2E2 RKE (SEQ ID NO: 20) |
| RHE Triple-KF | 2E2 RHE triple (SEQ ID NO: 14) | 2E2 RKF (SEQ ID NO: 21) |
| RHE Triple-KG | 2E2 RHE triple (SEQ ID NO: 14) | 2E2 RKG (SEQ ID NO: 22) |
| RHE Triple-KFmut | 2E2 RHE triple (SEQ ID NO: 14) | 2E2 RKF F-Y mut (SEQ ID NO: 24) |
| RHE Y-VKFmut | 2E2 RHE Y-V (SEQ ID NO: 13) | 2E2 RKF F-Y mut (SEQ ID NO: 24) |
| RHE E-DKFmut | 2E2 RHE E-D (SEQ ID NO: 12) | 2E2 RKF F-Y mut (SEQ ID NO: 24) |

There are five classes of immunoglobulins: IgA, IgD, IgE, IgG and IgM, having heavy chains designated α, δ, ε, γ and ρ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in some of the embodiments herein. Common allotypic variants in human populations are those designated by the letters a,f,n,z or combinations thereof. In any of the embodiments herein, the antibody may comprise a heavy chain Fc region comprising a human IgG Fc region. In further embodiments, the human IgG Fc region comprises a human IgG1 or IgG4. In some embodiments, the antibody is an IgG1 antibody. In some embodiments, the antibody is an IgG4 antibody. In some embodiments, the human IgG4 comprises the amino acid substitution S228P, wherein the amino acid residues are numbered according to the EU index as in Kabat. In some embodiments, the human IgG1 comprises the amino acid sequence of SEQ ID NO:78. In some embodiments, the human IgG4 comprises the amino acid sequence of SEQ ID NO:79.

In some embodiments, provided herein is an anti-Siglec-8 antibody comprising a heavy chain comprising the amino acid sequence of SEQ ID NO:75; and/or a light chain comprising the amino acid sequence selected from SEQ ID NOs:76 or 77. In some embodiments, the antibody may comprise a heavy chain comprising the amino acid sequence of SEQ ID NO:87; and/or a light chain comprising the amino acid sequence of SEQ ID NO:76. In some embodiments, the anti-Siglec-8 antibody induces apoptosis of activated eosinophils. In some embodiments, the anti-Siglec-8 antibody induces apoptosis of resting eosinophils. In some embodiments, the anti-Siglec-8 antibody depletes activated eosinophils and inhibits mast cell activation. In some embodiments, the anti-Siglec-8 antibody depletes or reduces mast cells and inhibits mast cell activation. In some embodiments, the anti-Siglec-8 antibody depleted or reduces the number of mast cells. In some embodiments, the anti-Siglec-8 antibody kills mast cells by ADCC activity. In some embodiments, the antibody depletes or reduces mast cells expressing Siglec-8 in a tissue. In some embodiments, the antibody depletes or reduces mast cells expressing Siglec-8 in a biological fluid.

1. Antibody Affinity

In some aspects, an anti-Siglec-8 antibody described herein binds to human Siglec-8 with about the same or higher affinity and/or higher avidity as compared to mouse antibody 2E2 and/or mouse antibody 2C4. In certain embodiments, an anti-Siglec-8 antibody provided herein has a dissociation constant (Kd) of ≤1 µM, ≤150 nM, ≤100 nM, ≤50 nM, ≤10 nM, ≤1 nM, ≤0.1 nM, ≤0.01 nM, or ≤0.001 nM (e.g. 10-8 M or less, e.g. from 10-8 M to 10-13 M. e.g., from 10-9 M to 10-13 M). In some embodiments, an anti-Siglec-8 antibody described herein binds to human Siglec-8 at about 1.5-fold, about 2-fold, about 3-fold, about 4-fold, about 5-fold, about 6-fold, about 7-fold, about 8-fold, about 9-fold or about 10-fold higher affinity than mouse antibody 2E2 and/or mouse antibody 2C4. In some embodiments, the anti-Siglec-8 antibody comprises a heavy chain variable region comprising the amino acid sequence of SEQ ID NO:6; and/or a light chain variable region comprising the amino acid sequence selected from SEQ ID NOs:16 or 21.

In one embodiment, the binding affinity of the anti-Siglec-8 antibody can be determined by a surface plasmon resonance assay. For example, the Kd or Kd value can be measured by using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore® Inc.) are activated with N-ethyl-N'-(3-dimethylaminopropyl)-carbodiimide hydrochloride (EDC) and N-hydroxysuccinimide (NHS) according to the supplier's instructions. Capture antibodies (e.g., anti-human-Fc) are diluted with 10 mM sodium acetate, pH 4.8, before injection at a flow rate of 30 l/minute and further immobilized with an anti-Siglec-8 antibody. For kinetics measurements, two-fold serial dilutions of dimeric Siglec-8 are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol. Biol. 293:865-881.

In another embodiment, biolayer interferometry may be used to determine the affinity of anti-Siglec-8 antibodies against Siglec-8. In an exemplary assay, Siglec-8-Fc tagged protein is immobilized onto anti-human capture sensors, and incubated with increasing concentrations of mouse, chimeric, or humanized anti-Siglec-8 Fab fragments to obtain affinity measurements using an instrument such as, for example, the Octet Red 384 System (ForteBio).

The binding affinity of the anti-Siglec-8 antibody can, for example, also be determined by the Scatchard analysis described in Munson et al., Anal. Biochem., 107:220 (1980) using standard techniques well known in the relevant art. See also Scatchard, G., Ann. N.Y. Acad. Sci. 51:660 (1947).

2. Antibody Avidity

In some embodiments, the binding avidity of the anti-Siglec-8 antibody can be determined by a surface plasmon resonance assay. For example, the Kd or Kd value can be measured by using a BIAcore T100. Capture antibodies (e.g., goat-anti-human-Fc and goat-anti-mouse-Fc) are immobilized on a CM5 chip. Flow-cells can be immobilized with anti-human or with anti-mouse antibodies. The assay is conducted at a certain temperature and flow rate, for example, at 25° C. at a flow rate of 30 μl/min. Dimeric Siglec-8 is diluted in assay buffer at various concentrations, for example, at a concentration ranging from 15 nM to 1.88 pM. Antibodies are captured and high performance injections are conducted, followed by dissociations. Flow cells are regenerated with a buffer, for example, 50 mM glycine pH 1.5. Results are blanked with an empty reference cell and multiple assay buffer injections, and analyzed with 1:1 global fit parameters.

3. Competition Assays

Competition-assays can be used to determine whether two antibodies bind the same epitope by recognizing identical or sterically overlapping epitopes or one antibody competitively inhibits binding of another antibody to the antigen. These assays are known in the art. Typically, antigen or antigen expressing cells is immobilized on a multi-well plate and the ability of unlabeled antibodies to block the binding of labeled antibodies is measured. Common labels for such competition assays are radioactive labels or enzyme labels. In some embodiments, an anti-Siglec-8 antibody described herein competes with a 2E2 antibody described herein, for binding to the epitope present on the cell surface of a cell (e.g., a mast cell). In some embodiments, an anti-Siglec-8 antibody described herein competes with an antibody comprising a heavy chain variable domain comprising the amino acid sequence of SEQ ID NO:1, and a light chain variable region comprising the amino acid sequence of SEQ ID NO:15, for binding to the epitope present on the cell surface of a cell (e.g., a mast cell). In some embodiments, an anti-Siglec-8 antibody described herein competes with a 2C4 antibody described herein, for binding to the epitope present on the cell surface of a cell (e.g., a mast cell). In some embodiments, an anti-Siglec-8 antibody described herein competes with an antibody comprising a heavy chain variable domain comprising the amino acid sequence of SEQ ID NO:2 (as found in U.S. Pat. No. 8,207,305), and a light chain variable region comprising the amino acid sequence of SEQ ID NO:4 (as found in U.S. Pat. No. 8,207,305), for binding to the epitope present on the cell surface of a cell (e.g., a mast cell).

4. Thermal Stability

In some aspects, an anti-Siglec-8 described herein has a melting temperature (Tm) of at least about 70° C., at least about 71° C., or at least about 72° C. in a thermal shift assay. In an exemplary thermal shift assay, samples comprising a humanized anti-Siglec-8 antibody are incubated with a fluorescent dye (Sypro Orange) for 71 cycles with 1° C. increase per cycle in a qPCR thermal cycler to determine the Tm. In some embodiments, the anti-Siglec-8 antibody has a similar or higher Tm as compared to mouse 2E2 antibody and/or mouse 2C4 antibody. In some embodiments, the anti-Siglec-8 antibody comprises a heavy chain variable region comprising the amino acid sequence of SEQ ID NO:6; and/or a light chain variable region comprising the amino acid sequence selected from SEQ ID NOs: 16 or 21. In some embodiments, the anti-Siglec-8 antibody has the same or higher Tm as compared to a chimeric 2C4 antibody. In some embodiments, the anti-Siglec-8 antibody has the same or higher Tm as compared to an antibody having a heavy chain comprising the amino acid sequence of SEQ ID NO:84 and a light chain comprising the amino acid sequence of SEQ ID NO:85.

5. Biological Activity Assays

In some embodiments, an anti-Siglec-8 antibody described herein depletes mast cells. Assays for assessing apoptosis of cells are well known in the art, for example staining with Annexin V and the TUNNEL assay.

In some embodiments, an anti-Siglec-8 antibody described herein induces ADCC activity. In some embodiments, an anti-Siglec-8 antibody described herein kills mast cells expressing Siglec-8 by ADCC activity. In some embodiments, a composition comprises non-fucosylated (i.e., afucosylated) anti-Siglec-8 antibodies. In some embodiments, a composition comprising non-fucosylated anti-Siglec-8 antibodies described herein enhances ADCC activity as compared to a composition comprising partially fucosylated anti-Siglec-8 antibodies. Assays for assessing ADCC activity are well known in the art and described herein. In an exemplary assay, to measure ADCC activity, effector cells and target cells are used. Examples of effector cells include natural killer (NK) cells, large granular lymphocytes (LGL), lymphokine-activated killer (LAK) cells and PBMC comprising NK and LGL, or leukocytes having Fc receptors on the cell surfaces, such as neutrophils, eosinophils and macrophages. Effector cells can be isolated from any source including individuals with a disease of interest (e.g., an allergic ocular disease). The target cell is any cell which expresses on the cell surface antigens that antibodies to be evaluated can recognize. An example of such a target cell is a mast cell which expresses Siglec-8 on the cell surface. Another example of such a target cell is a cell line (e.g., Ramos cell line) which expresses Siglec-8 on the cell surface (e.g., Ramos 2C10)). Target cells can be labeled with a reagent that enables detection of cytolysis. Examples of reagents for labeling include a radio-active substance such as sodium chromate ($Na_2^{51}CrO_4$). See, e.g., Immunology, 14, 181 (1968); J. Immunol. Methods., 172, 227 (1994); and J. Immunol. Methods., 184, 29 (1995).

In another exemplary assay to assess ADCC and apoptotic activity of anti-Siglec-8 antibodies on mast cells, human mast cells are isolated from human tissues or biological fluids according to published protocols (Guhl et al., Biosci. Biotechnol. Biochem., 2011, 75:382-384; Kulka et al., In Current Protocols in Immunology. 2001, (John Wiley & Sons, Inc.)) or differentiated from human hematopoietic stem cells, for example as described by Yokoi et al., J Allergy Clin Immunol., 2008, 121:499-505. Purified mast cells are resuspended in Complete RPMI medium in a sterile 96-well U-bottom plate and incubated in the presence or absence of anti-Siglec-8 antibodies for 30 minutes at concentrations ranging between 0.0001 ng/ml and 10 μg/ml. Samples are incubated for a further 4 to 48 hours with and without purified natural killer (NK) cells or fresh PBL to induce ADCC. Cell-killing by apoptosis or ADCC is analyzed by flow cytometry using fluorescent conjugated antibodies to detect mast cells (CD117 and FcεR1) and Annexin-V and 7AAD to discriminate live and dead or dying cells. Annexin-V and 7AAD staining are performed according to manufacturer's instructions.

In some aspects, an anti-Siglec-8 antibody described herein inhibits mast cell-mediated activities. Mast cell tryptase has been used as a biomarker for total mast cell number and activation. For example, total and active tryptase as well as histamine, N-methyl histamine, and 11-beta-prostaglandin F2 can be measured in blood or urine to assess the reduction in mast cells. See, e.g., U.S. Patent Application Publication No. US 20110293631 for an exemplary mast cell activity assay.

E. Antibody Preparation

The antibody described herein (e.g., an antibody that binds to human Siglec-8) is prepared using techniques available in the art for generating antibodies, exemplary methods of which are described in more detail in the following sections.

1. Antibody Fragments

The present disclosure encompasses antibody fragments. Antibody fragments may be generated by traditional means, such as enzymatic digestion, or by recombinant techniques. In certain circumstances there are advantages of using antibody fragments, rather than whole antibodies. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab. Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10: 163-167 (1992)). According to another approach. F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

The present disclosure encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent (e.g., mouse) antibody is screened against the entire library of known human variable-domain sequences. The human sequence which is closest to that of the rodent is then accepted as the human framework for the humanized antibody (Sims et al. (1993) *J. Immmuol.* 151: 2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA. 89:4285; Presta et al. (1993) *J. Immunol.*, 151:2623).

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those, skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Human Antibodies

Human anti-Siglec-8 antibodies of the present disclosure can be constructed by combining Fv clone variable domain sequence(s) selected from human-derived phage display libraries with known human constant domain sequences(s). Alternatively, human monoclonal anti-Siglec-8 antibodies of the present disclosure can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90: 2551 (1993); Jakobovits et al., *Nature,* 362: 255 (1993); Bruggermann et al., *Year in Immunol.,* 7: 33 (1993).

Gene shuffling can also be used to derive human antibodies from non-human (e.g., rodent) antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e., the epitope governs the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for Siglec-8 and the other is for any other antigen. In certain embodiments, bispecific antibodies may bind to two different epitopes of Siglec-8. Bispecific antibodies may also be used to localize cytotoxic agents to cells which express Siglec-8. Bispecific antibodies can be prepared as full length antibodies or antibody fragments (e.g. F(ab')$_2$ bispecific antibodies).

Methods for making bispecific antibodies are known in the art. See Milstein and Cuello, *Nature,* 305: 537 (1983), WO 93/08829 published May 13, 1993, and Traunecker et al., *EMBO J.,* 10: 3655 (1991). For further details of generating bispecific antibodies see, for example, Suresh et al., *Methods in Enzymology,* 121:210 (1986). Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking method. Suitable cross-linking agents are well known in the art, and are disclosed in U.S. Pat. No. 4,676,980, along with a number of cross-linking techniques.

5. Single-Domain Antibodies

In some embodiments, an antibody of the present disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham. Mass.; see, e.g., U.S. Pat. No. 6,248,516 B1). In one embodiment, a single-domain antibody consists of all or a portion of the heavy chain variable domain of an antibody.

6. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments, truncated forms of monoclonal antibodies can be made by recombinant techniques.

In certain embodiments, an antibody of the present disclosure is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta. L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene. FUT8, knockout CHO cells (Yamane-Ohnuki et al. Biotech. Bioeng. 87: 614 (2004)), and cells overexpressing β1,4-N-acetylglycosminyltransferase III (GnT-III) and Golgi μ-mannosidase II (ManIII).

Antibodies are contemplated herein that have reduced fucose relative to the amount of fucose on the same antibody produced in a wild-type CHO cell. For example, the antibody has a lower amount of fucose than it would otherwise have if produced by native CHO cells (e.g., a CHO cell that produce a native glycosylation pattern, such as, a CHO cell containing a native FUT8 gene). In certain embodiments, an anti-Siglec-8 antibody provided herein is one wherein less than about 50%, 40%, 30%, 20%, 10%, 5% or 1% of the N-linked glycans thereon comprise fucose. In certain embodiments, an anti-Siglec-8 antibody provided herein is one wherein none of the N-linked glycans thereon comprise fucose, i.e., wherein the antibody is completely without fucose, or has no fucose or is non-fucosylated or is afucosylated. The amount of fucose can be determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. In some embodiments, at least one or two of the heavy chains of the antibody is non-fucosylated.

In one embodiment, the antibody is altered to improve its serum half-life. To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311, U.S. Pat. Nos. 6,821,505; 6,165,745; 5,624,821; 5,648,260; 6,165,745; 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 5 under the heading of "preferred substitutions." If such substitutions result in a desirable change in biological activity, then more substantial changes, denominated "exemplary substitutions" in Table 5, or as further described below in reference to amino acid classes, may be introduced and the products screened.

TABLE 5

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):
  (1) non-polar: Ala (A), Val (V), Leu (L), Ile (I), Pro (P), Phe (F), Trp (W), Met (M)
  (2) uncharged polar: Gly (G), Ser (S), Thr (T), Cys (C), Tyr (Y), Asn (N), Gin (Q)
  (3) acidic: Asp (D), Glu (E)
  (4) basic: Lys (K), Arg (R), His (H)

Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gin;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g., a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g., binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the present disclosure, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine. In some embodiments, the Fc region variant comprises a human IgG4 Fc region. In a further embodiment, the human IgG4 Fc region comprises the amino acid substitution S228P, wherein the amino acid residues are numbered according to the EU index as in Kabat.

In accordance with this description and the teachings of the art, it is contemplated that in some embodiments, an antibody of the present disclosure may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40 (1988); U.S. Pat. Nos. 5,648,260; 5,624, 821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. J. Immunol. 164: 4178-4184 (2000).

7. Vectors, Host Cells, and Recombinant Methods

For recombinant production of an antibody of the present disclosure, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:
  a) Vector Construction

Polynucleotide sequences encoding polypeptide components of the antibody of the present disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the present disclosure may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the present disclosure. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the present disclosure, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of the present disclosure should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the present disclosure, the signal sequences used in both cistrons of the expression system are STII signal sequences or variants thereof.

In another aspect, the production of the immunoglobulins according to the present disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the present disclosure can also be produced by using an expression system in which the quantitative ratio of expressed polypeptide components can be modulated in order to maximize the yield of secreted and properly assembled antibodies of the present disclosure. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon, additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the present disclosure.

Prokaryotic host cells suitable for expressing antibodies of the present disclosure include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. acruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment. *E. coli* cells are used as hosts for the present disclosure. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as *E. coli* 294 (ATCC 31,446), *E. coli* B, *E. coli* λ1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the present disclosure are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for *E. coli* growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for *E. coli*, the pH is from about 6.8 to about 7.4, or about 7.0.

If an inducible promoter is used in the expression vector of the present disclosure, protein expression is induced under conditions suitable for the activation of the promoter. In one aspect of the present disclosure, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present disclosure are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the present disclosure, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose. Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the present disclosure, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present disclosure. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the present disclosure.

c) Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the present disclosure. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NS0, CHOK1, CHOK1SV or derivatives, including cell lines deficient in glutamine synthetase (GS). Methods for the use of GS as a selectable marker for mammalian cells are described in U.S. Pat. Nos. 5,122,464 and 5,891,693.

d) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

c) Enhancer Element Component

Transcription of DNA encoding an antibody of the present disclosure by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the mouse cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV 1 ATCC CCL 70): African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather t al., Annals N.Y. Acad. Sci. 383:44-68 (1982)); MRC 5 cells; FS4 cells; CHOK1 cells, CHOK1SV cells or derivatives and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of the present disclosure may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

Production of Non-Fucosylated Antibodies

Provided herein are methods for preparing antibodies with a reduced degree of fucosylation. For example, methods contemplated herein include, but are not limited to, use of cell lines deficient in protein fucosylation (e.g., Lee 13 CHO cells, alpha-1,6-fucosyltransferase gene knockout CHO cells, cells overexpressing β1,4-N-acetylglycosminyltransferase III and further overexpressing Golgi μ-mannosidase II, etc.), and addition of a fucose analog(s) in a cell culture medium used for the production of the antibodies. See Ripka et al. Arch. Biochem. Biophys. 249:533-545 (1986); US Pat Appl No US 2003/0157108 A1, Presta, L; WO 2004/056312 A1; Yamane-Ohnuki et al. Biotech. Bioeng. 87: 614 (2004); and U.S. Pat. No. 8,574,907. Additional techniques for reducing the fucose content of antibodies include Glymaxx technology described in U.S. Patent Application Publication No. 2012/0214975. Additional techniques for reducing the fucose content of antibodies also include the addition of one or more glycosidase inhibitors in a cell culture medium used for the production of the antibodies. Glycosidase inhibitors include α-glucosidase 1, α-glucosidase II, and α-mannosidase I. In some embodiments, the glycosidase inhibitor is an inhibitor of α-mannosidase I (e.g., kifunensine).

As used herein, "core fucosylation" refers to addition of fucose ("fucosylation") to N-acetylglucosamine ("GlcNAc") at the reducing terminal of an N-linked glycan. Also provided are antibodies produced by such methods and compositions thereof.

In some embodiments, fucosylation of complex N-glycoside-linked sugar chains bound to the Fc region (or domain) is reduced. As used herein, a "complex N-glycoside-linked sugar chain" is typically bound to asparagine 297 (according to the number of Kabat), although a complex N-glycoside linked sugar chain can also be linked to other asparagine residues. A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 1% of the antibody has core fucosylation by fucose in a composition. In some embodiments, substantially none (i.e., less than about 0.5%) of the antibody has core fucosylation by fucose in a composition. In some embodiments, more than about 40%, more than about 50%, more than about 60%, more than about 70%, more than about 80%, more than about 90%, more than about 91%, more than about 92%, more than about 93%, more than about 94%, more than about 95%, more than about 96%, more than about 97%, more than about 98%, or more than about 99% of the antibody is nonfucosylated in a composition.

In some embodiments, provided herein is an antibody wherein substantially none (i.e., less than about 0.5%) of the N-glycoside-linked carbohydrate chains contain a fucose residue. In some embodiments, provided herein is an antibody wherein at least one or two of the heavy chains of the antibody is non-fucosylated.

As described above, a variety of mammalian host-expression vector systems can be utilized to express an antibody. In some embodiments, the culture media is not supplemented with fucose. In some embodiments, an effective amount of a fucose analog is added to the culture media. In this context, an "effective amount" refers to an amount of the analog that is sufficient to decrease fucose incorporation into a complex N-glycoside-linked sugar chain of an antibody by at least about 10%, at least about 20%, at least about 30%, at least about 40% or at least about 50%. In some embodiments, antibodies produced by the instant methods comprise at least about 10%, at least about 20%, at least about 30%, at least about 40% or at least about 50% non-core fucosylated protein (e.g., lacking core fucosylation), as compared with antibodies produced from the host cells cultured in the absence of a fucose analog.

The content (e.g., the ratio) of sugar chains in which fucose is not bound to N-acetylglucosamine in the reducing end of the sugar chain versus sugar chains in which fucose is bound to N-acetylglucosamine in the reducing end of the sugar chain can be determined, for example, as described in the Examples. Other methods include hydrazinolysis or enzyme digestion (see, e.g., Biochemical Experimentation Methods 23: Method for Studying Glycoprotein Sugar Chain (Japan Scientific Societies Press), edited by Reiko Takahashi (1989)), fluorescence labeling or radioisotope labeling of the released sugar chain and then separating the labeled sugar chain by chromatography. Also, the compositions of the released sugar chains can be determined by analyzing the chains by the HPAEC-PAD method (see, e.g., J. Liq Chromatogr. 6:1557 (1983)). (See generally U.S. Patent Application Publication No. 2004/0110282.).

III. Compositions

In some aspects, also provided herein are compositions (e.g., pharmaceutical compositions) comprising any of the anti-Siglec-8 antibodies described herein (e.g., an antibody that binds to Siglec-8). In some aspects, provided herein is a composition comprising an anti-Siglec-8 antibody described herein, wherein the antibody comprises a Fc region and N-glycoside-linked carbohydrate chains linked to the Fc region, wherein less than about 50% of the N-glycoside-linked carbohydrate chains contain a fucose residue. In some embodiments, the antibody comprises a Fc region and N-glycoside-linked carbohydrate chains linked to the Fc region, wherein less than about 45%, about 40%, about 35%, about 30%, about 25%, about 20%, or about 15% of the N-glycoside-linked carbohydrate chains contain a fucose residue. In some aspects, provided herein is a composition comprising an anti-Siglec-8 antibody described herein, wherein the antibody comprises a Fc region and N-glycoside-linked carbohydrate chains linked to the Fc region, wherein substantially none of the N-glycoside-linked carbohydrate chains contain a fucose residue.

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g., Zn-protein complexes); chelating agents such as EDTA and/or non-ionic surfactants.

Buffers can be used to control the pH in a range which optimizes the therapeutic effectiveness, especially if stability is pH dependent. Buffers can be present at concentrations ranging from about 50 mM to about 250 mM. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present disclosure include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight or between about 1 to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001/to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Such active compounds are suitably present in combination in amounts that are effective for the purpose intended.

IV. Articles of Manufacture or Kits

In another aspect, an article of manufacture or kit is provided which comprises an anti-Siglec-8 antibody described herein (e.g., an antibody that binds human Siglec-8). The article of manufacture or kit may further comprise instructions for use of the antibody in the methods of the present disclosure. Thus, in certain embodiments, the article of manufacture or kit comprises instructions for the use of an anti-Siglec-8 antibody that binds to human Siglec-8 in methods for treating and/or preventing an allergic ocular disease (e.g., allergic conjunctivitis, keratoconjunctivitis, or giant papillary conjunctivitis) in an individual comprising administering to the individual an effective amount of an anti-Siglec-8 antibody that binds to human Siglec-8. In certain embodiments, the article of manufacture comprises a medicament comprising an antibody that binds to human Siglec-8 and a package insert comprising instructions for administration of the medicament in an individual in need thereof to treat and/or prevent an allergic ocular disease (e.g., allergic conjunctivitis, keratoconjunctivitis, or giant papillary conjunctivitis). In some embodiments, the package insert further indicates that the treatment is effective in reducing one or more symptoms in the individual with an allergic ocular disease (e.g., allergic conjunctivitis, keratoconjunctivitis, or giant papillary conjunctivitis) as compared to a baseline level before administration of the medicament. In some embodiments, the individual is diagnosed with an allergic ocular disease (e.g., allergic conjunctivitis, keratoconjunctivitis, or giant papillary conjunctivitis) before administration of the medicament comprising the antibody. In certain embodiments, the individual is a human.

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous, or other modes of administration for treating and/or preventing an allergic ocular disease (e.g., allergic conjunctivitis, keratoconjunctivitis, or giant papillary conjunctivitis) in an individual. The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

In a specific embodiment, the present disclosure provides kits for a single dose-administration unit. Such kits comprise a container of an aqueous formulation of therapeutic antibody, including both single or multi-chambered pre-filled syringes. Exemplary pre-filled syringes are available from Vetter GmbH, Ravensburg, Germany.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

In another aspect, an article of manufacture or kit is provided which comprises an anti-Siglec-8 antibody described herein (e.g., an antibody that binds human Siglec-8). The article of manufacture or kit may further comprise instructions for use of the antibody in the methods of the present disclosure. Thus, in certain embodiments, the article of manufacture or kit comprises instructions for the use of an anti-Siglec-8 antibody that binds to human Siglec-8 in methods for treating or preventing an allergic ocular disease (e.g., allergic conjunctivitis, keratoconjunctivitis, or giant papillary conjunctivitis) in an individual comprising administering to the individual an effective amount of an anti-Siglec-8 antibody that binds to human Siglec-8. In certain embodiments, the article of manufacture or kit comprises a medicament comprising an antibody that binds to human Siglec-8 and a package insert comprising instructions for administration of the medicament in an individual in need thereof to treat and/or prevent an allergic ocular disease (e.g., allergic conjunctivitis, keratoconjunctivitis, or giant papillary conjunctivitis).

The present disclosure also provides an article of manufacture or kit which comprises an anti-Siglec-8 antibody described herein (e.g., an antibody that binds human Siglec-8) in combination with one or more additional medicament (e.g., a second medicament) for treating or preventing an allergic ocular disease (e.g., allergic conjunctivitis, keratoconjunctivitis, or giant papillary conjunctivitis) in an individual. The article of manufacture or kit may further comprise instructions for use of the antibody in combination with one or more additional medicament in the methods of the present disclosure. For example, the article of manufacture or kit herein optionally further comprises a container comprising a second medicament, wherein the anti-Siglec-8 antibody is a first medicament, and which article or kit further comprises instructions on the label or package insert for treating the individual with the second medicament, in an effective amount. Thus in certain embodiments, the article of manufacture or kit comprises instructions for the use of an anti-Siglec-8 antibody that binds to human Siglec-8 in combination with one or more additional medicament in methods for treating or preventing an allergic ocular disease (e.g., allergic conjunctivitis, keratoconjunctivitis, or giant papillary conjunctivitis) in an individual. In certain embodiments, the article of manufacture or kit comprises a medicament comprising an antibody that binds to human Siglec-8 (e.g., a first medicament), one or more additional medicament and a package insert comprising instructions for administration of the first medicament in combination with the one or more additional medicament (e.g., a second medicament). In some embodiments, the one or more additional therapeutic agents may include, but are not limited to, a corticosteroid (e.g., budesonide, dexamethasone, hydrocortisone, methylprednisolone, prednisolone, or prednisone), antihistamine (e.g., levocabastine hydrochloride or olopatadine), ketotifen, azelastine, epinastine, bepostatine, cyclosporine, and a non-steroidal anti-inflammatory agent (NSAID).

It is understood that the aspects and embodiments described herein are for illustrative purposes only and that various modifications or changes in light thereof will be suggested to persons skilled in the art and are to be included within the spirit and purview of this application and scope of the appended claims.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Evaluation of Anti-Siglec-8 Antibodies in In Vivo Mouse Models of Allergic Conjunctivitis Animal models have been established for studying various allergic ocular diseases (see. e.g., Groneberg, D. A. et al. (2003) *Allergy* 58:1101-1113), including a mouse model for allergic conjunctivitis (Giavina-Bianchi. P, et al. (2008) *Acta Ophthalmol.* 86:670-675). For the evaluation of the effect of anti-Siglec-8 antibodies in murine models of allergic conjunctivitis, Siglec-8 transgenic mice are sensitized by systemic administration of allergen and then subjected to ocular allergen challenge followed by clinical assessment of conjunctivitis at time interval between 15 min and 24 hours post challenge to observe early and late-phase inflammatory responses.

A "Der p" model for C57Bl/6 mice described by Giavina-Bianchi, P. et al. (2008) *Acta Ophthalmol.* 86:670-675 is conducted as follows. Mice are immunized with solutions prepared from *D. pteronyssinus* ("Der p") extracts on day 0. After 10 days, ocular challenge is carried out in order to induce allergic conjunctivitis.

Clinical analysis and the collection of material for laboratory analyses are conducted 20 mins and up to 24 hours after ocular challenge. Specifically, mice are administered immunization solution containing 5-500 micrograms of allergen subcutaneously at the base of both hind legs and into the lower abdomen.

One-quarter of the dose is injected into each hind leg, and the remaining half is injected into the abdomen. Ten days after sensitization, mice are challenged with two drops of allergen solution (4-5 micrograms/microliter) in each eye. At intervals between 20 min and 24 hours post-challenge, mice are examined for conjunctival oedema, palpebral oedema; conjunctival hyperaemia, and lacrimation. Tissues and secretions are analyzed for cytokines and presence of inflammatory cells including mast cells and eosinophils. For the evaluation of activity of anti-Siglec-8 antibody, the antibody or an isotype control antibody are administered at a dose level of 0.1-5.0 mg/kg by intraperitoneal (ip) administration one day or 3 days prior to ocular challenge or using twice weekly administration from the time of sensitization.

For ovalbumin-induced conjunctivitis, Siglec-8 transgenic mice are sensitized by ip administration of 0.1 mg ovalbumin with 1 mg aluminum hydroxide adjuvant and 0.3 mg pertussis toxin, boosted on day 4 with 50 micrograms ovalbumin administered subcutaneously (sc), and challenged by ocular challenge with 0.75 mg ovalbumin on Day 17, according to the method described by Izushi, K. et al. (2002) *Eur. J. Pharmacol.* 440:79-82. Anti-Siglec-8 antibody treatments, clinical analyses, and laboratory analyses are conducted as described supra.

For ragweed-induced conjunctivitis, Siglec-8 transgenic mice are sensitized by sc administration of 50 micrograms ragweed extract and 5 mg aluminum hydroxide on Day 0, and ocular challenge is conducted with 1.25 mg ragweed extract on Day 9, as described by Magone, M. T. et al. (1998) *Clin. Immunol. Immunopathol.* 87(1):75-84. Anti-Siglec-8 antibody treatments, clinical analyses, and laboratory analyses are conducted as described supra.

Example 2: Structure of an Open-Label, Pilot Study to Assess the Efficacy and Safety of Anti-Siglec-8 Antibody Treatment in Patients with Atopic Keratoconjunctivitis (AKC), Vernal Keratoconjunctivitis (VKC), and Perennial Allergic Conjunctivitis (PAC)

The number of people afflicted with allergic ocular diseases has risen in the last decades and is now thought to affect at least 15-20% of the population (La Rosa, M. et al. (2013) *Ital. J. Pediatr.* 39:18). Allergic ocular diseases encompass a number of specific clinical entities with different mechanisms of action. This study is designed to test the safety and efficacy of anti-Siglec-8 antibody treatment in patients with AKC, VKC, or PAC.

A total of approximately 30 subjects are given 6 doses of anti-Siglec-8 antibody HEKA (non-fucosylated IgG1) at up to 3 mg/kg as monthly intravenous infusion. Clinical laboratory parameters and adverse events are assessed using the Common Terminology Criteria for Adverse Events (CT-CAE) version 4.03. Adverse events are collected starting from the time of first study drug infusion and ending at Day 309 (±7 Days) or at the Early Termination (ET) visit. The absolute peripheral blood counts of eosinophils and basophils are measured starting pre-dose on Day −1 and ending at Day 309 or ET visit. An Allergic Conjunctivitis Symptom (ACS) Questionnaire is used to evaluate symptoms associated with AKC, VKC, or PAC, and is completed by each subject daily throughout the study from Screening to Day 309 or ET visit.

Inclusion criteria include:
(a) age (≥18 and ≤80 years old);
(b) confirmed diagnosis of AKC, VKC, or PAC and, for at least one of the below symptoms, an average symptom score of ≥3 calculated from all daily ACS questionnaires completed during the screening period (minimum of 14 daily ACS questionnaires must be completed):
1. Itching
2. Photophobia
3. Eye pain
4. Foreign body sensation
5. Eye discharge
(c) history of topical corticosteroid and/or systemic corticosteroid use for the treatment of allergic conjunctivitis (AKC. VKC, or PAC);
(d) stable dose(s) of allowed AKC, VKC, or PAC medication(s) during the 14 days prior to screening and throughout the screening period; and commitment to remaining on the same dose(s) of AKC, VKC, or PAC medication(s) for the entire duration of study participation (unless dose modification is due to unforeseen medical necessity)

(e) negative screening ova and parasite test; and (f) negative pregnancy test (females).

Exclusion criteria include:

(a) history of malignancy except carcinoma in situ in the cervix, early stage prostate cancer or non-melanoma skin cancers;

(b) contact lens use within 48 hours prior to first dose of the antibody;

(c) participation in a concurrent interventional study with the last intervention occurring within 30 days prior to administration of study drug (or 90 days or 5 half-lives, whichever is longer, for biologic products);

(d) treatment with chemotherapy or radiotherapy in the preceding 6 months;

(e) treatment for a clinically significant helminthic parasitic infection within 6 months of screening;

(f) use during the 30 days before Screening (or 5 half-lives, whichever is longer) or use during the Screening period of topical decongestants, topical vasoconstrictors, topical calcineurin inhibitors, topical corticosteroids, omalizumab, dupilumab, systemic immunosuppressive drugs, or systemic corticosteroids with a daily dose >10 mg prednisone or equivalent (topical corticosteroids for atopic dermatitis, corticosteroid nasal sprays for rhinitis, and inhaled corticosteroids for allergic asthma are allowed);

(g) vaccination with live attenuated vaccines within 30 days prior to initiation of treatment in the study, during the treatment period, or vaccination expected within 5 half-lives (4 months) of the study drug administration;

(h) positive hepatitis serology results, except for vaccinated patients or patients with past but resolved hepatitis, at Screening; and (i) positive HIV serology results at Screening.

The primary outcome measure is the safety and tolerability of the antibody treatment based on evaluation of clinical laboratory parameters and adverse events as assessed using the Common Terminology Criteria for Adverse Events (CTCAE) version 4.03.

Secondary outcome measures include:

(a) changes from baseline in absolute peripheral blood counts of eosinophils and basophils (starting pre-dose on Day −1 to Day 309 or ET visit); and (b) changes from baseline symptoms associated with AKC, VKC, or PAC as measured daily by a disease-specific patient questionnaire, the Allergic Conjunctivitis Symptom (ACS) Questionnaire (throughout the study from screening to Day 309 or ET visit).

Optional secondary outcome measures include:

(a) changes from baseline quality of life as measured by the National Eye Institute Visual Functioning Questionnaire—25 (NEI VFQ 25) (starting pre-dose on Day −1 to Day 309 or ET visit);

(b) changes from baseline ocular signs (including punctuate corneal staining) in slit lamp color photography as assessed by centralized image reading center (starting pre-dose on Day −1 to Day 309 or ET visit);

(c) changes from baseline ophthalmic examination Ocular Symptom Scores as assessed by Investigator or Subinvestigator (starting pre-dose on Day −1 to Day 309 or ET visit);

(d) changes from baseline inflammatory mediators and anti-Siglec-8 antibody HEKA (non-fucosylated IgG1) concentration measured in optional lacrimal fluid (tear) samples (starting pre-dose on Day −1 to Day 309 or ET visit);

(e) changes from baseline histopathological examination of eosinophils and mast cells in optional conjunctival biopsies (collected on pre-dose Day −1 and on Day 169 or ET visit);

(f) changes from baseline signs and symptoms as measured by ACS disease-specific questionnaire daily symptom scores for 5 different symptoms (throughout the study from screening to Day 309 or ET visit);

(g) changes from baseline signs and symptoms as measure by the Quality of Life questionnaire, the National Eye Institute Visual Functioning Questionnaire 25 (NEI VFQ 25); and (i) changes from baseline signs and symptoms as measured by assessment of concomitant atopic conditions (atopic dermatitis, allergic asthma, allergic rhinitis).

Sequences

All polypeptide sequences are presented N-terminal to C-terminal unless otherwise noted.

All nucleic acid sequences are presented 5' to 3' unless otherwise noted.

```
Amino acid sequence of mouse 2E2 heavy chain variable domain
                                                                     (SEQ ID NO: 1)
QVQLKESGPGLVAPSQSLSITCTVSGFSLTIYGAHWVRQPPGKGLEWLGVIWAGGSTNY

NSALMSRLSISKDNSKSQVFLKINSLQTDDTALYYCARDGSSPYYYSMEYWGQGTSVT

VSS

Amino acid sequence of 2E2 RHA heavy chain variable domain
                                                                     (SEQ ID NO: 2)
EVQLVESGGGLVQPGGSLRLSCAASGFSLTIYGAHWVRQAPGKGLEWVSVIWAGGSTN

YNSALMSRFTISKDNSKNTVYLQMNSLRAEDTAVYYCARDGSSPYYYSMEYWGQGTT

VTVSS

Amino acid sequence of 2E2 RHB heavy chain variable domain
                                                                     (SEQ ID NO: 3)
EVQLVESGGGLVQPGGSLRLSCAVSGFSLTIYGAHWVRQAPGKGLEWLGVIWAGGSTN

YNSALMSRLSISKDNSKNTVYLQMNSLRAEDTAVYYCARDGSSPYYYSMEYWGQGTT

VTVSS
```

-continued

Amino acid sequence of 2E2 RHC heavy chain variable domain (SEQ ID NO: 4)
EVQLVESGGGLVWQPGGSLRLSCAVSGFSLTIYGAHWVRQAPGKGLEWVSVIWAGGSTN
YNSALMSRFTISKDNSKNTVYLQMNSLRAEDTAVYYCARDGSSPYYYSMEYWGQTT
VTVSS Amino acid sequence of 2E2 RHD heavy chain variable domain (SEQ ID NO: 5)
EVQLVESGGGLVQPGGSLRLSCAASGFSLTIYGAHWVRQAPGKGLEWLSVIWAGGSTN
YNSALMSRFTISKDNSKNTVYLQMNSLRAEDTAVYYCARDGSSPYYYSMEYWGQTT
VTVSS Amino acid sequence of 2E2 RHE heavy chain variable domain (SEQ ID NO: 6)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYSMEYWGQT
TVTVSS Amino acid sequence of 2E2 RHF heavy chain variable domain (SEQ ID NO: 7)
EVQLVESGGGLVQPGGSLRLSCAASGFSLTIYGAHWVRQAPGKGLEWVSVIWAGGSTN
YNSALMSRLTISKDNSKNTVYLQMNSLRAEDTAVYYCARDGSSPYYYSMEYWGQTT
VTVSS Amino acid sequence of 2E2 RHG heavy chain variable domain (SEQ ID NO: 8)
EVQLVESGGGLVQPGGSLRLSCAASGFSLTIYGAHWVRQAPGKGLEWVSVIWAGGSTN
YNSALMSRFSISKDNSKNTVYLQMNSLRAEDTAVYYCARDGSSPYYYSMEYWGQTT
VTVSS Amino acid sequence of 2E2 RHA2 heavy chain variable domain (SEQ ID NO: 9)
QVQLQESGPGLVKPSETLSLTCTVSGGSISIYGAHWIRQPPGKGLEWIGVIWAGGSTNYN
SALMSRVTISVDTSKNQFSLKLSSVTAADTAVYYCARDGSSPYYYSMEYWGQTLVTV
SS Amino acid sequence of 2E2 RHB2 heavy chain variable domain (SEQ ID NO: 10)
QVQLQESGPGLVKPSETLSLTCTVSGFSLTIYGAHWVRQPPGKGLEWLGVIWAGGSTN
YNSALMSRLSISKDNSKNQVSLKLSSVTAADTAVYYCARDGSSPYYYSMEYWGQTL
VTVSS Amino acid sequence of 2E2 RHE S-G mutant heavy chain variable domain (SEQ ID NO: 11)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYGMEYWGQT
TVTVSS Amino acid sequence of 2E2 RHE E-D heavy chain variable domain (SEQ ID NO: 12)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYSMDYWGQT
TVTVSS Amino acid sequence of 2E2 RHE Y-V heavy chain variable domain (SEQ ID NO: 13)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYSMEVWGQT
TVTVSS -continued Amino acid sequence of 2E2 RHE triple mutant heavy chain variable domain
(SEQ ID NO: 14)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYGMDVWGQG
TTVTVSS Amino acid sequence of 2E2 light chain variable domain
(SEQ ID NO: 15)
QIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIK Amino acid sequence of 2E2 RKA light chain variable domain
(SEQ ID NO: 16)
EIVLTQSPATLSLSPGERATLSCSATSSVSYMHWFQQKPGQAPRLLIYSTSNLASGIPARF
SGSGSGTDFTLTISSLEPEDFAVYYCQQRSSYPFTFGPGTKLDIK Amino acid sequence of 2E2 RKB light chain variable domain
(SEQ ID NO: 17)
EIILTQSPATLSLSPGERATLSCSATSSVSYMHWFQQKPGQAPRLWIYSTSNLASGVPARF
SGSGSGTDYTLTISSLEPEDFAVYYCQQRSSYPFTFGPGTKLDIK Amino acid sequence of 2E2 RKC light chain variable domain
(SEQ ID NO: 18)
EIILTQSPATLSLSPGERATLSCSATSSVSYMHWFQQKPGQAPRLLIYSTSNLASGIPARFS
GSGSGTDFTLTISSLEPEDFAVYYCQQRSSYPFTFGPGTKLDIK Amino acid sequence of 2E2 RKD light chain variable domain
(SEQ ID NO: 19)
EIVLTQSPATLSLSPGERATLSCSATSSVSYMHWFQQKPGQAPRLWIYSTSNLASGIPARF
SGSGSGTDFTLTISSLEPEDFAVYYCQQRSSYPFTFGPGTKLDIK Amino acid sequence of 2E2 RKE light chain variable domain
(SEQ ID NO: 20)
EIVLTQSPATLSLSPGERATLSCSATSSVSYMHWFQQKPGQAPRLLIYSTSNLASGVPAR
FSGSGSGTDFTLTISSLEPEDFAVYYCQQRSSYPFTFGPGTKLDIK Amino acid sequence of 2E2 RKF light chain variable domain
(SEQ ID NO: 21)
EIVLTQSPATLSLSPGERATLSCSATSSVSYMHWFQQKPGQAPRLLIYSTSNLASGIPARF
SGSGSGTDYTLTISSLEPEDFAVYYCQQRSSYPFTFGPGTKLDIK Amino acid sequence of 2E2 RKG light chain variable domain
(SEQ ID NO: 22)
EIVLTQSPATLSLSPGERATLSCSATSSVSYMHWYQQKPGQAPRLLIYSTSNLASGIPARF
SGSGSFTDFTLTISSLEPEDFAVYYCQQRSSYPFTFGPGTKLDIK Amino acid sequence of 2E2 RKA F-Y mutant light chain variable domain
(SEQ ID NO: 23)
EIVLTQSPATLSLSPGERATLSCSATSSVSYMHWFQQKPGQAPRLLIYSTSNLASGIPARF
SGSGSGTDFTLTISSLEPEDFAVYYCQQRSSYPYTFGPGTKLDIK Amino acid sequence of 2E2 RKF F-Y mutant light chain variable domain
(SEQ ID NO: 24)
EIVLTQSPATLSLSPGERATLSCSATSSVSYMHWFQQKPGQAPRLLIYSTSNLASGIPARF
SGSGSGTDYTLTISSLEPEDFAVYYCQQRSSYPYTFGPGTKLDIK Amino acid sequence of HEKA heavy chain and HEKF heavy chain
(SEQ ID NO: 75)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYSMEYWGQGT
TVTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKRVEPKSCDKTHTCPPCPA
PELLGGPSVFLFPPKPKDTLMISRTPEVTCVVVDVSHEDPEVKFNWYVDGVEVHNAKT -continued

KPREEQYNSTYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPVLDSDGSFFL

YSKLTVDKSRWQQGNVFSCSVMHEALHNHYTQKSLSLSPG

Amino acid sequence of HEKA light chain
(SEQ ID NO: 76)

EIVLTQSPATLSLSPGERATLSCSATSSVSYMHWFQQKPGQAPRLLIYSTSNLASGIPARF

SGSGSGTDFTLTISSLEPEDFAVYYCQQRSSYPFTFGPGTKLDIKRTVAAPSVFIFPPSDEQ

LKSGTASVVCLLNNFYPREAKVQWKVDNALQSGNSQESVTEQDSKDSTYSLSSTLTLS

KADYEKHKVYACEVTHQGLSSPVTKSFNRGEC

Amino acid sequence of HEKF light chain
(SEQ ID NO: 77)

EIVLTQSPATLSLSPGERATLSCSATSSVSYMHWFQQKPGQAPRLLIYSTSNLASGIPARF

SGSGSGTDYTLTISSLEPEDFAVYYCQQRSSYPFTFGPGTKLDIKRTVAAPSVFIFPPSDEQ

LKSGTASVVCLLNNFYPREAKVQWKVDNALQSGNSQESVTEQDSKDSTYSLSSTLTLS

KADYEKHKVYACEVTHQGLSSPVTKSFNRGEC

Amino acid sequence of IgG1 heavy chain constant region
(SEQ ID NO: 78)

ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCPPCPAPELLGG

PSVFLFPPKPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPREPQVYTLPPS

REEMTKNQVSLTCLVKGFYPSDIAVEWESNGQPENNYKTTPPVLDSDGSFFLYSKLTVD

KSRWQQGNVFSCSVMHEALHNHYTQKSLSLSPG

Amino acid sequence of IgG4 heavy chain constant region
(SEQ ID NO: 79)

ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVMHEALHNHYTQKSLSLSLG

Amino acid sequence of Ig kappa light chain constant region
(SEQ ID NO: 80)

RTVAAPSVFIFPPSDEQLKSGTASVVCLLNNFYPREAKVQWKVDNALQSGNSQESVTEQ

DSKDSTYSLSSTLTLSKADYEKHKVYACEVTHQGLSSPVTKSFNRGEC

Amino acid sequence of murine 2C4 and 2E2 IgG1 heavy chain
(SEQ ID NO: 81)

QVQLKRASGPGLVAPSQSLSITCTVSGFSLTIYGAHWVRQPPGKGLEWLGVIWAGGSTN

YNSALMSRLSISKDNSKSQVFLKINSLQTDDTALYYCARDGSSPYYYSMEYWGQGTSV

TVSSAKTTPPSVYPLAPGSAAQTNSMVTLGCLVKGYFPEPVTVTWNSGSLSSGVHTFPA

VLESDLYTLSSSVTVPSSPRPSETVTCNVAHPASSTKVDKKIVPRDCGCKPCICTVPEVSS

VFIFPPKPKDVLTITLTPKVTCVVVDISKDDPEVQFSWFVDDVEVHTAQTQPREEQFNST

FRSVSELPIMHQDWLNGKEFKCRVNSAAFPAPIEKTISKTKGRPKAPQVYTIPPPKEQMA

KDKVSLTCMITDFFPEDITVEWQWNGQPAENYKNTQPIMNTNGSYFVYSKLNVQKSN

WEAGNTFTCSVLHEGLHNHHTEKSLSHSPG

-continued

Amino acid sequence of murine 2C4 kappa light chain
(SEQ ID NO: 82)
EIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKADAAPTVSIFPPSSEQ
LTSGGASVVCFLNNFYPKDINVKWKIDGSERQNGVLNSWTDQDSKDSTYSMSSTLTLT
KDEYERHNSYTCEATHKTSTSPIVKSFNRNEC Amino acid sequence of murine 2E2 kappa light chain
(SEQ ID NO: 83)
QIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKADAAPTVSIFPPSSEQ
LTSGGASVVCFLNNFYPKDINVKWKIDGSERQNGVLNSWTDQDSKDSTYSMSSTLTLT
KDEYERHNSYTCEATHKTSTSPIVKSFNRNEC Amino acid sequence of chimeric 2C4 and 2E2 IgG1 heavy chain
(SEQ ID NO: 84)
QVQLKRASGPGLVAPSQSLSITCTVSGFSLTIYGAHWVRQPPGKGLEWLGVIWAGGSTN
YNSALMSRLSISKDNSKSQVFLKINSLQTDDTALYYCARDGSSPYYYSMEYWGQGTSV
TVSSASTKGPSVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKTHTCPPCPAPE
LLGGPSVFLFPPKPKDTLMISRTPEVTCVVVDVSHEDPEVKFNWYVDGVEVHNAKTKP
REEQYNSTYRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLDSDGSFFLYS
KLTVDKSRWQQGNVFSCSVMHEALHNHYTQKSLSLSPG Amino acid sequence of chimeric 2C4 kappa light chain
(SEQ ID NO: 85)
EIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKRTVAAPSVFIFPPSDE
QLKSGTASVVCLLNNFYPREAKVQWKVDNALQSGNSQESVTEQDSKDSTYSLSSTLTL
SKADYEKHKVYACEVTHQGLSSPVTKSFNRGEC Amino acid sequence of chimeric 2E2 kappa light chain
(SEQ ID NO: 86)
QIILTQSPAIMSASPGEKVSITCSATSSVSYMHWFQQKPGTSPKLWIYSTSNLASGVPVRF
SGSGSGTSYSLTISRMEAEDAATYYCQQRSSYPFTFGSGTKLEIKRTVAAPSVFIFPPSDE
QLKSGTASVVCLLNNFYPREAKVQWKVDNALQSGNSQESVTEQDSKDSTYSLSSTLTL
SKADYEKHKVYACEVTHQGLSSPVTKSFNRGEC Amino acid sequence of HEKA IgG4 heavy chain (IgG4 contains a S228P mutation)
(SEQ ID NO: 87)
EVQLVESGGGLVQPGGSLRLSCAASGFSLTIYGAHWVRQAPGKGLEWVGVIWAGGST
NYNSALMSRFTISKDNSKNTVYLQMNSLRAEDTAVYYCARDGSSPYYYSMEYWGQGT
TVTVSSASTKGPSVFPLAPCSRSTSESTAALGCLVKDYFPEPVTVSWNSGALTSGVHTFP
AVLQSSGLYSLSSVVTVPSSSLGTKTYTCNVDHKPSNTKVDKRVESKYGPPCPPCPAPEF
LGGPSVFLFPPKPKDTLMISRTPEVTCVVVDVSQEDPEVQFNWYVDGVEVHNAKTKPR
EEQFNSTYRVVSVLTVLHQDWLNGKEYKCKVSNKGLPSSIEKTISKAKGQPREPQVYTL
PPSQEEMTKNQVSLTCLVKGFYPSDIAVEWESNGQPENNYKTTPPVLDSDGSFFLYSRL
TVDKSRWQEGNVFSCSVMHEALHNHYTQKSLSLSLG Amino acid sequence of mouse 1C3 heavy chain variable domain (underlined residues comprise CDRs H1 and H2 according to Chothia numbering)

(SEQ ID NO: 106)

EVQVVESGGDLVKSGGSLKLSCAAS<u>GFPFSSY</u>AMSWVRQTPDKRLEWVAII<u>SSGGSYTY</u>

YSDSVKGRFTISRDNAKNTLYLQMSSLKSEDTAMYYCARHETAQAAWFAYWGQGTLV

TVSA

Amino acid sequence of mouse 1H10 heavy chain variable domain (underlined residues comprise CDRs H1 and H2 according to Chothia numbering)

(SEQ ID NO: 107)

EVQLQQSGAELVRPGASVKLSCTAS<u>GFNIKDY</u>YMYWVKQRPEQGLEWIGRI<u>APEDGDT</u>

EYAPKFQGKATVTADTSSNTAYLHLSSLTSEDTAVYYCTTEGNYYGSSILDYWGQGTT

LTVSS

Amino acid sequence of mouse 4F11 heavy chain variable domain (underlined residues comprise CDRs H1 and H2 according to Chothia numbering)

(SEQ ID NO: 108)

QVQLQQSGAELVKPGASVKISCKAS<u>GYAFRSS</u>WMNWVKQRPGKGLEWIGQI<u>YPGDDY</u>

TNYNGKFKGKVTLTADRSSSTAYMQLSSLTSEDSAVYFCARLGPYGPFADWGQGTLVT

VSA

Amino acid sequence of mouse 1C3 light chain variable domain (SEQ ID NO: 109)

QIVLTQSPAIMSASPGEKVTMTCSASSSVSYMHWYQQKSGTSPKRWIYDTSKLAYGVP

ARFSGSGSGTSYSLTISSMEAEDAATYYCQQWSSNPPTFGGGTKLEIK

Amino acid sequence of mouse 1H10 light chain variable domain (SEQ ID NO: 110)

DIQMTQTTSSLSASLGDRVTISCRASQDITNYLNWYQQKPDGTVKLLIYFTSRLHSGVPS

RFSGSGSGTDYSLTISNLEQEDIATYFCQQGNTLPWTFGGGTKLEIK

Amino acid sequence of mouse 4F11 light chain variable domain (SEQ ID NO: 111)

QIVLTQSPAIVSASPGEKVTMTCSASSSVSYMYWYQQRPGSSPRLLIYDTSSLASGVPVR

FSGSGSGTSYSLTISRIESEDAANYYCQQWNSDPYTFGGGTKLEIK

---

What is claimed is:

1. A method for treating an allergic ocular disease in an individual comprising administering to the individual an effective amount of a composition comprising an antibody that binds to human Siglec-8, wherein the individual is a human, wherein the individual has perennial allergic conjunctivitis, atopic keratoconjunctivitis, or vernal keratoconjunctivitis, wherein the antibody comprises a heavy chain comprising a heavy chain variable region and a light chain comprising a light chain variable region, and wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63, and the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

2. The method of claim 1, wherein the individual has increased inflammation in at least a portion of the conjunctiva, as compared to an individual without an allergic ocular disease.

3. The method of claim 2, wherein the individual has an increased number of mast cells, neutrophils, eosinophils, and/or lymphocytes in at least a portion of the conjunctiva, as compared to an individual without an allergic ocular disease.

4. The method of claim 1, wherein:
(a) a conjunctival scraping obtained from the individual comprises eosinophils;
(b) a serum or tear sample obtained from the individual has increased IgE, as compared to an individual without an allergic ocular disease; or
(c) an epicutaneous or intracutaneous allergy test administered to the individual using an allergen results in an allergic response.

5. The method of claim 1, wherein:
(a) one or more symptom(s) in the individual are reduced as compared to a baseline level before administration of the composition; or
(b) one or more of conjunctival itching, conjunctival redness, conjunctival swelling, ocular discharge, ulceration, tearing, lid hypertrophy, crusting, symblepharon, periocular eczema, madarosis, photophobia, keratitis, giant papillae, and cataracts in the individual are reduced as compared to a baseline level before administration of the composition.

6. The method of claim 1, wherein the composition is administered by intravenous infusion or subcutaneous injection.

7. The method of claim 1, wherein the antibody comprises a Fc region and N-glycoside-linked carbohydrate chains linked to the Fc region, wherein less than 50% of the N-glycoside-linked carbohydrate chains of the antibody in the composition contain a fucose residue.

8. The method of claim 7, wherein substantially none of the N-glycoside-linked carbohydrate chains of the antibody in the composition contain a fucose residue.

9. The method of claim 1, wherein the heavy chain variable region comprises the amino acid sequence of SEQ ID NO:6, and the light chain variable region comprises the amino acid sequence of SEQ ID NO:16 or 21.

10. The method of claim 1, wherein:
(a) the heavy chain variable region comprises:
  (1) an HC-FR1 comprising the amino acid sequence of SEQ ID NO:26;
  (2) an HVR-H1 comprising the amino acid sequence of SEQ ID NO:61;
  (3) an HC-FR2 comprising the amino acid sequence of SEQ ID NO:34;
  (4) an HVR-H2 comprising the amino acid sequence of SEQ ID NO:62;
  (5) an HC-FR3 comprising the amino acid sequence of SEQ ID NO:38;
  (6) an HVR-H3 comprising the amino acid sequence of SEQ ID NO:63; and
  (7) an HC-FR4 comprising the amino acid sequence of SEQ ID NOs:45; and
(b) the light chain variable region comprises:
  (1) an LC-FR1 comprising the amino acid sequence of SEQ ID NO:48;
  (2) an HVR-L1 comprising the amino acid sequence of SEQ ID NO:64;
  (3) an LC-FR2 comprising the amino acid sequence of SEQ ID NO:51;
  (4) an HVR-L2 comprising the amino acid sequence of SEQ ID NO:65;
  (5) an LC-FR3 comprising the amino acid sequence of SEQ ID NO:55 or 58;
  (6) an HVR-L3 comprising the amino acid sequence of SEQ ID NO:66; and
  (7) an LC-FR4 comprising the amino acid sequence of SEQ ID NO:60.

11. The method of claim 1, wherein the antibody is a humanized antibody or a chimeric antibody.

12. The method of claim 1, wherein the antibody depletes blood eosinophils and inhibits mast cell activation.

13. The method of claim 1, wherein the antibody comprises a heavy chain Fc region comprising a human IgG Fc region.

14. The method of claim 13, wherein the human IgG Fc region comprises a human IgG1 or human IgG4 Fc region.

15. The method of claim 14, wherein the human IgG1 Fc region is non-fucosylated.

16. The method of claim 14, wherein the human IgG4 Fc region comprises the amino acid substitution S228P, wherein the amino acid residues are numbered according to the EU index as in Kabat.

17. The method of claim 1, wherein the antibody has been engineered to improve antibody-dependent cell-mediated cytotoxicity (ADCC) activity.

18. The method of claim 1, wherein at least one or two of the heavy chains of the antibody is non-fucosylated.

19. The method of claim 1, wherein the antibody is a monoclonal antibody.

20. The method of claim 1, wherein the composition is administered in combination with one or more additional therapeutic agent(s) for treating or preventing an allergic ocular disease.

21. The method of claim 20, wherein the one or more additional therapeutic agent(s) are selected from the group consisting of a corticosteroid, antihistamine, ketotifen, azelastine, epinastine, bepostatine, cyclosporine, and a non-steroidal anti-inflammatory agent (NSAID).

22. The method of claim 1, wherein the composition is a pharmaceutical composition comprising the antibody and a pharmaceutically acceptable carrier.

23. The method of claim 1, wherein the heavy chain comprises the amino acid sequence of SEQ ID NO:75, and the light chain comprises the amino acid sequence of SEQ ID NO:76.

* * * * *

SEQUENCE LISTING

<160> NUMBER OF SEQ ID NOS: 124

<210> SEQ ID NO 1
<211> LENGTH: 120
<212> TYPE: PRT
<213> ORGANISM: Mus musculus

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Ile Asn Ser Leu Gln Thr Asp Asp Thr Ala Leu Tyr Tyr Cys Ala
                85                  90                  95

Arg Asp Gly Ser Ser Pro Tyr Tyr Tyr Ser Met Glu Tyr Trp Gly Gln
            100                 105                 110

```
Gly Thr Ser Val Thr Val Ser Ser
        115                 120

<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct
```

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Leu
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
            50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
                100                 105                 110

Gly Thr Thr Val Thr Val Ser Ser
            115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
                100                 105                 110

Gly Thr Thr Val Thr Val Ser Ser
            115                 120

<210> SEQ ID NO 8
<211> LENGTH: 120
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln

```
                    100                 105                 110

Gly Thr Thr Val Thr Val Ser Ser
            115                 120

<210> SEQ ID NO 9
<211> LENGTH: 120
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Gly Ala His Trp Ile Arg Gln Pro Pro Gly Lys Gly Leu Glu Trp Ile
        35                  40                  45

Gly Val Ile Trp Ala Gly Gly Ser Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
            115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
            115                 120

<210> SEQ ID NO 11
<211> LENGTH: 120
<212> TYPE: PRT
<213> ORGANISM: Artificial Sequence
<220> FEATURE:
```

<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Glu Tyr Trp Gly Gln
            100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Asp Tyr Trp Gly Gln
            100                 105                 110

Gly Thr Thr Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val

```
                    35                  40                  45
Gly Val Ile Trp Ala Gly Gly Ser Thr Asn Tyr Asn Ser Ala Leu Met
        50                  55                  60
Ser Arg Phe Thr Ile Ser Lys Asp Asn Ser Lys Asn Thr Val Tyr Leu
65                  70                  75                  80
Gln Met Asn Ser Leu Arg Ala Glu Asp Thr Ala Val Tyr Tyr Cys Ala
                85                  90                  95
Arg Asp Gly Ser Ser Pro Tyr Tyr Tyr Ser Met Glu Val Trp Gly Gln
            100                 105                 110
Gly Thr Thr Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Thr Ile Tyr
            20                  25                  30
Gly Ala His Trp Val Arg Gln Ala Pro Gly Lys Gly Leu Glu Trp Val
        35                  40                  45
Gly Val Ile Trp Ala Gly Gly Ser Thr Asn Tyr Asn Ser Ala Leu Met
    50                  55                  60
Ser Arg Phe Thr Ile Ser Lys Asp Asn Ser Lys Asn Thr Val Tyr Leu
65                  70                  75                  80
Gln Met Asn Ser Leu Arg Ala Glu Asp Thr Ala Val Tyr Tyr Cys Ala
                85                  90                  95
Arg Asp Gly Ser Ser Pro Tyr Tyr Tyr Gly Met Asp Val Trp Gly Gln
            100                 105                 110
Gly Thr Thr Val Thr Val Ser Ser
            115                 120

<210> SEQ ID NO 15
<211> LENGTH: 106
<212> TYPE: PRT
<213> ORGANISM: Artificial Sequence
<220> FEATURE:
<223> OTHER INFORMATION: Synthetic Construct

<400> SEQUENCE: 15

Gln Ile Ile Leu Thr Gln Ser Pro Ala Ile Met Ser Ala Ser Pro Gly
1               5                   10                  15
Glu Lys Val Ser Ile Thr Cys Ser Ala Thr Ser Ser Val Ser Tyr Met
            20                  25                  30
His Trp Phe Gln Gln Lys Pro Gly Thr Ser Pro Lys Leu Trp Ile Tyr
        35                  40                  45
Ser Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Ser Ser Tyr Pro Phe Thr
                85                  90                  95
```

Phe Gly Ser Gly Thr Lys Leu Glu Ile Lys
            100                 105

<210> SEQ ID NO 16
<211> LENGTH: 106
<212> TYPE: PRT
<213> ORGANISM: Artificial Sequence
<220> FEATURE:
<223> OTHER INFORMATION: Synthetic Construct

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Synthetic Construct

<400> SEQUENCE: 17

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met

```
                    20                  25                  30
His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
                100                 105

<210> SEQ ID NO 19
<211> LENGTH: 106
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Trp Ile Tyr
            35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
                100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
                100                 105
```

```
<210> SEQ ID NO 21
<211> LENGTH: 106
<212> TYPE: PRT
<213> ORGANISM: Artificial Sequence
<220> FEATURE:
<223> OTHER INFORMATION: Synthetic Construct

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
```

```
                35                  40                  45
Ser Thr Ser Asn Leu Ala Ser Gly Ile Pro Ala Arg Phe Gly Ser
         50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 25
<211> LENGTH: 30
<212> TYPE: PRT
<213> ORGANISM: Homo sapiens

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
            20                  25                  30

<210> SEQ ID NO 26
<211> LENGTH: 30
<212> TYPE: PRT
<213> ORGANISM: Homo sapiens

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr
            20                  25                  30

<210> SEQ ID NO 27
<211> LENGTH: 30
<212> TYPE: PRT
<213> ORGANISM: Homo sapiens
```

```
<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr
            20                  25                  30

<210> SEQ ID NO 28
<211> LENGTH: 30
<212> TYPE: PRT
<213> ORGANISM: Homo sapiens

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 29
<211> LENGTH: 30
<212> TYPE: PRT
<213> ORGANISM: Homo sapiens

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 30
<211> LENGTH: 14
<212> TYPE: PRT
<213> ORGANISM: Homo sapiens

<400> SEQUENCE: 30

Trp Val Arg Gln Pro Pro Gly Lys Gly Leu Glu Trp Leu Gly
1               5                   10

<210> SEQ ID NO 31
<211> LENGTH: 14
<212> TYPE: PRT
<213> ORGANISM: Homo sapiens

<400> SEQUENCE: 31

Trp Val Arg Gln Ala Pro Gly Lys Gly Leu Glu Trp Val Ser
1               5                   10

<210> SEQ ID NO 32
<211> LENGTH: 14
<212> TYPE: PRT
<213> ORGANISM: Homo sapiens

<400> SEQUENCE: 32

Trp Val Arg Gln Ala Pro Gly Lys Gly Leu Glu Trp Leu Gly
1               5                   10

<210> SEQ ID NO 33
<211> LENGTH: 14
<212> TYPE: PRT
<213> ORGANISM: Homo sapiens

<400> SEQUENCE: 33

Trp Val Arg Gln Ala Pro Gly Lys Gly Leu Glu Trp Leu Ser
1               5                   10
```

<210> SEQ ID NO 34
<211> LENGTH: 14
<212> TYPE: PRT
<213> ORGANISM: Homo sapiens

<400> SEQUENCE: 34

Trp Val Arg Gln Ala Pro Gly Lys Gly Leu Glu Trp Val Gly
1               5                   10

<210> SEQ ID NO 35
<211> LENGTH: 14
<212> TYPE: PRT
<213> ORGANISM: Homo sapiens

<400> SEQUENCE: 35

Trp Ile Arg Gln Pro Pro Gly Lys Gly Leu Glu Trp Ile Gly
1               5                   10

<210> SEQ ID NO 36
<211> LENGTH: 14
<212> TYPE: PRT
<213> ORGANISM: Homo sapiens

<400> SEQUENCE: 36

Trp Val Arg Gln Pro Pro Gly Lys Gly Leu Glu Trp Leu Gly
1               5                   10

<210> SEQ ID NO 37
<211> LENGTH: 32
<212> TYPE: PRT
<213> ORGANISM: Homo sapiens

<400> SEQUENCE: 37

Arg Leu Ser Ile Ser Lys Asp Asn Ser Lys Ser Gln Val Phe Leu Lys
1               5                   10                  15

Ile Asn Ser Leu Gln Thr Asp Asp Thr Ala Leu Tyr Tyr Cys Ala Arg
            20                  25                  30

<210> SEQ ID NO 38
<211> LENGTH: 32
<212> TYPE: PRT
<213> ORGANISM: Homo sapiens

<400> SEQUENCE: 38

Arg Phe Thr Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 39
<211> LENGTH: 32
<212> TYPE: PRT
<213> ORGANISM: Homo sapiens

<400> SEQUENCE: 39

Arg Leu Ser Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 40
<211> LENGTH: 32

```
<212> TYPE: PRT
<213> ORGANISM: Homo sapiens

<400> SEQUENCE: 40

Arg Leu Thr Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 41
<211> LENGTH: 32
<212> TYPE: PRT
<213> ORGANISM: Homo sapiens

<400> SEQUENCE: 41

Arg Phe Ser Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Homo sapiens

<400> SEQUENCE: 42

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 43
<211> LENGTH: 32
<212> TYPE: PRT
<213> ORGANISM: Homo sapiens

<400> SEQUENCE: 43

Arg Leu Ser Ile Ser Lys Asp Asn Ser Lys Asn Gln Val Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 44
<211> LENGTH: 11
<212> TYPE: PRT
<213> ORGANISM: Homo sapiens

<400> SEQUENCE: 44

Trp Gly Gln Gly Thr Ser Val Thr Val Ser Ser
1               5                   10

<210> SEQ ID NO 45
<211> LENGTH: 11
<212> TYPE: PRT
<213> ORGANISM: Homo sapiens

<400> SEQUENCE: 45

Trp Gly Gln Gly Thr Thr Val Thr Val Ser Ser
1               5                   10

<210> SEQ ID NO 46
<211> LENGTH: 11
<212> TYPE: PRT
```

```
<213> ORGANISM: Homo sapiens

<400> SEQUENCE: 46

Trp Gly Gln Gly Thr Leu Val Thr Val Ser Ser
1               5                   10

<210> SEQ ID NO 47
<211> LENGTH: 23
<212> TYPE: PRT
<213> ORGANISM: Homo sapiens

<400> SEQUENCE: 47

Gln Ile Ile Leu Thr Gln Ser Pro Ala Ile Met Ser Ala Ser Pro Gly
1               5                   10                  15

Glu Lys Val Ser Ile Thr Cys
            20

<210> SEQ ID NO 48
<211> LENGTH: 23
<212> TYPE: PRT
<213> ORGANISM: Homo sapiens

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 49
<211> LENGTH: 23
<212> TYPE: PRT
<213> ORGANISM: Homo sapiens

<400> SEQUENCE: 49

Glu Ile Ile Leu Thr Gln Ser Pro Ala Thr Leu Ser Leu Ser Pro Gly
1               5                   10                  15

Glu Arg Ala Thr Leu Ser Cys
            20

<210> SEQ ID NO 50
<211> LENGTH: 15
<212> TYPE: PRT
<213> ORGANISM: Homo sapiens

<400> SEQUENCE: 50

Trp Phe Gln Gln Lys Pro Gly Thr Ser Pro Lys Leu Trp Ile Tyr
1               5                   10                  15

<210> SEQ ID NO 51
<211> LENGTH: 15
<212> TYPE: PRT
<213> ORGANISM: Homo sapiens

<400> SEQUENCE: 51

Trp Phe Gln Gln Lys Pro Gly Gln Ala Pro Arg Leu Leu Ile Tyr
1               5                   10                  15

<210> SEQ ID NO 52
<211> LENGTH: 15
<212> TYPE: PRT
<213> ORGANISM: Homo sapiens

<400> SEQUENCE: 52
```

```
Trp Phe Gln Gln Lys Pro Gly Gln Ala Pro Arg Leu Trp Ile Tyr
1               5                   10                  15
```

<210> SEQ ID NO 53
<211> LENGTH: 15
<212> TYPE: PRT
<213> ORGANISM: Homo sapiens

<400> SEQUENCE: 53

```
Trp Tyr Gln Gln Lys Pro Gly Gln Ala Pro Arg Leu Leu Ile Tyr
1               5                   10                  15
```

<210> SEQ ID NO 54
<211> LENGTH: 32
<212> TYPE: PRT
<213> ORGANISM: Homo sapiens

<400> SEQUENCE: 54

```
Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30
```

<210> SEQ ID NO 55
<211> LENGTH: 32
<212> TYPE: PRT
<213> ORGANISM: Homo sapiens

<400> SEQUENCE: 55

```
Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 56
<211> LENGTH: 32
<212> TYPE: PRT
<213> ORGANISM: Homo sapiens

<400> SEQUENCE: 56

```
Gly Val Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30
```

<210> SEQ ID NO 57
<211> LENGTH: 32
<212> TYPE: PRT
<213> ORGANISM: Homo sapiens

<400> SEQUENCE: 57

```
Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30
```

<210> SEQ ID NO 58
<211> LENGTH: 32
<212> TYPE: PRT
<213> ORGANISM: Homo sapiens

<400> SEQUENCE: 58

```
Gly Ile Pro Ala Arg Phe Ser Gly Ser Gly Ser Gly Thr Asp Tyr Thr
```

```
           1               5                  10                  15
Leu Thr Ile Ser Ser Leu Glu Pro Glu Asp Phe Ala Val Tyr Tyr Cys
            20                  25                  30

<210> SEQ ID NO 59
<211> LENGTH: 10
<212> TYPE: PRT
<213> ORGANISM: Homo sapiens

<400> SEQUENCE: 59

Phe Gly Ser Gly Thr Lys Leu Glu Ile Lys
1               5                  10

<210> SEQ ID NO 60
<211> LENGTH: 10
<212> TYPE: PRT
<213> ORGANISM: Homo sapiens

<400> SEQUENCE: 60

Phe Gly Pro Gly Thr Lys Leu Asp Ile Lys
1               5                  10

<210> SEQ ID NO 61
<211> LENGTH: 5
<212> TYPE: PRT
<213> ORGANISM: Homo sapiens

<400> SEQUENCE: 61

Ile Tyr Gly Ala His
1               5

<210> SEQ ID NO 62
<211> LENGTH: 16
<212> TYPE: PRT
<213> ORGANISM: Homo sapiens

<400> SEQUENCE: 62

Val Ile Trp Ala Gly Gly Ser Thr Asn Tyr Asn Ser Ala Leu Met Ser
1               5                  10                  15

<210> SEQ ID NO 63
<211> LENGTH: 12
<212> TYPE: PRT
<213> ORGANISM: Homo sapiens

<400> SEQUENCE: 63

Asp Gly Ser Ser Pro Tyr Tyr Tyr Ser Met Glu Tyr
1               5                  10

<210> SEQ ID NO 64
<211> LENGTH: 10
<212> TYPE: PRT
<213> ORGANISM: Homo sapiens

<400> SEQUENCE: 64

Ser Ala Thr Ser Ser Val Ser Tyr Met His
1               5                  10

<210> SEQ ID NO 65
<211> LENGTH: 7
<212> TYPE: PRT
<213> ORGANISM: Homo sapiens

<400> SEQUENCE: 65
```

```
Ser Thr Ser Asn Leu Ala Ser
1               5
```

```
<210> SEQ ID NO 66
<211> LENGTH: 9
<212> TYPE: PRT
<213> ORGANISM: Homo sapiens

<400> SEQUENCE: 66

Gln Gln Arg Ser Ser Tyr Pro Phe Thr
1               5
```

```
<210> SEQ ID NO 67
<211> LENGTH: 12
<212> TYPE: PRT
<213> ORGANISM: Homo sapiens

<400> SEQUENCE: 67

Asp Gly Ser Ser Pro Tyr Tyr Tyr Gly Met Glu Tyr
1               5                   10
```

```
<210> SEQ ID NO 68
<211> LENGTH: 12
<212> TYPE: PRT
<213> ORGANISM: Homo sapiens

<400> SEQUENCE: 68

Asp Gly Ser Ser Pro Tyr Tyr Tyr Ser Met Asp Tyr
1               5                   10
```

```
<210> SEQ ID NO 69
<211> LENGTH: 12
<212> TYPE: PRT
<213> ORGANISM: Homo sapiens

<400> SEQUENCE: 69

Asp Gly Ser Ser Pro Tyr Tyr Tyr Ser Met Glu Val
1               5                   10
```

```
<210> SEQ ID NO 70
<211> LENGTH: 12
<212> TYPE: PRT
<213> ORGANISM: Homo sapiens

<400> SEQUENCE: 70

Asp Gly Ser Ser Pro Tyr Tyr Tyr Gly Met Asp Val
1               5                   10
```

```
<210> SEQ ID NO 71
<211> LENGTH: 9
<212> TYPE: PRT
<213> ORGANISM: Homo sapiens

<400> SEQUENCE: 71

Gln Gln Arg Ser Ser Tyr Pro Tyr Thr
1               5
```

```
<210> SEQ ID NO 72
<211> LENGTH: 474
<212> TYPE: PRT
<213> ORGANISM: Homo sapiens

<400> SEQUENCE: 72

Gly Tyr Leu Leu Gln Val Gln Glu Leu Val Thr Val Gln Glu Gly Leu
1               5                   10                  15
```

```
Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
                100                 105                 110

Gln Leu Asn Tyr Lys Thr Lys Gln Leu Ser Val Phe Val Thr Ala Leu
            115                 120                 125

Thr His Arg Pro Asp Ile Leu Ile Leu Gly Thr Leu Glu Ser Gly His
        130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ala Gly Ala Thr Ala Leu Ala Phe Leu Ser Phe
            340                 345                 350

Cys Ile Ile Phe Ile Ile Val Arg Ser Cys Arg Lys Lys Ser Ala Arg
        355                 360                 365

Pro Ala Ala Gly Val Gly Asp Thr Gly Met Glu Asp Ala Lys Ala Ile
370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Pro Ala Val Ala Pro Ser Ser Gly Glu
                405                 410                 415

Glu Gly Glu Leu His Tyr Ala Thr Leu Ser Phe His Lys Val Lys Pro
            420                 425                 430
```

```
Gln Asp Pro Gln Gly Gln Glu Ala Thr Asp Ser Glu Tyr Ser Glu Ile
            435                 440                 445

Lys Ile His Lys Arg Glu Thr Ala Glu Thr Gln Ala Cys Leu Arg Asn
450                 455                 460

His Asn Pro Ser Ser Lys Glu Val Arg Gly
465                 470

<210> SEQ ID NO 73
<211> LENGTH: 474
<212> TYPE: PRT
<213> ORGANISM: Homo sapiens

<400> SEQUENCE: 73

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Pro Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
    210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
    290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335
```

-continued

```
Ala Ala Val Gly Gly Ala Gly Ala Thr Ala Leu Ala Phe Leu Ser Phe
            340                 345                 350

Cys Ile Ile Phe Ile Ile Val Arg Ser Cys Arg Lys Lys Ser Ala Arg
            355                 360                 365

Pro Ala Ala Gly Val Gly Asp Thr Gly Met Glu Asp Ala Lys Ala Ile
            370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Ala Val Ala Pro Ser Ser Gly Glu
                405                 410                 415

Glu Gly Glu Leu His Tyr Ala Thr Leu Ser Phe His Lys Val Lys Pro
                420                 425                 430

Gln Asp Pro Gln Gly Gln Glu Ala Thr Asp Ser Glu Tyr Ser Glu Ile
            435                 440                 445

Lys Ile His Lys Arg Glu Thr Ala Glu Thr Gln Ala Cys Leu Arg Asn
            450                 455                 460

His Asn Pro Ser Ser Lys Glu Val Arg Gly
465                 470

<210> SEQ ID NO 74
<211> LENGTH: 573
<212> TYPE: PRT
<213> ORGANISM: Homo sapiens

<400> SEQUENCE: 74

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
                20                  25                  30

Asp Ser Asp Pro Val His Gly Tyr Trp Phe Arg Ala Gly Asp Arg Pro
            35                  40                  45

Tyr Gln Asp Ala Pro Val Ala Thr Asn Asn Pro Asp Arg Glu Val Gln
        50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
                100                 105                 110

Gln Leu Asn Tyr Lys Thr Lys Gln Leu Ser Val Phe Val Thr Ala Leu
            115                 120                 125

Thr His Arg Pro Asp Ile Leu Ile Leu Gly Thr Leu Glu Ser Gly His
        130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
                180                 185                 190

His Gly Thr Ser Leu Thr Cys Gln Val Thr Leu Pro Gly Thr Gly Val
            195                 200                 205

Thr Thr Thr Ser Thr Val Arg Leu Asp Val Ser Tyr Pro Pro Trp Asn
        210                 215                 220

Leu Thr Met Thr Val Phe Gln Gly Asp Ala Thr Ala Ser Thr Ala Leu
```

```
                225                 230                 235                 240
Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
    290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ile Glu Gly Arg Ser Asp Lys Thr His Thr Cys
            340                 345                 350

Pro Pro Cys Pro Ala Pro Glu Leu Leu Gly Gly Pro Ser Val Phe Leu
        355                 360                 365

Phe Pro Pro Lys Pro Lys Asp Thr Leu Met Ile Ser Arg Thr Pro Glu
    370                 375                 380

Val Thr Cys Val Val Val Asp Val Ser His Glu Asp Pro Glu Val Lys
385                 390                 395                 400

Phe Asn Trp Tyr Val Asp Gly Val Glu Val His Asn Ala Lys Thr Lys
                405                 410                 415

Pro Arg Glu Glu Gln Tyr Asn Ser Thr Tyr Arg Val Val Ser Val Leu
            420                 425                 430

Thr Val Leu His Gln Asp Trp Leu Asn Gly Lys Glu Tyr Lys Cys Lys
        435                 440                 445

Val Ser Asn Lys Ala Leu Pro Ala Pro Ile Glu Lys Thr Ile Ser Lys
    450                 455                 460

Ala Lys Gly Gln Pro Arg Glu Pro Gln Val Tyr Thr Leu Pro Pro Ser
465                 470                 475                 480

Arg Glu Glu Met Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
        515                 520                 525

Ser Phe Phe Leu Tyr Ser Lys Leu Thr Val Asp Lys Ser Arg Trp Gln
    530                 535                 540

Gln Gly Asn Val Phe Ser Cys Ser Val Met His Glu Ala Leu His Asn
545                 550                 555                 560

His Tyr Thr Gln Lys Ser Leu Ser Leu Ser Pro Gly Lys
                565                 570
```

<210> SEQ ID NO 75
<211> LENGTH: 449
<212> TYPE: PRT
<213> ORGANISM: Artificial Sequence
<220> FEATURE:
<223> OTHER INFORMATION: Synthetic Construct

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
```

```
                20                  25                  30
Gly Ala His Trp Val Arg Gln Ala Pro Gly Lys Gly Leu Glu Trp Val
             35                  40                  45
Gly Val Ile Trp Ala Gly Gly Ser Thr Asn Tyr Asn Ser Ala Leu Met
 50                  55                  60
Ser Arg Phe Thr Ile Ser Lys Asp Asn Ser Lys Asn Thr Val Tyr Leu
 65                  70                  75                  80
Gln Met Asn Ser Leu Arg Ala Glu Asp Thr Ala Val Tyr Tyr Cys Ala
                 85                  90                  95
Arg Asp Gly Ser Ser Pro Tyr Tyr Ser Met Glu Tyr Trp Gly Gln
                100                 105                 110
Gly Thr Thr Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
             130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
             195                 200                 205
Pro Ser Asn Thr Lys Val Asp Lys Arg Val Glu Pro Lys Ser Cys Asp
         210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
         275                 280                 285
Asn Ala Lys Thr Lys Pro Arg Glu Glu Gln Tyr Asn Ser Thr Tyr Arg
     290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
             340                 345                 350
Thr Leu Pro Pro Ser Arg Glu Glu Met Thr Lys Asn Gln Val Ser Leu
         355                 360                 365
Thr Cys Leu Val Lys Gly Phe Tyr Pro Ser Asp Ile Ala Val Glu Trp
     370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
```

Gly

<210> SEQ ID NO 76
<211> LENGTH: 213
<212> TYPE: PRT
<213> ORGANISM: Artificial Sequence
<220> FEATURE:
<223> OTHER INFORMATION: Synthetic Construct

<400> SEQUENCE: 76

```
Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 77
<211> LENGTH: 213
<212> TYPE: PRT
<213> ORGANISM: Artificial Sequence
<220> FEATURE:
<223> OTHER INFORMATION: Synthetic Construct

<400> SEQUENCE: 77

```
Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80
```

```
Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 78
<211> LENGTH: 329
<212> TYPE: PRT
<213> ORGANISM: Homo sapiens

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
```

```
225                 230                 235                 240
Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 79
<211> LENGTH: 326
<212> TYPE: PRT
<213> ORGANISM: Homo sapiens

<400> SEQUENCE: 79

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
                115                 120                 125

Asp Thr Leu Met Ile Ser Arg Thr Pro Glu Val Thr Cys Val Val Val
                130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
                195                 200                 205

Pro Ser Ser Ile Glu Lys Thr Ile Ser Lys Ala Lys Gly Gln Pro Arg
                210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270
```

```
Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 81
<211> LENGTH: 444
<212> TYPE: PRT
<213> ORGANISM: Mus musculus

<400> SEQUENCE: 81

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
        35                  40                  45

Leu Gly Val Ile Trp Ala Gly Gly Ser Thr Asn Tyr Asn Ser Ala Leu
    50                  55                  60

Met Ser Arg Leu Ser Ile Ser Lys Asp Asn Ser Lys Ser Gln Val Phe
65                  70                  75                  80

Leu Lys Ile Asn Ser Leu Gln Thr Asp Asp Thr Ala Leu Tyr Tyr Cys
                85                  90                  95

Ala Arg Asp Gly Ser Ser Pro Tyr Tyr Tyr Ser Met Glu Tyr Trp Gly
            100                 105                 110

Gln Gly Thr Ser Val Thr Val Ser Ser Ala Lys Thr Thr Pro Pro Ser
        115                 120                 125

Val Tyr Pro Leu Ala Pro Gly Ser Ala Ala Gln Thr Asn Ser Met Val
    130                 135                 140

Thr Leu Gly Cys Leu Val Lys Gly Tyr Phe Pro Glu Pro Val Thr Val
145                 150                 155                 160
```

```
Thr Trp Asn Ser Gly Ser Leu Ser Ser Gly Val His Thr Phe Pro Ala
                165                 170                 175

Val Leu Glu Ser Asp Leu Tyr Thr Leu Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
    210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
    290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
    370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly
        435                 440

<210> SEQ ID NO 82
<211> LENGTH: 212
<212> TYPE: PRT
<213> ORGANISM: Mus musculus

<400> SEQUENCE: 82

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95
```

```
Phe Gly Ser Gly Thr Lys Leu Glu Ile Lys Ala Asp Ala Ala Pro Thr
                100                 105                 110

Val Ser Ile Phe Pro Pro Ser Ser Glu Gln Leu Thr Ser Gly Gly Ala
            115                 120                 125

Ser Val Val Cys Phe Leu Asn Asn Phe Tyr Pro Lys Asp Ile Asn Val
        130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 83
<211> LENGTH: 212
<212> TYPE: PRT
<213> ORGANISM: Mus musculus

<400> SEQUENCE: 83

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Ala Asp Ala Ala Pro Thr
                100                 105                 110

Val Ser Ile Phe Pro Pro Ser Ser Glu Gln Leu Thr Ser Gly Gly Ala
            115                 120                 125

Ser Val Val Cys Phe Leu Asn Asn Phe Tyr Pro Lys Asp Ile Asn Val
        130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 84
<211> LENGTH: 450
<212> TYPE: PRT
```

<213> ORGANISM: Artificial Sequence
<220> FEATURE:
<223> OTHER INFORMATION: Synthetic Construct

<400> SEQUENCE: 84

```
Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
        35                  40                  45

Leu Gly Val Ile Trp Ala Gly Gly Ser Thr Asn Tyr Asn Ser Ala Leu
    50                  55                  60

Met Ser Arg Leu Ser Ile Ser Lys Asp Asn Ser Lys Ser Gln Val Phe
65                  70                  75                  80

Leu Lys Ile Asn Ser Leu Gln Thr Asp Asp Thr Ala Leu Tyr Tyr Cys
                85                  90                  95

Ala Arg Asp Gly Ser Ser Pro Tyr Tyr Tyr Ser Met Glu Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
```

```
385                 390                 395                 400
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 85
<211> LENGTH: 213
<212> TYPE: PRT
<213> ORGANISM: Artificial Sequence
<220> FEATURE:
<223> OTHER INFORMATION: Synthetic Construct

<400> SEQUENCE: 85

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Gln Ile Ile Leu Thr Gln Ser Pro Ala Ile Met Ser Ala Ser Pro Gly
1               5                   10                  15
```

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 87
<211> LENGTH: 446
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
            260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
            420                 425                 430
His Asn His Tyr Thr Gln Lys Ser Leu Ser Leu Ser Leu Gly
        435                 440                 445

<210> SEQ ID NO 88
<211> LENGTH: 5
<212> TYPE: PRT
<213> ORGANISM: Mus musculus

<400> SEQUENCE: 88

Ser Tyr Ala Met Ser
1               5

<210> SEQ ID NO 89
<211> LENGTH: 5
<212> TYPE: PRT
<213> ORGANISM: Mus musculus

<400> SEQUENCE: 89

Asp Tyr Tyr Met Tyr
1               5

<210> SEQ ID NO 90
<211> LENGTH: 5
```

<212> TYPE: PRT
<213> ORGANISM: Mus musculus

<400> SEQUENCE: 90

Ser Ser Trp Met Asn
1               5

<210> SEQ ID NO 91
<211> LENGTH: 17
<212> TYPE: PRT
<213> ORGANISM: Mus musculus

<400> SEQUENCE: 91

Ile Ile Ser Ser Gly Gly Ser Tyr Thr Tyr Tyr Ser Asp Ser Val Lys
1               5                   10                  15

Gly

<210> SEQ ID NO 92
<211> LENGTH: 17
<212> TYPE: PRT
<213> ORGANISM: Mus musculus

<400> SEQUENCE: 92

Arg Ile Ala Pro Glu Asp Gly Asp Thr Glu Tyr Ala Pro Lys Phe Gln
1               5                   10                  15

Gly

<210> SEQ ID NO 93
<211> LENGTH: 17
<212> TYPE: PRT
<213> ORGANISM: Mus musculus

<400> SEQUENCE: 93

Gln Ile Tyr Pro Gly Asp Asp Tyr Thr Asn Tyr Asn Gly Lys Phe Lys
1               5                   10                  15

Gly

<210> SEQ ID NO 94
<211> LENGTH: 11
<212> TYPE: PRT
<213> ORGANISM: Mus musculus

<400> SEQUENCE: 94

His Glu Thr Ala Gln Ala Ala Trp Phe Ala Tyr
1               5                   10

<210> SEQ ID NO 95
<211> LENGTH: 12
<212> TYPE: PRT
<213> ORGANISM: Mus musculus

<400> SEQUENCE: 95

Glu Gly Asn Tyr Tyr Gly Ser Ser Ile Leu Asp Tyr
1               5                   10

<210> SEQ ID NO 96
<211> LENGTH: 9
<212> TYPE: PRT
<213> ORGANISM: Mus musculus

<400> SEQUENCE: 96

Leu Gly Pro Tyr Gly Pro Phe Ala Asp
1               5

<210> SEQ ID NO 97
<211> LENGTH: 10
<212> TYPE: PRT
<213> ORGANISM: Mus musculus

<400> SEQUENCE: 97

Ser Ala Ser Ser Ser Val Ser Tyr Met His
1               5                   10

<210> SEQ ID NO 98
<211> LENGTH: 11
<212> TYPE: PRT
<213> ORGANISM: Mus musculus

<400> SEQUENCE: 98

Arg Ala Ser Gln Asp Ile Thr Asn Tyr Leu Asn
1               5                   10

<210> SEQ ID NO 99
<211> LENGTH: 10
<212> TYPE: PRT
<213> ORGANISM: Mus musculus

<400> SEQUENCE: 99

Ser Ala Ser Ser Ser Val Ser Tyr Met Tyr
1               5                   10

<210> SEQ ID NO 100
<211> LENGTH: 7
<212> TYPE: PRT
<213> ORGANISM: Mus musculus

<400> SEQUENCE: 100

Asp Thr Ser Lys Leu Ala Tyr
1               5

<210> SEQ ID NO 101
<211> LENGTH: 7
<212> TYPE: PRT
<213> ORGANISM: Mus musculus

<400> SEQUENCE: 101

Phe Thr Ser Arg Leu His Ser
1               5

<210> SEQ ID NO 102
<211> LENGTH: 7
<212> TYPE: PRT
<213> ORGANISM: Mus musculus

<400> SEQUENCE: 102

Asp Thr Ser Ser Leu Ala Ser
1               5

<210> SEQ ID NO 103
<211> LENGTH: 9
<212> TYPE: PRT
<213> ORGANISM: Mus musculus

<400> SEQUENCE: 103

Gln Gln Trp Ser Ser Asn Pro Pro Thr
1               5

```
<210> SEQ ID NO 104
<211> LENGTH: 9
<212> TYPE: PRT
<213> ORGANISM: Mus musculus

<400> SEQUENCE: 104

Gln Gln Gly Asn Thr Leu Pro Trp Thr
1               5

<210> SEQ ID NO 105
<211> LENGTH: 9
<212> TYPE: PRT
<213> ORGANISM: Mus musculus

<400> SEQUENCE: 105

Gln Gln Trp Asn Ser Asp Pro Tyr Thr
1               5

<210> SEQ ID NO 106
<211> LENGTH: 120
<212> TYPE: PRT
<213> ORGANISM: Mus musculus

<400> SEQUENCE: 106

Glu Val Gln Val Val Glu Ser Gly Gly Asp Leu Val Lys Ser Gly Gly
1               5                   10                  15

Ser Leu Lys Leu Ser Cys Ala Ala Ser Gly Phe Pro Phe Ser Ser Tyr
            20                  25                  30

Ala Met Ser Trp Val Arg Gln Thr Pro Asp Lys Arg Leu Glu Trp Val
        35                  40                  45

Ala Ile Ile Ser Ser Gly Gly Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Thr Ala Gln Ala Ala Trp Phe Ala Tyr Trp Gly Gln
            100                 105                 110

Gly Thr Leu Val Thr Val Ser Ala
        115                 120

<210> SEQ ID NO 107
<211> LENGTH: 121
<212> TYPE: PRT
<213> ORGANISM: Mus musculus

<400> SEQUENCE: 107

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Arg Ile Ala Pro Glu Asp Gly Asp Thr Gly Tyr Ala Pro Lys Phe
    50                  55                  60

Gln Gly Lys Ala Thr Val Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95
```

Thr Thr Glu Gly Asn Tyr Tyr Gly Ser Ser Ile Leu Asp Tyr Trp Gly
            100                 105                 110

Gln Gly Thr Thr Leu Thr Val Ser Ser
        115                 120

<210> SEQ ID NO 108
<211> LENGTH: 118
<212> TYPE: PRT
<213> ORGANISM: Mus musculus

<400> SEQUENCE: 108

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Arg Ser Ser
            20                  25                  30

Trp Met Asn Trp Val Lys Gln Arg Pro Gly Lys Gly Leu Glu Trp Ile
        35                  40                  45

Gly Gln Ile Tyr Pro Gly Asp Asp Tyr Thr Asn Tyr Asn Gly Lys Phe
    50                  55                  60

Lys Gly Lys Val Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Leu Gly Pro Tyr Gly Pro Phe Ala Asp Trp Gly Gln Gly Thr
            100                 105                 110

Leu Val Thr Val Ser Ala
        115

<210> SEQ ID NO 109
<211> LENGTH: 106
<212> TYPE: PRT
<213> ORGANISM: Mus musculus

<400> SEQUENCE: 109

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 110
<211> LENGTH: 107
<212> TYPE: PRT
<213> ORGANISM: Mus musculus

<400> SEQUENCE: 110

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr

```
            20                  25                  30
Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 111
<211> LENGTH: 106
<212> TYPE: PRT
<213> ORGANISM: Mus musculus

<400> SEQUENCE: 111

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Val Ser Tyr Met
            20                  25                  30

Tyr Trp Tyr Gln Gln Arg Pro Gly Ser Ser Pro Arg Leu Leu Ile Tyr
        35                  40                  45

Asp Thr Ser Ser Leu Ala Ser Gly Val Pro Val Arg Phe Ser Gly Ser
    50                  55                  60

Gly Ser Gly Thr Ser Tyr Ser Leu Thr Ile Ser Arg Ile Glu Ser Glu
65                  70                  75                  80

Asp Ala Ala Asn Tyr Tyr Cys Gln Gln Trp Asn Ser Asp Pro Tyr Thr
                85                  90                  95

Phe Gly Gly Gly Thr Lys Leu Glu Ile Lys
            100                 105

<210> SEQ ID NO 112
<211> LENGTH: 141
<212> TYPE: PRT
<213> ORGANISM: Homo sapiens

<400> SEQUENCE: 112

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
            115                 120                 125

Gln Leu Ser Val Phe Val Thr Ala Leu Thr His Arg Pro
```

```
                130                 135                 140

<210> SEQ ID NO 113
<211> LENGTH: 87
<212> TYPE: PRT
<213> ORGANISM: Homo sapiens

<400> SEQUENCE: 113

Asp Ile Leu Ile Leu Gly Thr Leu Glu Ser Gly His Ser Arg Asn Leu
1               5                   10                  15

Thr Cys Ser Val Pro Trp Ala Cys Lys Gln Gly Thr Pro Pro Met Ile
            20                  25                  30

Ser Trp Ile Gly Ala Ser Val Ser Pro Gly Pro Thr Thr Ala Arg
        35                  40                  45

Ser Ser Val Leu Thr Leu Thr Pro Lys Pro Gln Asp His Gly Thr Ser
    50                  55                  60

Leu Thr Cys Gln Val Thr Leu Pro Gly Thr Gly Val Thr Thr Thr Ser
65                  70                  75                  80

Thr Val Arg Leu Asp Val Ser
                85

<210> SEQ ID NO 114
<211> LENGTH: 122
<212> TYPE: PRT
<213> ORGANISM: Homo sapiens

<400> SEQUENCE: 114

Tyr Pro Pro Trp Asn Leu Thr Met Thr Val Phe Gln Gly Asp Ala Thr
1               5                   10                  15

Ala Ser Thr Ala Leu Gly Asn Gly Ser Ser Leu Ser Val Leu Glu Gly
            20                  25                  30

Gln Ser Leu Arg Leu Val Cys Ala Val Asn Ser Asn Pro Pro Ala Arg
        35                  40                  45

Leu Ser Trp Thr Arg Gly Ser Leu Thr Leu Cys Pro Ser Arg Ser Ser
    50                  55                  60

Asn Pro Gly Leu Leu Glu Leu Pro Arg Val His Val Arg Asp Glu Gly
65                  70                  75                  80

Glu Phe Thr Cys Arg Ala Gln Asn Ala Gln Gly Ser Gln His Ile Ser
                85                  90                  95

Leu Ser Leu Ser Leu Gln Asn Glu Gly Thr Gly Thr Ser Arg Pro Val
            100                 105                 110

Ser Gln Val Thr Leu Ala Ala Val Gly Gly
        115                 120

<210> SEQ ID NO 115
<211> LENGTH: 373
<212> TYPE: PRT
<213> ORGANISM: Homo sapiens

<400> SEQUENCE: 115

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60
```

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
            85                  90                  95

Asp Ala Arg Lys Arg Asp Lys Gly Ser Tyr Phe Phe Arg Leu Glu Arg
        100                 105                 110

Gly Ser Met Lys Trp Ser Tyr Lys Ser Gln Leu Asn Tyr Lys Thr Lys
    115                 120                 125

Gln Leu Ser Val Phe Val Thr Ala Leu Thr His Arg Pro Ile Glu Gly
130                 135                 140

Arg Ser Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
                180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
                260                 265                 270

Gln Val Tyr Thr Leu Pro Pro Ser Arg Glu Glu Met Thr Lys Asn Gln
        275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
                340                 345                 350

Val Met His Glu Ala Leu His Asn His Tyr Thr Gln Lys Ser Leu Ser
        355                 360                 365

Leu Ser Pro Gly Lys
        370

<210> SEQ ID NO 116
<211> LENGTH: 460
<212> TYPE: PRT
<213> ORGANISM: Homo sapiens

<400> SEQUENCE: 116

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala

```
              50                  55                  60
Thr Asn Asn Pro Asp Arg Glu Val Gln Ala Glu Thr Gln Gly Arg Phe
 65                  70                  75                  80

Gln Leu Leu Gly Asp Ile Trp Ser Asn Asp Cys Ser Leu Ser Ile Arg
                 85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
            115                 120                 125

Gln Leu Ser Val Phe Val Thr Ala Leu Thr His Arg Pro Asp Ile Leu
130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
            165                 170                 175

Gly Ala Ser Val Ser Ser Pro Gly Pro Thr Thr Ala Arg Ser Ser Val
            180                 185                 190

Leu Thr Leu Thr Pro Lys Pro Gln Asp His Gly Thr Ser Leu Thr Cys
            195                 200                 205

Gln Val Thr Leu Pro Gly Thr Gly Val Thr Thr Thr Ser Thr Val Arg
210                 215                 220

Leu Asp Val Ser Ile Glu Gly Arg Ser Asp Lys Thr His Thr Cys Pro
225                 230                 235                 240

Pro Cys Pro Ala Pro Glu Leu Leu Gly Gly Pro Ser Val Phe Leu Phe
            245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
            290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
            370                 375                 380

Phe Tyr Pro Ser Asp Ile Ala Val Glu Trp Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 117
```

```
<211> LENGTH: 582
<212> TYPE: PRT
<213> ORGANISM: Homo sapiens

<400> SEQUENCE: 117

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
        115                 120                 125

Gln Leu Ser Val Phe Val Thr Ala Leu Thr His Arg Pro Asp Ile Leu
    130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
                165                 170                 175

Gly Ala Ser Val Ser Ser Pro Gly Pro Thr Thr Ala Arg Ser Ser Val
            180                 185                 190

Leu Thr Leu Thr Pro Lys Pro Gln Asp His Gly Thr Ser Leu Thr Cys
        195                 200                 205

Gln Val Thr Leu Pro Gly Thr Gly Val Thr Thr Thr Ser Thr Val Arg
    210                 215                 220

Leu Asp Val Ser Tyr Pro Pro Trp Asn Leu Thr Met Thr Val Phe Gln
225                 230                 235                 240

Gly Asp Ala Thr Ala Ser Thr Ala Leu Gly Asn Gly Ser Ser Leu Ser
                245                 250                 255

Val Leu Glu Gly Gln Ser Leu Arg Leu Val Cys Ala Val Asn Ser Asn
            260                 265                 270

Pro Pro Ala Arg Leu Ser Trp Thr Arg Gly Ser Leu Thr Leu Cys Pro
        275                 280                 285

Ser Arg Ser Ser Asn Pro Gly Leu Leu Glu Leu Pro Arg Val His Val
    290                 295                 300

Arg Asp Glu Gly Glu Phe Thr Cys Arg Ala Gln Asn Ala Gln Gly Ser
305                 310                 315                 320

Gln His Ile Ser Leu Ser Leu Ser Leu Gln Asn Glu Gly Thr Gly Thr
                325                 330                 335

Ser Arg Pro Val Ser Gln Val Thr Leu Ala Ala Val Gly Gly Ile Glu
            340                 345                 350

Gly Arg Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
```

```
                385                 390                 395                 400
Val Ser His Glu Asp Pro Glu Val Lys Phe Asn Trp Tyr Val Asp Gly
                405                 410                 415
Val Glu Val His Asn Ala Lys Thr Lys Pro Arg Glu Glu Gln Tyr Asn
                420                 425                 430
Ser Thr Tyr Arg Val Val Ser Val Leu Thr Val Leu His Gln Asp Trp
                435                 440                 445
Leu Asn Gly Lys Glu Tyr Lys Cys Lys Val Ser Asn Lys Ala Leu Pro
            450                 455                 460
Ala Pro Ile Glu Lys Thr Ile Ser Lys Ala Lys Gly Gln Pro Arg Glu
465                 470                 475                 480
Pro Gln Val Tyr Thr Leu Pro Pro Ser Arg Asp Glu Leu Thr Lys Asn
                485                 490                 495
Gln Val Ser Leu Thr Cys Leu Val Lys Gly Phe Tyr Pro Ser Asp Ile
                500                 505                 510
Ala Val Glu Trp Glu Ser Asn Gly Gln Pro Glu Asn Asn Tyr Lys Thr
                515                 520                 525
Thr Pro Pro Val Leu Asp Ser Asp Gly Ser Phe Phe Leu Tyr Ser Lys
            530                 535                 540
Leu Thr Val Asp Lys Ser Arg Trp Gln Gln Gly Asn Val Phe Ser Cys
545                 550                 555                 560
Ser Val Met His Glu Ala Leu His Asn His Tyr Thr Gln Lys Ser Leu
                565                 570                 575
Ser Leu Ser Pro Gly Lys
                580

<210> SEQ ID NO 118
<211> LENGTH: 582
<212> TYPE: PRT
<213> ORGANISM: Unknown
<220> FEATURE:
<223> OTHER INFORMATION: Papio spp.

<400> SEQUENCE: 118

Met Glu Gly Asp Arg Lys Tyr Gly Asp Gly Tyr Leu Leu Gln Val Gln
1               5                   10                  15
Glu Leu Val Thr Val Gln Glu Gly Leu Cys Val His Val Pro Cys Ser
                20                  25                  30
Phe Ser Tyr Pro Lys Asp Asp Trp Thr Tyr Ser Asp Pro Val His Gly
                35                  40                  45
Tyr Trp Phe Arg Ala Gly Asp Arg Pro Tyr Gln Glu Ala Pro Val Ala
            50                  55                  60
Thr Asn Asn Pro Asp Thr Glu Val Gln Ala Glu Thr Gln Gly Arg Phe
65              70                  75                  80
Gln Leu Leu Gly Asp Arg Trp Ser Asn Asp Cys Ser Leu Ser Ile Asn
                85                  90                  95
Asp Ala Arg Lys Gly Asp Glu Gly Ser Tyr Phe Phe Arg Leu Glu Arg
                100                 105                 110
Gly Arg Met Lys Trp Ser Tyr Lys Ser Gln Leu Asn Tyr Lys Ala Lys
                115                 120                 125
Gln Leu Ser Val Phe Val Thr Ala Leu Thr Gln Arg Pro Asp Ile Leu
            130                 135                 140
Ile Gln Gly Thr Leu Glu Ser Gly His Pro Arg Asn Leu Thr Cys Ser
145                 150                 155                 160
Val Pro Trp Ala Cys Glu Gln Arg Met Pro Pro Met Ile Ser Trp Ile
```

```
                    165                 170                 175
Gly Thr Ser Val Ser Ser Leu Gly Pro Ile Thr Ala Arg Phe Ser Val
                180                 185                 190

Leu Thr Leu Ile Pro Lys Pro Gln Asp His Gly Thr Ser Leu Thr Cys
            195                 200                 205

Gln Val Thr Leu Pro Gly Thr Gly Val Thr Thr Arg Thr Val Gln
210                 215                 220

Leu Asp Val Ser Tyr Pro Pro Trp Asn Leu Thr Val Thr Val Phe Gln
225                 230                 235                 240

Gly Asp Asp Thr Ala Ser Thr Ala Leu Gly Asn Gly Ser Ser Leu Ser
                245                 250                 255

Val Leu Glu Gly Gln Ser Leu Arg Leu Val Cys Ala Val Asp Ser Asn
            260                 265                 270

Pro Pro Ala Arg Leu Ser Trp Thr Arg Gly Ser Leu Thr Leu Cys Pro
        275                 280                 285

Ser Gln Pro Trp Asn Pro Gly Leu Leu Glu Leu Leu Arg Val His Val
    290                 295                 300

Lys Asp Glu Gly Glu Phe Thr Cys Gln Ala Glu Asn Pro Arg Gly Ser
305                 310                 315                 320

Gln His Ile Ser Leu Ser Leu Ser Leu Gln Asn Glu Gly Thr Gly Thr
                325                 330                 335

Ala Arg Pro Val Ser Glu Val Thr Leu Ala Ala Val Gly Gly Ile Glu
            340                 345                 350

Gly Arg Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
            420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Glu Glu Met Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Lys
    530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580
```

<210> SEQ ID NO 119
<211> LENGTH: 350
<212> TYPE: PRT
<213> ORGANISM: Unknown
<220> FEATURE:
<223> OTHER INFORMATION: Papio spp.

<400> SEQUENCE: 119

Met Glu Gly Asp Arg Lys Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Lys Asp Asp Trp Thr Tyr Ser Asp Pro Val His Gly
        35                  40                  45

Tyr Trp Phe Arg Ala Gly Asp Arg Pro Tyr Gln Glu Ala Pro Val Ala
    50                  55                  60

Thr Asn Asn Pro Asp Thr Glu Val Gln Ala Glu Thr Gln Gly Arg Phe
65                  70                  75                  80

Gln Leu Leu Gly Asp Arg Trp Ser Asn Asp Cys Ser Leu Ser Ile Asn
                85                  90                  95

Asp Ala Arg Lys Gly Asp Glu Gly Ser Tyr Phe Phe Arg Leu Glu Arg
            100                 105                 110

Gly Arg Met Lys Trp Ser Tyr Lys Ser Gln Leu Asn Tyr Lys Ala Lys
        115                 120                 125

Gln Leu Ser Val Phe Val Thr Ala Leu Thr Gln Arg Pro Asp Ile Leu
    130                 135                 140

Ile Gln Gly Thr Leu Glu Ser Gly His Pro Arg Asn Leu Thr Cys Ser
145                 150                 155                 160

Val Pro Trp Ala Cys Glu Gln Arg Met Pro Pro Met Ile Ser Trp Ile
                165                 170                 175

Gly Thr Ser Val Ser Ser Leu Gly Pro Ile Thr Ala Arg Phe Ser Val
            180                 185                 190

Leu Thr Leu Ile Pro Lys Pro Gln Asp His Gly Thr Ser Leu Thr Cys
        195                 200                 205

Gln Val Thr Leu Pro Gly Thr Gly Val Thr Thr Arg Thr Val Gln
    210                 215                 220

Leu Asp Val Ser Tyr Pro Pro Trp Asn Leu Thr Val Thr Val Phe Gln
225                 230                 235                 240

Gly Asp Asp Thr Ala Ser Thr Ala Leu Gly Asn Gly Ser Ser Leu Ser
                245                 250                 255

Val Leu Glu Gly Gln Ser Leu Arg Leu Val Cys Ala Val Asp Ser Asn
            260                 265                 270

Pro Pro Ala Arg Leu Ser Trp Thr Arg Gly Ser Leu Thr Leu Cys Pro
        275                 280                 285

Ser Gln Pro Trp Asn Pro Gly Leu Leu Glu Leu Leu Arg Val His Val
    290                 295                 300

Lys Asp Glu Gly Glu Phe Thr Cys Gln Ala Glu Asn Pro Arg Gly Ser
305                 310                 315                 320

Gln His Ile Ser Leu Ser Leu Ser Leu Gln Asn Glu Gly Thr Gly Thr
                325                 330                 335

Ala Arg Pro Val Ser Glu Val Thr Leu Ala Ala Val Gly Gly
            340                 345                 350

<210> SEQ ID NO 120

```
<211> LENGTH: 120
<212> TYPE: PRT
<213> ORGANISM: Homo sapiens

<400> SEQUENCE: 120

Glu Val Lys Val Glu Glu Ser Gly Gly Gly Leu Val Gln Pro Gly Gly
1               5                   10                  15

Ser Leu Arg Leu Ser Cys Ala Ala Ser Gly Phe Ser Leu Thr Ile Thr
            20                  25                  30

Tyr Met Asn Trp Val Arg Gln Ala Pro Gly Lys Gly Leu Glu Trp Val
        35                  40                  45

Ser Val Ile Gly Ser Ala Gly Ser Thr Tyr Tyr Ala Asp Ser Val Lys
    50                  55                  60

Gly Arg Phe Thr Ile Ser Lys Asp Asn Ser Glu Gly Met Val Tyr Leu
65                  70                  75                  80

Gln Met Asn Ser Leu Arg Ala Glu Asp Thr Ala Val Tyr Tyr Cys Ala
                85                  90                  95

Arg Glu Glu Ile Asp Asn Tyr Tyr Tyr Gly Met Asp Val Trp Gly Gln
            100                 105                 110

Gly Thr Thr Val Thr Val Ser Ser
        115                 120

<210> SEQ ID NO 121
<211> LENGTH: 97
<212> TYPE: PRT
<213> ORGANISM: Homo sapiens

<400> SEQUENCE: 121

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 122
<211> LENGTH: 97
<212> TYPE: PRT
<213> ORGANISM: Homo sapiens

<400> SEQUENCE: 122

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
```

```
                65                  70                  75                  80
Lys Leu Ser Ser Val Thr Ala Ala Asp Thr Ala Val Tyr Tyr Cys Ala
                    85                  90                  95
Arg

<210> SEQ ID NO 123
<211> LENGTH: 107
<212> TYPE: PRT
<213> ORGANISM: Homo sapiens

<400> SEQUENCE: 123

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Ser Tyr
                20                  25                  30

Leu Ala Trp Phe Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Leu Ile
                85                  90                  95

Ala Phe Gly Pro Gly Thr Lys Leu Asp Ile Lys
                100                 105

<210> SEQ ID NO 124
<211> LENGTH: 95
<212> TYPE: PRT
<213> ORGANISM: Homo sapiens

<400> SEQUENCE: 124

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95
```